United States Patent
Friesen et al.

(10) Patent No.: US 11,052,082 B2
(45) Date of Patent: Jul. 6, 2021

(54) COMBINATION OF OPIOIDS AND ANTICANCER DRUGS FOR CANCER TREATMENT

(71) Applicant: UNIVERSITÄT ULM, Ulm (DE)

(72) Inventors: Claudia Friesen, Ulm (DE); Erich Miltner, Ulm (DE)

(73) Assignee: UNIVERSITÄT ULM, Ulm (DE)

( * ) Notice: Subject to any disclaimer, the term of this patent is extended or adjusted under 35 U.S.C. 154(b) by 0 days.

(21) Appl. No.: 16/000,467

(22) Filed: Jun. 5, 2018

(65) Prior Publication Data

US 2018/0280380 A1    Oct. 4, 2018

Related U.S. Application Data

(62) Division of application No. 14/434,138, filed as application No. PCT/EP2013/070923 on Oct. 8, 2013, now abandoned.

(30) Foreign Application Priority Data

Oct. 8, 2012   (EP) .................................. 12006946
Oct. 17, 2012  (EP) .................................. 12007179

(51) Int. Cl.

| | | |
|---|---|---|
| *A61K 31/137* | (2006.01) | |
| *A61K 31/485* | (2006.01) | |
| *A61K 31/704* | (2006.01) | |
| *A61K 45/06* | (2006.01) | |
| *A61K 31/4468* | (2006.01) | |
| *A61K 31/7048* | (2006.01) | |
| *A61K 31/7076* | (2006.01) | |
| *A61K 33/24* | (2019.01) | |
| *G01N 33/50* | (2006.01) | |
| *A61K 31/445* | (2006.01) | |

(52) U.S. Cl.
CPC .......... *A61K 31/485* (2013.01); *A61K 31/137* (2013.01); *A61K 31/445* (2013.01); *A61K 31/4468* (2013.01); *A61K 31/704* (2013.01); *A61K 31/7048* (2013.01); *A61K 31/7076* (2013.01); *A61K 33/24* (2013.01); *A61K 45/06* (2013.01); *G01N 33/5011* (2013.01); *G01N 33/5014* (2013.01); *G01N 2500/04* (2013.01)

(58) Field of Classification Search
CPC ... A61K 31/485; A61K 31/137; A61K 31/704
See application file for complete search history.

(56) References Cited

U.S. PATENT DOCUMENTS

2007/0196493 A1* 8/2007 Klinski ................ A61K 31/704
2011/0270011 A1   11/2011 Miltner et al.

FOREIGN PATENT DOCUMENTS

| CN | 102159212 A | 8/2011 |
|---|---|---|
| EP | 2149372 A1 | 3/2010 |
| WO | 2009117669 A2 | 9/2009 |

OTHER PUBLICATIONS

Lesniak et al. Anticancer Res., 2005, vol. 25, No. 6b, pp. 3825-3831.*
British Pain Society, The British Pain Society, Jan. 2010, pp. 1-115.*
Parsons et al. Cancer, 2010, vol. 116, No. 2, pp. 520-528.*
Russian Office Action for Application No. 2015114786/15 dated Dec. 15, 2017.
Regine Lupertz, et al. "Dose- and time-dependent effects of doxorubicin on cytotoxicity, cellcycle and apoptotic cell deathin human color cancer cells"// Toxicology 271, 115-121, 2010, p. 117, fig. 1D.
Aronson J.K. "Meyler's side effects of analgesics and anti-inflammatory drugs"// Elsevier, 702, Dec. 22, 2009.
D.A. Harkevich, Pharmacologya, M., GEOTAR-Media, 2009, p. 66.
McSweeney et al. Experimental and Psychopharmacology, 2005, vol. 13, No. 3, abstract.
Office Action and Patent Search for corresponding RU appl. No. 2015114786 dated Jun. 30, 2017, pp. 1-8.
Notification of the First Office Action from the State Intellectual Property Office of the People's Republic of China for Application No. 201380060492.7, dated Jul. 27, 2016, pp. 1-9.
Maneckjee et al. Proc. Natl. Acad. Sci., 1992, vol. 89, pp. 1169-1173.
Lin et al. International J. of Nanomedicine, 2012, pp. 4169-4183.
International Search Report for PCT/EP2013/070923, dated Nov. 11, 2013, pp. 1-2.

* cited by examiner

Primary Examiner — Samira J Jean-Louis
(74) Attorney, Agent, or Firm — Tarolli, Sundheim, Covell & Tummino LLP

(57) ABSTRACT

The invention relates to novel strategies for the treatment of cancer patients based on a combination of an opioid receptor agonist and an anticancer compound.

28 Claims, 61 Drawing Sheets

Figure 4
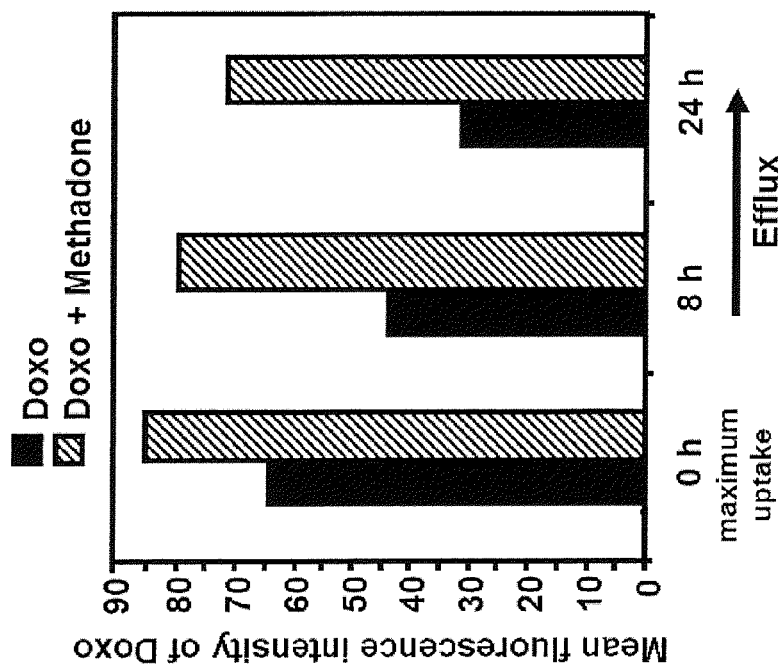
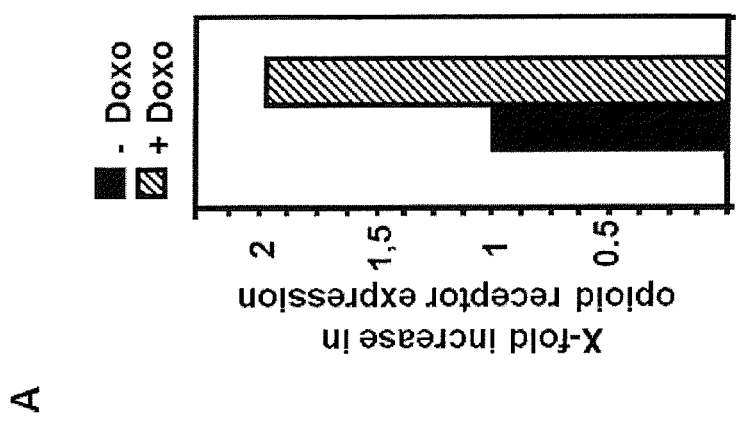

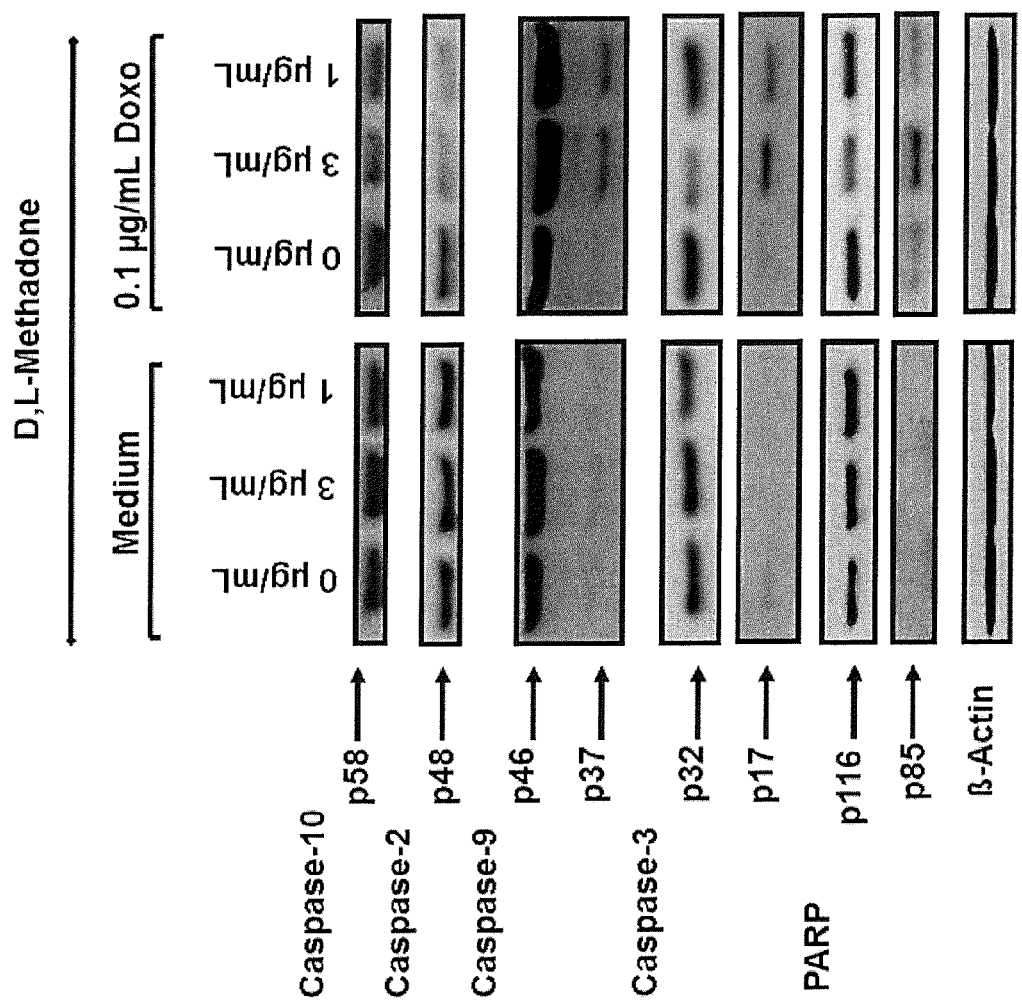

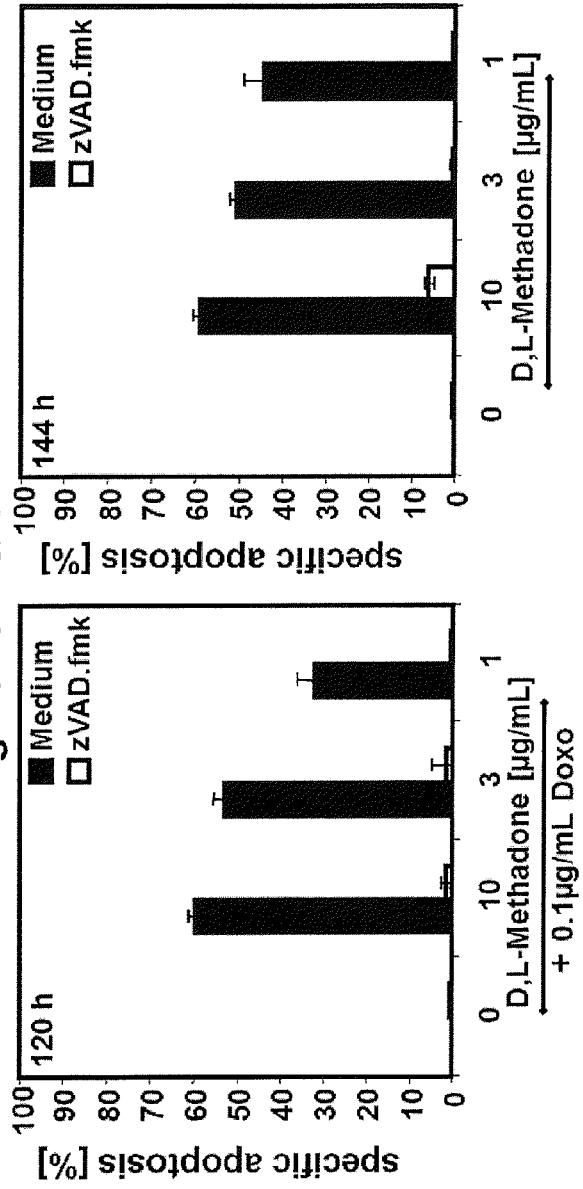
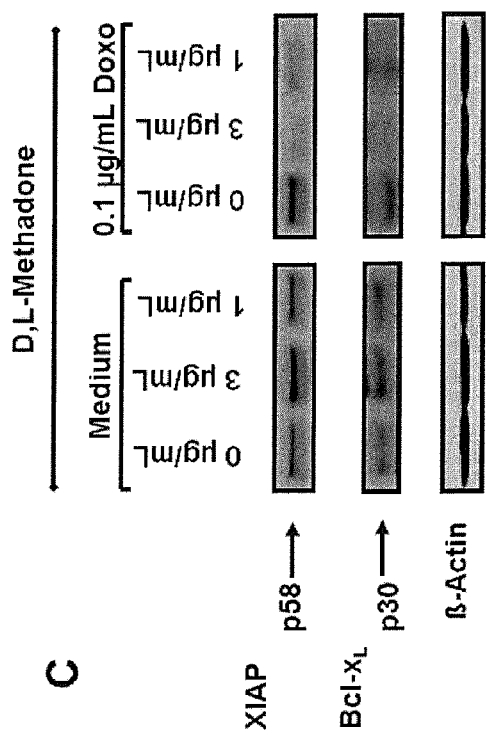
Figure 13 B & C

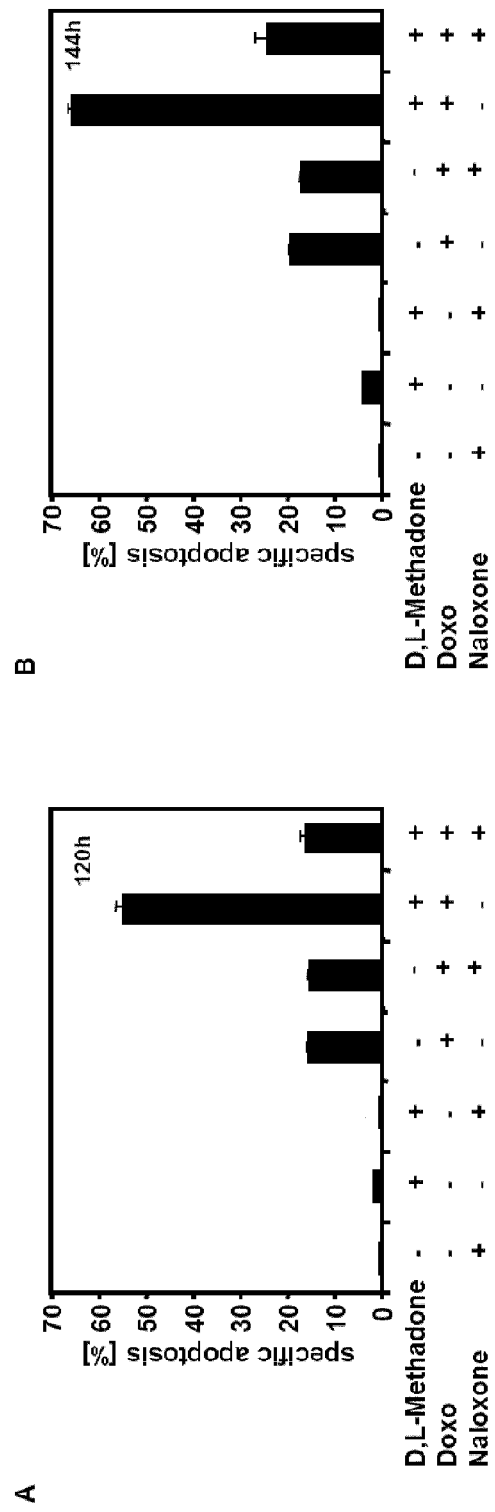
Figure 36 A,B

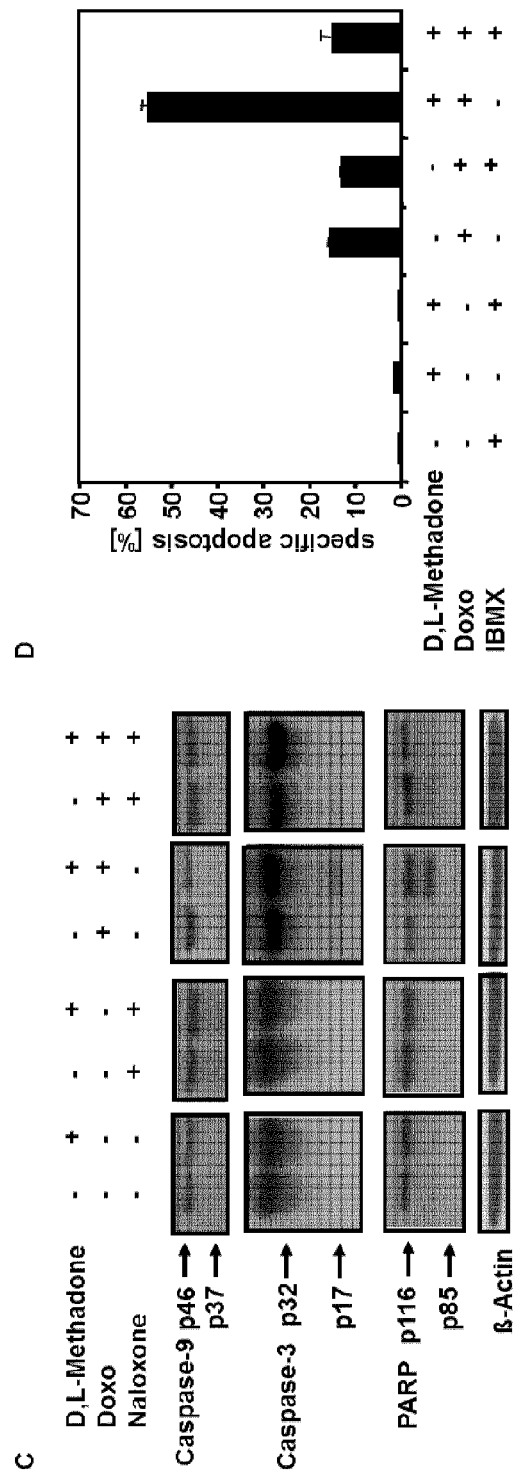
Figure 36 C,D

COMBINATION OF OPIOIDS AND ANTICANCER DRUGS FOR CANCER TREATMENT

RELATED APPLICATIONS

The present invention is a divisional application of U.S. patent application Ser. No. 14/434,138, filed Apr. 8, 2015, which is a U.S. National Stage under 35 USC 371 patent application, claiming priority to International Application No. PCT/EP2013/070923, filed on Oct. 8, 2013, which claims priority from European Patent Application No. 12006946.3, filed Oct. 8, 2012, and European Patent Application No. 12007179.0, filed Oct. 17, 2012, the entirety of all of which are incorporated herein by reference.

TECHNICAL FIELD

The invention relates to novel strategies for the treatment of cancer patients based on a combination of an opioid receptor agonist and an anticancer compound.

BACKGROUND OF THE INVENTION

Cancer can be defined as an abnormal growth of tissue characterized by a loss of cellular differentiation. This term encompasses a large group of diseases in which there is an invasive spread of undifferentiated cells from a primary site to other parts of the body where further undifferentiated cellular replication occurs, which eventually interferes the normal functioning of tissues and organs.

Cancers are primarily an environmental disease with 90-95% of cases attributed to environmental factors and 5-10% due to genetics. Environmental, as used by cancer researchers, means any cause that is not inherited genetically, not merely pollution. Common environmental factors that contribute to cancer death include tobacco (25-30%), diet and obesity (30-35%), infections (15-20%), radiation (both ionizing and non-ionizing, up to 10%), stress, lack of physical activity, and environmental pollutants.

With more than 3 million new cases and 1.7 million deaths each year, cancer represents the second most important cause of death and morbidity in Europe. On a global scale, cancer accounted for 7.4 million deaths (around 13% of the total) in 2004.

Although more than 40% of cancer deaths can be prevented, cancer is a leading cause of death, causing 20% of the total in the European Region. Noticeably, Europe comprising only one eighth of the total world population but has around one quarter of the global total of cancer cases: some 3.2 million new patients per year.

The most common forms of cancer were prostate, colorectal, breast, leukemia and lung cancer. The risk of getting cancer before the age of 75 years is 26.5%, or around one in four. However, because the population of Europe is ageing, the rate of new cases of cancer is also expected to increase.

Each cancer is characterized by the site, nature, and clinical cause of undifferentiated cellular proliferation, whereby the underlying mechanism for the initiation of cancer is not completely understood.

Cancer is usually treated with chemotherapy, radiation therapy and surgery. Chemotherapy in addition to surgery has proven useful in a number of different cancer types including: breast cancer, colorectal cancer, pancreatic cancer, osteogenic sarcoma, testicular cancer, ovarian cancer, and certain lung cancers. Radiation therapy involves the use of ionizing radiation in an attempt to either cure or improve the symptoms of cancer. It is used in about half of all cases and the radiation can be from either internal sources in the form of brachytherapy or external sources. Radiation is typically used in addition to surgery and or chemotherapy but for certain types of cancer such as early head and neck cancer may be used alone. For painful bone metastasis it has been found to be effective in about 70% of people.

Despite the numerous therapeutic strategies there are still tumours which cannot be effectively treated with the current treatment options. In addition, the effectiveness of radiation- and chemotherapy is often limited by toxicity to other tissues in the body. Furthermore, anticancer therapies are frequently ineffective due to resistance of the tumour cells to radio- and/or chemotherapy.

Thus in oncology there is a great need for novel strategies, which render cancer treatments more effective. In particular, it is the objective of the present invention to provide novel means for treating cancer patients.

SUMMARY OF THE INVENTION

This objective is solved by using a combination of opioid receptor agonists and anticancer drugs for the treatment of cancer wherein this combination is given in a specific administration scheme according to claim 1 of the invention.

In a first aspect the invention relates to a combination of an opioid receptor agonist and at least one anticancer agent for use in the treatment of cancer, wherein
  (a) said opioid receptor agonist is administered to a patient in one or more doses to establish a therapeutically effective plasma level for a period of at least one week, and
  (b) at least one anticancer agent selected from the group consisting of chemotherapeutical agents, cytotoxic agents, cytostatic agents, immunotoxic agents and/or radiotherapy is administered to establish a period with a therapeutically effective plasma level, and
  (c) said periods of a) and b) overlap.

This combination therapy is based on the unexpected finding that opioid receptor agonists together with anticancer agents kill cancer cells more effectively. Furthermore, the inventors could show that the interaction between opioid receptor agonists and anticancer agents represents a self-reinforcing feedback loop as illustrated by FIG. 26. In the first path of this loop opioid receptor agonists enhance the cellular uptake and inhibit the efflux of anticancer drugs. In the second path of said loop the accumulating anticancer drugs lead to an increased expression of opioid receptors on the surface of the cancer cell. Hence, both the opioid receptor agonist and the anticancer agent can exert their cytotoxic potential to a higher extent.

Furthermore the invention is based on the unexpected finding that the amount of opioid receptor expressed on the cell surface of cancer cells is varying among the different cancer types and also exhibiting inter-individual differences and that this surface-associated opioid receptor expression can be increased by anticancer agents. For example doxorubicin, idarubicin, epirubicin, daunorubicin, carboplatin, oxaliplatin, cisplatin, etoposide, methotrexate, cytarabine, teniposide, rituximab fludarabine, are able to induce an increase of the number of opioid receptors which are expressed on the cell surface of cancer cells.

By extensive in vitro and in vivo experiments it could be shown that different cancer types can be subjected to the combination therapy of the invention. Furthermore also different anticancer drugs and different opioids proved to be active in the above described feedback loop.

Therefore, the combination therapy of opioid receptor agonist and anticancer drug according to the invention can improve cancer therapy by one or more of the following ways:
- Due to the upregulation of opioid receptors, former opioid insensitive cancer types could be subjected to an opioid receptor agonist therapy.
- Due to the opioid-receptor-agonist-induced intracellular accumulation (by either an increased uptake of anticancer drugs or a reduced efflux or a combination of both) of anticancer drugs the efficacy of the treatment is enhanced.
- This could lead to therapy of cancer types which are non-treatable or not effectively treatable by conventional therapeutic anticancer approaches.
- Furthermore, this might allow a dose reduction for the anticancer drugs enhancing the safety and patient compliance of the chemotherapy.
- Finally, also resistant cancer cells could be re-sensitized for an anticancer treatment.
- In addition, the numerous opioids and numerous anticancer drugs on the market open up the way for new drug combinations which might represent improved treatment due to increased efficacy and/or safety.

In the context of the present invention the term "opioid receptor agonist" is defined as a chemical heterogeneous group of natural, synthetic or semi-synthetic substances, working agonistic at the same type of receptor, the so called opioid receptor. According to the analgesia and side effect profile five types of opioid receptors, the μ-receptor (ligand=morphine), the κ[kappa]-receptor (ligand=ketazocine), the delta-receptor (ligand=deltorphine II), the σ[sigma]-receptor (ligand=SKF 10081), as well as the later-identified ORL1-receptor (ligand=nociceptin) are known. Corresponding to other receptor systems, binding studies as well as functional investigations indicate that subtypes of opioid receptors exist. Within the μ- and δ'-receptor type 2 subtypes, the μ-1 and μ-2 and δ-1 and δ-2 have been described. The κ-receptor contains an additional κ-3 subtype. Especially in regards to the μ-opioid receptor its two subtypes are included in this invention.

The term "opioid receptor agonist" as used herein comprises full agonists as well as mixed agonists/antagonists or partial agonists such as buprenorphine.

The group of opioids includes natural opiates such as alkaloids like morphine or dihydrocodeine, as well as semi-synthetic opiates, derived from the natural opiates (e.g. hydromorphone or oxycodone), or fully synthetic opioids, such as fentanyl or buprenorphine. It also includes endogenous opioid peptides, which may be produced naturally in the body as endorphins, dynorphins or enkephalins but which can also be synthesized.

DETAILED DESCRIPTION

As used herein the term "anticancer drug" encompasses all chemical or physical interventions that are used for the treatment of cancer. It therefore includes chemotherapeutical agents such as cytotoxic agents or immunotoxic agents but also radioactively labelled antibodies, peptides and chemical substances, which might emit alpha, beta and gamma rays as well as electrons. The radiotherapy further includes photons of sufficiently high energy, charged particles such as electrons, positrons, muons, protons, alpha particles, and heavy atomic nuclei from accelerators, but also neutrons and gamma rays.

The term "therapeutically effective plasma level" is defined as a plasma level that is between the plasma level of the drug that causes a lethal effect and the minimum plasma level that causes a therapeutic effect. In the context of the invention the therapeutic effect of the opioid receptor agonist is given by the increase in cellular uptake and/or the inhibition of the cellular efflux of the co-administered anticancer drug and/or the induction of cell death by e.g. apoptosis, necrosis, mitotic catastrophe and autophagy. In the context of the invention the therapeutic effect of the anticancer drug is given by its ability to kill cancer cells and/or to induce the opioid receptor expression on the cancer cells.

There are two ways to look at the results of cancer treatment. One common way is the measurement of cell death (increasing data means more cells are dead). The other way is to measure the viability of cells (decreasing data means that less living cells are present or have lost their proliferation potential).

As used in the context of the present invention the words "treat," "treating" or "treatment" refer to using the combination of the present invention or any composition comprising them to either prophylactically prevent a cancer, or to mitigate, ameliorate or stop cancer. They encompass either curing or healing as well as mitigation, remission or prevention, unless otherwise explicitly mentioned. Also, as used herein, the word "patient" refers to a mammal, including a human.

According to the invention the treatment specifically refers to the inhibition of cancer cell proliferation and/or growth. This activity can include e.g. cytostatic or cytotoxic activity as well arresting growth of cells and/or tumours. Cancer cell proliferation is the result of the inhibition of cell division. In particular opioid receptor agonists induce cell death in tumours. Cell death in the context of the invention includes all types of cells death. This can include necrotic as well as apoptotic cell death or autophagy. In one embodiment of the invention the cell death is induced by the activation of the caspases-dependent or caspases-independent pathway. However, opioid receptor agonists can induce cell death via various pathways. In a preferred embodiment of the invention, opioid receptor agonists induce apoptosis in cancer cells.

As used herein, the term "cancer" which is synonymously used to the term "neoplasm" refers to diseases in which abnormal cells divide without control and are able to invade other tissues. Cancer cells can spread to other parts of the body through the blood and lymph systems.

- The terms "conventional therapy" and "conventional therapy regimen" in the context of the present invention are defined as the treatment programs (concerning dose, iteration-time and duration) which are recommended as therapeutic guidelines of associations, federations like Deutsche Krebshilfe, Deutsche Krebsgesellschaft, National Cancer Institute (NCI), National Comprehensive Cancer Network (NCCN) and respective health or cancer organizations which could be private, non-governmental or federal organizations. This also includes the treatment programs for a (preferably single) anticancer agent as prescribed by the manufacturer or distributor of the anticancer agent which are disclosed in the respective instruction leaflets of the anticancer agents.

The term "conventional therapy time" in the context of the present invention is defined as the time in a conventional therapy where an anticancer agent is applied to a patient without an opioid receptor agonist according the invention.

The therapy time starts with the first application of the anticancer agent, and may include iteration-periods which are specific for cancer and anticancer agent (for example application of a dose two times a day for a week than a pause of three weeks and then again application of a dose two times a day for a week followed by a pause of three weeks), up to time point, at which the anticancer agent is below the therapeutic plasma level of the patient. Cancer and its different types in the context of the present invention can be classified by the ICD-O Standard which is a specialised classification of the ICD-10 Standard Classes C00-C97 and D00-D36. Alternatively, the classification of Boecker et al. 2008 in chapter 6 (Pathologie, Elsevier, Urban & Fischer, p 167-218) can be used.

In a further embodiment of the invention said opioid receptor agonist is capable of inhibiting cell proliferation.

In one embodiment of the invention said anticancer agent and said opioid receptor agonist are administered simultaneously or successively.

In a preferred embodiment of the invention the periods of the therapeutically effective plasma levels of the opioid receptor agonist and the anticancer agent, respectively overlap predominantly.

In a further preferred embodiment of the invention the period of the therapeutically effective plasma levels of the anticancer agent is completely within the respective period of the opioid receptor agonist.

When administering two or more anticancer agents the respective period for which a partial, predominant or complete overlap is claimed, is given by the combined periods of the two or more anticancer agents.

In a further embodiment of the invention the opioid receptor agonist is given in a way that the patient develops a habituation against said opioid receptor agonist. It is thus preferable to wait with the anticancer treatment until the habituation period has begun or even reaches a plateau. The habituation can be a result of a decreased drug efficacy and/or a decrease in side effects such as respiratory depression. Side effects of opioid receptor agonist are hypotension, respiratory depression, vomiting, constipation, dizziness, sedation, euphoria and cardiac effects. This side effects have to be taken in account for determine the therapy scheme with the opioid receptor agonist and the cancer agent. This means that the opioid receptor agonist is given at a starting dose on a very low level i.e. 1% of the therapeutic dose and then increasing the dose depending to the guidelines of the opioid receptor agonist known by a skilled person and published by the manufacture or distributor of the opioid receptor agonist in an adequate time up to the therapeutic level which is required for the combination of anticancer agent and opioid receptor agonist.

In a preferred embodiment of the invention the administration regimen and thus the period within a therapeutically effective plasma level of the anticancer agent is defined by the conventional therapy regimen.

In a further aspect of the invention the patient treated with the combination according to the invention has received a pre-treatment comprising an anticancer agent.

In a more preferred embodiment the pre-treatment with the anticancer agent has been discontinued or even terminated.

In a further preferred embodiment the pre-treatment has been terminated due to resistance against the anticancer treatment.

In a preferred embodiment of the invention the period with a therapeutically effective plasma level of the anticancer agent lasts for at least 1 day, preferably 3 days, and more preferably for at least 5 days.

In one embodiment of the invention the period with a therapeutically effective plasma level for the opioid receptor agonist is at least two weeks, more preferably four weeks and even more preferably represents a chronic treatment.

Within the context of the present invention the term "chronic treatment" is defined as a opioid receptor agonist treatment with an administration period above four weeks, which preferably lasts over several months. In a further embodiment this chronic treatment differs from the conventional therapy regimen as prescribed or known to the person skilled in art. or is published in therapeutic guidelines of associations or federations like Deutsche Krebshilfe or Deutsche Krebsgesellschaft; NCCN, NCI or similar health or cancer organizations or the guidelines of producer or distributer of drugs which are used for treatment of cancer Within the context of the present invention the use of at least one anticancer agent refers to the use of one or more anticancer agents to be given in combination with the opioid receptor agonist according the invention. Thus, the combination includes the use of one, two, three, four, five or even more anticancer agents.

Generally, it is known, that apoptosis can be induced via two main biochemical pathways. The "death receptor pathway" (or extrinsic pathway) includes the TNF-receptor-induced (tumour necrosis factor) model and the Fas-receptor-induced model (the Fas-receptor is also known as Apo-1 or CD95). Bindings to these receptors result in the formation of death-inducing signalling pathways in the cell, including the activation of caspase-8. The "mitochondrial pathway" (or intrinsic pathway) involves the release of cytochrome c from mitochondria, binding of Apaf-1 and activation of procaspase-9. Several regulators are known to activate or deactivate the apoptosis pathways, such as the pro-apoptotic proteins Bax and Bak or the anti-apoptotic proteins Bcl-2, Bcl-$_{XL}$ or XIAP.

In one embodiment of the invention the opioid receptor agonists induce apoptosis by cleavage of caspase-3 and poly(ADP-ribose) polymerase (PARP) in the tumour cell, and/or cleavage of caspase-9 and down regulation of X-linked inhibitor of apoptosis protein (XIAP), and/or down regulation of the B-cell lymphoma-extra large protein (Bcl-$_{XL}$).

According to a preferred embodiment of the invention, the opioid receptor agonist is a member of the methadone group, comprising D-/L-methadone, levomethadone, levacetylmethadol and piritramide.

In the context of the present invention the term "methadone group" relates to opioids which are derivatives of 3,3-diphenylpropylamine. These compounds possess the 3,3-diphenylamine core structure as shown by the following formula (I):

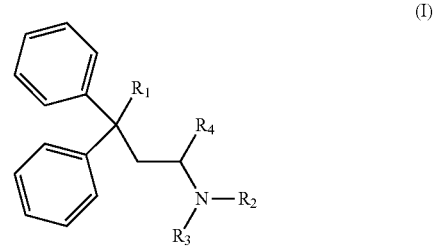

(I)

wherein R$_1$ is an aliphatic ketone, a 3-acetoxypropyl residue, a cyano group, or a 1-pyrrolidino-methylketone, —(C═O) C$_2$H$_5$, R$_2$ and R$_3$ are CH$_3$ or together forming a heterocyle, preferably a morpholino group, and R$_4$ is H or an alkyl residue, being preferably CH$_3$.

A non-limited list of examples for compounds of the methadone group includes methadone, normethadone, dextromoramide, isomethadone, acetylmethadol, alphacetylmethadol, levoacetylmethadol, premethadone, racemoramid, phenadoxone, dextropropoxyphene, dipipanone, benzitramide, piritramide, loperamide, themalon (which represents a 3,3-dithiophenylpropylamine) and levomoramid.

All these opioids can be used as salts. The racemic form of D-/L-methadone is preferably provided in form of a hydrochloride. In a preferred embodiment of the invention, the opioid methadone induces apoptosis in cancer cells via the mitochondrial pathway.

In on embodiment of the invention the opioid receptor agonist is selected from the list consisting of compounds of the methadone group such as D/L-methadone, D-methadone, L-methadone, normethadone, fentanyl derivatives such as fentanyl, sufentanyl, lofenantil, alfentanil, remifentanil, ohmefentanyl and carfentanyl; morphinane compounds such as morphine, codeine, heroine, dextrallorphane, dextromethorphan, dextrophanol, dimemorfan, levalorphanol, butorphanol, levofurethylnormorphanol, levomethorphane, levophenacylmorphane, levorphanol, methorphane, morphanol, oxilorphan, phenomorphan, and xorphanol, benzomorphane derivatives such as 5,9-DEHB, alazocine, anazocine, bremazocine, butinazocine, carbazocine, cogazocine, cyclazocine, dezocine, eptazocine, etazocine, ethylketocyclazocine, fluorophen, gemazocine, ibazocine, ketazocine, ketocyclazozine, metazocine, moxazocine, pentazocine, phenazocine, quadazocine, thiazocine, tonazocine, volazocine and 8-CAC; endogenous opioids such as endorphins (which can be alpha-, beta-, gamma- or delta-endorphins), enkephalins such as Met-enkephalin, Leu-enkephalin and methorphamid, dynorphins such as dynorphin A, dynorphin B or alpha-neoendorphin, nociceptin, dermorphins, morphiceptin, beta-caomorphine-5, DALAMID, DADLE, DADL DSLT, DSLET, DTLET, DAGO, DAMGO, DALCE, DAMME, DALDA, DPDPE, FK 33-824, [D-Met2, Pro5]enkephalin-amide, biphalin, and endomorphines such as endomoprhin-1 and endomoprhin-2; furthermore all fragments derived from the protein proopiomelanocortin (POMC) such as beta-lipotropin, beta-LPH-[61-64], beta-LPH-[61-65]-NH$_2$, (Met(O)65)-beta-LPH-[61-65], beta-LPH-[61-69], and beta-LPH-[61-69]; 4-phenylpiperidine derivatives such as pethidine, ketobemidone, anileridine, piminodine, phenoperidine, furethidine, alpha-prodin, trimeperidine, including 4-phenylpyrrolidine derivatives such as profadol and 4-phenylazepanderivates such as meptazinol; cyclohexane derivatives such as tilidine, U-50488, tramadol and tapentadol.

In a preferred embodiment of the invention the opioid receptor agonists of the invention are capable of inhibiting cell proliferation.

In a further embodiment of the invention the opioid receptor agonist is combined with at least one additional opioid receptor agonist. As a result the combination of the invention consists of two, three, four or more opioid receptor agonists. Preferably a combination of two different opioid receptor agonists is used. It could be demonstrated that the combined use of different opioids leads to a synergistic pro-apoptotic effect on cancer cells (see Example 38 and FIG. 56).

In a preferred embodiment said combination of opioid receptor agonists comprises morphine and fentanyl. Preferably said combination consists of morphine and fentanyl. The synergistic effect of morphine and fentanyl was e.g. shown for the leukemia cell line HL60 (see Example 38 and FIG. 56).

In a preferred embodiment the methadone, preferably the D,L-methadone and most preferably the hydrochloride form of D,L-methadone is given to the patient in particular to yield a plasma level which is between 0.05 μg/mL and 3 μg/mL.

In a further preferred embodiment the methadone, preferably the D,L-methadone and most preferably the hydrochloride form of D,L-methadone is given to the patient in particular to yield a plasma level which is between 0.01 μg/mL and 3 μg/mL.

In one embodiment of the invention the anticancer agent is selected from the list consisting of intercalating substances such as anthracycline doxorubicin, idarubicin, epirubicin, and daunorubicin; topoisomerase inhibitors such as irinotecan, topotecan, camptothecin, lamellarin D, etoposide, teniposide, mitoxantrone, amsacrine, ellipticines and aurintricarboxylic acid; nitrosourea compounds such as carmustine (BCNU), lomustine (CCNU), streptozocin; nitrogen mustards such as cyclophosphamide, mechlorethamine, uramustine, bendamustine, melphalan, chlorambucil, mafosfamide, trofosfamid and ifosfamide; alkyl sulfonates such as busulfan and treosulfan; alkylating agents such as procarbazin, dacarbazin, temozolomid and thiotepa; platinum analogues such as cisplatin, carboplatin, nedaplatin, oxaliplatin, satraplatin, and triplatin tetranitrate; microtubule disruptive drugs such as vinblastine, colcemid and nocodazole; antifolates like methotrexate, aminopterin, dichloromethotrexat, pemetrexed, raltitrexed and pralatrexate; purine analogues like azathioprine, mercaptopurine, thioguanine, fludarabine, fludarabine phosphate, pentostatin and cladribine; pyrimidine analogues like 5-fluorouracil, floxuridine, cytarabine, 6-azauracil, gemcitabine, capecitabine; taxane and taxane analogues like paclitaxel and docetaxel; steroid hormones like gestagene, androgene, glucocorticoids, dexamethasone, prednisolone, and prednisone; anti-cancer peptides including radioactively labeled paptides and peptide-drug conjugates; anti-cancer antibodies including radioactively-labelled antibodies and antibody-drug conjugates such as bevacizumab, cetuximab, panitumumab, rituximab, ipilimumab, alemtuzumab, ofatumumab, gemtuzumab-ozogamicin, brentuximab vedotin, $^{90}$Y-ibritumomab tiuxetan, $^{131}$I-tositumomab, or trastuzumab, alpha, beta or gamma irradiation; including particle radiation.

The above listed anticancer agents comprise also modifications such as PEGylation and formulations such as the use of liposomes (i.e. PEGylated liposomal doxorubicin).

In a further embodiment the anticancer agent can be a radioactively labeled chemical compound, peptide, protein or monoclonal antibody, wherein the radioactive label could emit alpha, beta or gamma rays and also ionizing particles.

In a preferred embodiment of the invention the anticancer agent is methotrexate, cytarabine, gemcitabine, paclitaxel, docetaxel, carboplatin, oxaliplatin, etoposide, vincristine, fludarabine especially cisplatin, doxorubicin, anthracycline, idarubicin, daunorubicin, epirubicin, or alpha-, beta-, or gamma irradiation.

When treating a cancer entity for which an induction of the opioid receptor is desired the patient is preferably treated with an anticancer agent selected from the group consisting doxorubicin, idarubicin, epirubicin, daunorubicin, carboplatin, oxaliplatin, cisplatin, etoposide, methotrexate, cytarabine, teniposide, gemcitabine, paclitaxel, rituximab and trastuzumab.

In one embodiment of the invention the patient who is treated with the combination of the invention suffers from a neoplasm as classified according the International statistical classification of Diseases and related health problems $10^{th}$ Revision (ICD-10), wherein the neoplasm is from the group consisting of malignant neoplasms of classes C00 to C97, in situ neoplasms of classes D00 to D09, benign neoplasms of classes D10 to D36, and neoplasms of uncertain or unknown behaviour of classes D37 to D48.

The classes are defined as follows: (C00) Malignant neoplasm of lip, (C01) Malignant neoplasm of base of tongue, (C02) Malignant neoplasm of other and unspecified parts of tongue, (C03) Malignant neoplasm of gum, (C04) Malignant neoplasm of floor of mouth, (C05) Malignant neoplasm of palate, (C06) Malignant neoplasm of other and unspecified parts of mouth, (C07) Malignant neoplasm of parotid gland, (C08) Malignant neoplasm of other and unspecified major salivary glands, (C09) Malignant neoplasm of tonsil, (C10) Malignant neoplasm of oropharynx, (C11) Malignant neoplasm of nasopharynx, (C12) Malignant neoplasm of piriform sinus, (C13) Malignant neoplasm of hypopharynx, (C14) Malignant neoplasm of other and ill-defined sites in the lip, oral cavity and pharynx, (C15) Malignant neoplasm of esophagus, (C16) Malignant neoplasm of stomach, (C17) Malignant neoplasms of small intestine, (C18) Malignant neoplasm of colon, (C19) Malignant neoplasm of rectosigmoid junction, (C20) Malignant neoplasm of rectum, (C21) Malignant neoplasms of anus and anal canal, (C22) Malignant neoplasms of liver and intrahepatic bile ducts, (C23) Malignant neoplasm of gallbladder, (C24) Malignant neoplasm of other and unspecified parts of biliary tract, (C25) Malignant neoplasm of pancreas, (C26) Malignant neoplasms of other and ill-defined Digestive Organs, (C30) Malignant neoplasm of nasal cavity and middle ear, (C31) Malignant neoplasm of accessory sinuses, (C32) Malignant neoplasm of larynx, (C33) Malignant neoplasm of trachea, (C34) Malignant neoplasm of bronchus and lung, (C37) Malignant neoplasm of thymus, (C38) Malignant neoplasm of heart, mediastinum and pleura, (C39) Malignant neoplasms of other and ill-defined sites in respiratory system and intrathoracic organs, (C40-C41) Malignant neoplasms, bone and articular cartilage, (C43) Malignant melanoma of Skin, (C44) Other malignant neoplasms of skin, (C45) Mesothelioma, (C46) Kaposi's Sarcoma, (C47) Malignant neoplasm of peripheral nerves and autonomic nervous system, (C48) Malignant neoplasm of retroperitoneum and peritoneum, (C49) Malignant neoplasm of other connective and soft tissue, (C50) Malignant neoplasm of breast, (C51) Malignant neoplasm of vulva, (C52) Malignant neoplasm of vagina, (C53) Malignant neoplasm of cervix uteri, (C54) Malignant neoplasm of corpus uteri, (C55) Malignant neoplasm of uterus, part unspecified, (C56) Malignant neoplasm of ovary, (C57) Malignant neoplasms of other and unspecified female and genital organs, (C58) Malignant neoplasm of placenta, (C60) Malignant neoplasm of penis, (C61) Malignant neoplasm of prostate, (C62) Malignant neoplasm of testis, (C63) Malignant neoplasm of other and unspecified male genital organs, (C64) Malignant neoplasm of kidney, except renal pelvis, (C65) Malignant neoplasm of renal pelvis, C66) Malignant neoplasm of ureter, (C67) Malignant neoplasm of bladder, (C68) Malignant neoplasm of other and unspecified urinary organs, (C69) Malignant neoplasms of eye and adnexa, (C70) Malignant neoplasm of meninges, (C71) Malignant neoplasm of brain, (C72) Malignant neoplasm of spinal cord, cranial nerves and other parts of central nervous system, (C73) Malignant neoplasm of thyroid gland, (C74) Malignant neoplasm of adrenal gland, (C75) Malignant neoplasm of other endocrine glands and related structures, (C76) Malignant neoplasm of other and ill-defined sites, (C77) Secondary and unspecified malignant neoplasm of lymph nodes, (C78) Secondary malignant neoplasm of respiratory and digestive organs, (C79) Secondary malignant neoplasm of other sites, (C80) Malignant neoplasm without specification of site, (C81) Hodgkin's Disease, (C82) Follicular non-Hodgkin's lymphoma (nodular), (C83) Diffuse non-Hodgkin's lymphoma, (C84) Peripheral and cutaneous T-cell lymphomas, (C85) Other and unspecified types of non-Hodgkin's lymphoma, (C88) Malignant immunoproliferative diseases, (C90) Multiple myeloma and malignant plasma cell neoplasms, (C91) Lymphoid leukemia, (C92) Myeloid leukemia, (C93) Monocytic leukemia, (C94) Other leukemias of specified cell type, (C95) Leukemia of unspecified cell type, (C96) Other and unspecified malignant neoplasms of lymphoid, haematopoietic and related tissue, (C97) Malignant neoplasms of independent (primary) multiple sites, (D00) Carcinoma in situ of oral cavity, oesophagus and stomach, (D01) Carcinoma in situ of other and unspecified digestive organs, (D02) Carcinoma in situ of middle ear and respiratory system, (D03) Melanoma in situ, (D04) Carcinoma in situ of skin, (D05) Carcinoma in situ of breast, (D06) Carcinoma in situ of cervix uteri, (D07) Carcinoma in situ of other and unspecified genital organs, (D09) Carcinoma in situ of other and unspecified sites, (D10) Benign neoplasm of mouth and pharynx, (D11) Benign neoplasm of major salivary glands, (D12) Benign neoplasm of colon, rectum, anus and anal canal, (D13) Benign neoplasm of other and ill-defined parts of digestive system, (D14) Benign neoplasm of middle ear and respiratory system, (D15) Benign neoplasm of other and unspecified intrathoracic organs, (D16) Benign neoplasm of bone and articular cartilage, (D17) Benign lipomatous neoplasm, (D18) Haemangioma and lymphangioma, any site, (D19) Benign neoplasm of mesothelial tissue, (D20) Benign neoplasm of soft tissue of retroperitoneum and peritoneum, (D21) Other benign neoplasms of connective and other soft tissue, (D22) Melanocytic naevi, (D23) Other benign neoplasms of skin, (D24) Benign neoplasm of breast, (D25) Leiomyoma of uterus, (D26) Other benign neoplasms of uterus, (D27) Benign neoplasm of ovary, (D28) Benign neoplasm of other and unspecified female genital organs, (D29) Benign neoplasm of male genital organs, (D30) Benign neoplasm of urinary organs, (D31) Benign neoplasm of eye and adnexa, (D32) Benign neoplasm of meninges, (D33) Benign neoplasm of brain and other parts of central nervous system, (D34) Benign neoplasm of thyroid gland, (D35) Benign neoplasm of other and unspecified endocrine glands, (D36) Benign neoplasm of other and unspecified sites, (D37) Neoplasm of uncertain or unknown behaviour of oral cavity and digestive organs, (D38) Neoplasm of uncertain or unknown behaviour of middle ear and respiratory and intrathoracic organs, (D39) Neoplasm of uncertain or unknown behaviour of female genital organs, (D40) Neoplasm of uncertain or unknown behaviour of male genital organs, (D41) Neoplasm of uncertain or unknown behaviour of urinary organs, (D42) Neoplasm of uncertain or unknown behaviour of meninges, (D43) Neoplasm of uncertain or unknown behaviour of brain and central nervous system, (D44) Neoplasm of uncertain or unknown behaviour of endocrine glands, (D45) Polycythaemia vera, (D46) myelodysplastic syndromes, (D47) Other neoplasms of uncertain or unknown behaviour of lymphoid, haematopoietic and related tissue, (D48) Neoplasm of uncertain or unknown behaviour of other and unspecified sites.

In a specific embodiment of the invention the patient who is treated with the combination of the invention suffers from metastases.

In a preferred embodiment of the invention the patient who is treated with the combination of the invention suffers from a neoplasm selected from list of classes consisting of C25, C50, C56, C71, C91, and C92.

In a more preferred embodiment the patient suffers from a neoplasm selected from the list comprising of acute lymphoblastic leukemia (C91.0), B-cell chronic lymphatic leukemia (C 91.2), acute promyelocytic leukemia (C92.4), acute myeloid leukemia (C92.0) chronic myeloid leukemia (C92.1), all forms of glioblastoma (C71), all forms of pancreatic cancer (C25), all forms of ovarian cancer (C56), classes of breast cancer (C50) and tumour stem cells such as glioblastoma initiating stem cells.

In a further embodiment of the invention the patient suffers from a breast cancer resistant to HER2-targeted therapies, like e.g. a Trastuzumab resistant breast cancer.

In a preferred embodiment the patient suffering from acute lymphoblastic leukemia (C91.0) is treated with the combination according the invention including an anticancer agent selected from the list consisting of methotrexate, cytarabine, carboplatin, oxaliplatin, vincristine, fludarabine, being preferably cisplatin, anthracycline doxorubicin, idarubicin, daunorubicin, epirubicin, etoposide, gemcitabine, paclitaxel, docetaxel or alpha, beta or gamma irradiation.

In a further preferred embodiment the patient suffering from acute lymphoblastic leukemia (C91.0) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from acute lymphoblastic leukemia (C91.0) is treated with the combination comprising D,L-methadone and etoposide or D,L-methadone and doxorubicin.

In a preferred embodiment the patient suffering from B-cell chronic lymphatic leukemia (C 91.2) is treated with the combination according the invention including an anticancer agent selected from the list consisting of methotrexate, cytarabine, carboplatin, oxaliplatin, vincristine, fludarabine, being preferably cisplatin, anthracycline doxorubicin, idarubicin, daunorubicin, epirubicin, etoposide, gemcitabine, paclitaxel, docetaxel or alpha, beta or gamma irradiation.

In a further preferred embodiment the patient suffering from B-cell chronic lymphatic leukemia (C 91.2) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from B-cell chronic lymphatic leukemia (C 91.2) is treated with the combination comprising D,L-methadone and fludarabine, or buprenorphine and fludarabine or fentanyl and fludarabine or morphine and fludarabine.

In a preferred embodiment the patient suffering from acute promyelocytic leukemia (C92.4) is treated with the combination according the invention including an anticancer agent selected from the list consisting of methotrexate, cytarabine, carboplatin, oxaliplatin, vincristine, fludarabine, being preferably cisplatin, anthracycline, doxorubicin, idarubicin, daunorubicin, epirubicin, etoposide, gemcitabine, paclitaxel, docetaxel or alpha, beta or gamma irradiation.

In a further preferred embodiment the patient suffering from acute promyelocytic leukemia (C92.4) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from acute promyelocytic leukemia (C92.4) is treated with the combination comprising D,L-methadone and doxorubicin or buprenorphine and doxorubicin or fentanyl and doxorubicin or morphine and doxorubicin.

In a preferred embodiment the patient suffering from acute myeloid leukemia (C92.0) is treated with the combination according the invention including an anticancer agent selected from the list consisting of methotrexate, cytarabine, carboplatin, oxaliplatin, vincristine, fludarabine, being preferably cisplatin, anthracycline, doxorubicin, idarubicin, daunorubicin, epirubicin, etoposide gemcitabine, paclitaxel, docetaxel or alpha, beta or gamma irradiation.

In a further preferred embodiment the patient suffering from acute myeloid leukemia (C92.0) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from acute myeloid leukemia (C92.0) is treated with the combination comprising D,L-methadone and doxorubicin or buprenorphine and doxorubicin or fentanyl and doxorubicin or morphine and doxorubicin.

In a preferred embodiment the patient suffering from chronic myeloid leukemia (C92.1) is treated with the combination according the invention including an anticancer agent selected from the list consisting of methotrexate, cytarabine, carboplatin, oxaliplatin, vincristine, fludarabine, being preferably cisplatin, anthracycline doxorubicin, idarubicin, daunorubicin, epirubicin, etoposide, gemcitabine, paclitaxel, docetaxel or alpha, beta or gamma irradiation.

In a further preferred embodiment the patient suffering from chronic myeloid leukemia (C92.1) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from chronic myeloid leukemia (C92.1) is treated with the combination comprising D,L-methadone and imatinib or buprenorphine and imatinib or fentanyl and imatinib or morphine and imatinib.

In another preferred embodiment of the invention the patient suffering from chronic myeloid leukemia (C92.1) is treated with the combination comprising D,L-methadone and fludarabine or buprenorphine and fludarabine or fentanyl and fludarabine or morphine and fludarabine.

In a further embodiment of the invention the patient suffering from leukemia is treated with at least one further opioid receptor agonist in addition to the combination of the invention. Hence, the patient is treated with at least two opioid receptor agonists. This strategy is based on the finding that the combination of different opioids shows a synergistic pro-apoptotic effect on cancer cell lines (see FIG. 56).

In a preferred embodiment the combination of the invention comprises morphine, fentanyl and at least one anticancer agent and in a further embodiment the combination consists of morphine, fentanyl and a further anticancer agent. The synergistic effect of morphine and fentanyl was e.g. shown for the leukemia cell line HL60 (see Example 38).

In a preferred embodiment the patient suffering from glioblastoma (C71) is treated with the combination according the invention including an anticancer agent selected from the list consisting of methotrexate, cytarabine, carboplatin, oxaliplatin, vincristine, fludarabine, being preferably cisplatin, temozolomide, anthracycline, doxorubicin, idarubicin, daunorubicin, epirubicin, etoposide, gemcitabine, paclitaxel, docetaxel, or alpha, beta or gamma irradiation.

In a further preferred embodiment the patient suffering from glioblastoma (C71) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from glioblastoma (C71) is treated with the combination comprising D,L-methadone and doxorubicin.

In a preferred embodiment said doxorubicin is given in a formulation that enhances the transfer of the doxorubicin across the blood brain barrier, For the skilled person there are several formulation strategies available to enable or enhance BBB transfer. As an example, the doxorubicin could be packed into liposomes or bound to transferrin.

In another preferred embodiment of the invention the patient suffering from glioblastoma (C71) is treated with the combination comprising D,L-methadone and daunorubicin, with a combination comprising D,L-methadone and idarubicin, or with a combination comprising D,L-methadone and temozolomide.

In a preferred embodiment the patient suffering from glioblastoma initiating stem cells are treated with the combination according the invention including an anticancer agent selected from the list consisting of methotrexate, cytarabine, carboplatin, oxaliplatin, vincristine, fludarabine, being preferably cisplatin, anthracycline, doxorubicin, idarubicin, daunorubicin, epirubicin, etoposide, gemcitabine, paclitaxel, docetaxel or alpha, beta or gamma irradiation.

In a further preferred embodiment the patient suffering from glioblastoma initiating stem cells are treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from glioblastoma initiating stem cells are treated with the combination comprising D,L-methadone and doxorubicin.

In a preferred embodiment the patient suffering from pancreatic cancer (C25) is treated with the combination according the invention including an anticancer agent selected from the list consisting of methotrexate, cytarabine, carboplatin, oxaliplatin, vincristine, fludarabine, being preferably cisplatin, oxaliplatin, anthracycline doxorubicin, idarubicin, daunorubicin, epirubicin, etoposide, gemcitabine, paclitaxel, docetaxel or alpha, beta or gamma irradiation.

In a further preferred embodiment the patient suffering from pancreatic cancer (C25) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from pancreatic cancer (C25) is treated with the combination comprising D,L-methadone and cisplatin.

In a further preferred embodiment of the invention the patient suffering from pancreatic cancer (C25) is treated with the combination comprising D,L-methadone and oxaliplatin.

In one embodiment of the invention the patient suffering from cancer is treated with a combination comprising D,L-methadone and temozolomide.

In a preferred embodiment the patient suffering from ovarian cancer (C56) is treated with the combination according the invention including an anticancer agent selected from the list consisting of methotrexate, cytarabine, carboplatin, oxaliplatin, vincristine, fludarabine, being preferably cisplatin, carboplatin, anthracycline doxorubicin, idarubicin, daunorubicin, epirubicin, etoposide, gemcitabine, paclitaxel, docetaxel or alpha, beta or gamma irradiation.

In a further preferred embodiment the patient suffering from ovarian cancer (C56) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from ovarian cancer (C56) is treated with the combination comprising D,L-methadone and cisplatin.

In another embodiment, the patient who is treated with the combination of D,L-methadone and cisplatin suffers from a cisplatin resistant ovarian cancer.

In a preferred embodiment the patient suffering from breast cancer (C50) is treated with the combination according the invention including an anticancer agent selected from the list consisting of methotrexate, cytarabine, carboplatin, oxaliplatin, vincristine, fludarabine, being preferably cisplatin, anthracycline doxorubicin, idarubicin, daunorubicin, epirubicin, etoposide, gemcitabine, paclitaxel, docetaxel or alpha, beta or gamma irradiation.

In a further preferred embodiment the patient suffering from breast cancer (C50) is treated with the combination according the invention including an opioid receptor agonist selected from the list consisting of D,L-methadone, buprenorphine, fentanyl, and morphine, being preferably D,L-methadone.

In an even more preferred embodiment of the invention the patient suffering from breast cancer (C50) is treated with the combination comprising D,L-methadone and cisplatin.

In a further preferred embodiment of the invention the patient suffering from breast cancer (C50), which preferably is a breast cancer resistant to HER2 targeted therapies, such as Trastuzumab resistant breast cancer, is treated with the combination comprising D,L-methadone and doxorubicin.

In another embodiment of the invention the patient suffering from prostate cancer (C62) is treated with the combination comprising D,L-methadone and cisplatin.

In one embodiment of the invention the patient suffering from leukemia is treated with a combination of D,L-methadone and one of the following anticancer agents: etoposide, cytarabine, methotrexate, cyclophosphamide, thioguanine, gemcitabine, paclitaxel, docetaxel or vincristine.

In another embodiment the cancer to be treated is a neoplasm according the International classification of Diseases for Oncology ICD-O in the actual version ICD-O-3 from 2000. Alternatively, the cancer to be treated is a cancer as included in the TNM Classification of Malignant Tumours (TNM), which represents a cancer staging system that describes the extent of cancer in a patient's body. In a further alternative, the cancer to be treated is disclosed by Boecker et al., 2008 in chapter 6 (Pathologie, Elsevier, Urban & Fischer, p. 167-218), which is incorporated by reference in its entirety.

In a preferred embodiment of the invention the patient that is treated with said combination suffers from non-solid tumours from the group consisting of leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, Ewing's sarcoma, veticulum cell sarcoma, myeloma, giant cell tumour, small-cell lung tumour, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglioneuromas, hyperplastic corneal nerve tumour, marfanoid habitus tumour, Wilms' tumour, seminoma, ovarian tumour, leiomyomata, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforme, leukemia, lymphomas, malignant melanomas, and epidermoid carcinomas.

In a further preferred embodiment of the invention the patient to be treated suffers from a neoplasm selected from the group consisting of pancreatic carcinoma, hepatoblastoma, colon carcinoma, (small cell lung cancer, melanoma, mamma carcinoma, ovarian carcinoma, prostate carcinoma, glioblastoma, acute lymphoblastic leukemia, acute myeloid leukemia, chronic myeloid leukemia, chronic lymphocytic leukemia, pro-forms of leukemia, hairy cell leukemia, Hodgkin's disease, Non-Hodgkin lymphoma, lymphoma, tumour stem cells, glioblastoma-initiating stem cells and multiple myeloma.

In another embodiment of the invention the patient exhibits either an intrinsic or an acquired resistance.

Accordingly, in the context of the present invention a "resistance" can either be total or partly; in other words, the patients considered treatable according to the invention can exhibit a reduced sensitivity or even a full lack of sensitivity to conventional anticancer treatments. These patients can also be determined as "non-responders" or "poor-responders".

A further synonym for a "resistant" cancer or tumour is a "refractory" type of cancer, which can also be either completely or partly refractory. Intrinsic resistance can thus also be determined as a "primary refractory cancer". A particular form of refractory or resistant cancer cells are the so called "kinetically refractory cells"; a phenomenon known e.g. from leukemia cells, when the cells are at first killed, but reproduce fast that an effective treatment is hardly possible.

As used in the context of the present invention the term "conventional" treatment or therapy refers to the currently accepted and widely used therapeutic treatment of a certain type of cancer, based on the results of past researches and/or regulatory approval.

Conventional anticancer drugs include cytotoxic and cytostatic agents, which kill the cancer cells or reduce and/or stop their growth or proliferation. The modes of action of these anticancer drugs can vary; examples are antimetabolites (e.g. cytarabine, methotrexate, mercaptopurine or clofarabine), DNA cross-linking agents (e.g. cisplatin and its derivatives), DNA intercalating substances (e.g. doxorubicin), Topoisomerase poisons (e.g. etoposide), kinase inhibitors (e.g. cetuximab), steroids (e.g. dexamethasone) or mitotic inhibitors (e.g. vincristine). One example for a conventional anticancer treatment of leukemia is the administration of doxorubicin or rituximab.

The conventional radiotherapy can also include radiation therapy, which means the use of high-energy radiation from x-rays, alpha, beta and gamma rays, Auger electrons, Ultraviolet rays, neutrons, protons, and other sources to kill cancer cells and shrink tumours. Radiation may originate from an outside the body device (external-beam radiation therapy), or it may originate from radioactive sources placed in the body in the vicinity of the cancer cells (internal radiation therapy). Systemic radiation therapy uses a radioactive substance, such as a radiolabeled monoclonal antibody, that travels in the blood stream to the target tissue. Radio resistant cancer cells do not or only partly respond to these treatments.

As outlined in detail above, according to one embodiment of the invention the opioid receptor agonists are applied for overcoming or "breaking" the intrinsic or acquired resistance of cancer cells to conventional anticancer treatments and/or radiation treatment or apoptosis resistance. In one embodiment of the invention cancer cells considered treatable according to the invention express an opioid receptor, in particular the µ opioid receptor.

According to the invention, the terms "resistance", "radioresistance" or "chemoresistance" are defined as a reduced sensitivity of a cancer cell to at least one conventional cancer therapy, i.e. either an anticancer drug or radiotherapy. A patient suffering from such a cancer is determined as a "resistant" cancer patient. Since the resistance can be intrinsic or acquired the observed reduction in sensitivity is either compared to fully sensitive "normal" cancer cells, which are responsive to the therapeutically effective dosage of the applied anticancer drug and/or radiation compared to the original sensitivity upon therapy onset. In the later case the resistance manifests either in a diminished amount of tumour regression for the same dose (either of the radiation or the anticancer drug) or an increased dose which is necessary for an equal amount of tumour regression.

In another embodiment of the invention the patient exhibits one or more of the subsequent resistances: apoptosis resistance, multi-drug resistance, anticancer drug resistance, cytotoxic drug resistance, resistance to reactive oxygen species, resistance to DNA damaging agents, resistance to toxic antibodies, doxorubicin resistance, single or cross resistance, irradiation resistance (e.g. alpha, beta, gamma or Auger electrons).

In a particular embodiment the patient is resistant to one or more of the following drug substances: methotrexate, cytarabine, thioguanine cisplatin, oxaliplatin, etoposide, vincristine, paclitaxel, carboplatin, teniposide, dexamethasone, prednisolone, cyclophosphamide, diphosphamide, doxorubicin, epirubicin, daunorubicin, idarubicin, mercaptopurine, fludarabine, gemcitabine, temozolomide, anti-HER2, and anti-CD20.

In one embodiment of the invention the anticancer agent that is administered together with the opioid receptor agonist is given at a dose, which is equal than or lower than the recommended dose for the respective cancer. The recommended dose is given by a conventional cancer therapy without the administration of an opioid receptor agonist. Preferably, the respective dose of the anticancer agent from the perspective of the skilled person represents a suboptimal or sub therapeutic dose, which have the advantage for the patient to have less side effects. The main effect is that the uptake of the dose of the anticancer drug is increased in the cancer cells, while the plasma concentration is on the level of the conventional therapy. This has the effect that non responder to conventional therapy could be treated.

In a preferred embodiment of the invention the anticancer agent that is administered together with the opioid receptor agonist is given at a dose, which is 2 times lower, preferably 3, 5, 10, or 30 times lower and even more preferably 100 times lower than the recommended dose for the treatment of cancer using the anticancer agent only.

In a further preferred embodiment of the invention the anticancer agent that is administered together with the opioid receptor agonist is given at a dose, which is equal than or lower than the recommended dose for the respective cancer, wherein the period of effective plasma levels of the anticancer agent is completely within the period of effective plasma levels of the opioid receptor agonist. The recommended dose is given by a conventional cancer therapy without the administration of an opioid receptor agonist.

In a further preferred embodiment of the invention the opioid receptor agonist is D/L-methadone and the anticancer agents are methotrexate and dexamethasone.

In a further embodiment of the invention, the opioids or opioid receptor agonist can be used as a composite with at least one anticancer drug.

In the context of the present invention, the term "anti-Her2" denotes to any ligand that binds to and interacts with the gene product of the Her-2/Neu gene. This encompasses antibodies such as Trastuzumab (herceptin) or any organic compounds.

A "composite" within the context of the present invention relates to a pharmaceutical preparation comprising a therapeutically effective amount of any of the opioid receptor agonist (component A) as defined according to the invention and at least one further anticancer substance (component B). This "composite" can constitute a single composition or at least two compositions, which can be administered to the patients either concomitantly or subsequently. The above mentioned substances are preferably combined with methadone, more preferably with the hydrochloride form of D/L-methadone.

The composite of the invention can be advantageous for the effective treatment of cancer cells, since it can exhibit synergistic effects compared to the single compositions. In particular composite with methadone as component A and one of the agents as component B as follows is preferred: methotrexate, cytarabine, cisplatin, carboplatin, oxaliplatin, etoposide, vincristine, doxorubicin, idarubicin, epirubicin, daunorubicin, fludarabine. gemcitabine, paclitaxel, docetaxel, temozolomide, anti-CD20, anti-HER2. Moreover, combinatorial treatment also comprising irradiation treatments is possible.

A further preferred composite consists of methadone as component A and temozolomide as component B.

In a preferred embodiment of the invention opioids are used to treat either resistant or sensitive non-solid cancers, i.e. all haematological malignancies affecting blood, bone marrow and lymph nodes, including acute lymphoblastic leukemia, acute myeloid leukemia, chronic myeloid leukemia, chronic lymphocytic leukemia and all pro-forms of leukemia, hairy cell leukemia, Hodgkin's disease, Non-Hodgkin lymphoma, lymphoma and multiple myeloma.

In a further aspect the invention provides a method for the selection of a combination of an opioid receptor agonist and one or more anticancer drugs. This method comprises the following steps:
 (a) providing an vitro culture of cancer cells, cell lines or primary cells, preferably isolated from a cancer biopsy or from a liquid sample (such as e.g. blood, amniotic fluid, pleural fluid, peritoneal fluid, or cerebrospinal fluid);
 (b) optionally testing the cells from step (a) for expression of opioid receptors;
 (c) treating the cells from step (a) with an opioid agonist, or at least one anticancer drug or a combination thereof;
 (d) analysing the cells for cell death and/or expression of opioid receptors
 (e) selecting the opioid receptor/anticancer drug combination and preferably a dose for said combination based on the desired extent of cell death/viability or inhibiting proliferation; and/or
 (f) selecting the anticancer agent and preferably a dose for said anticancer agent which shows the desired extent of induction of opioid receptors.

The in vitro cultured cancer cells can be an immortalized cell line, xenografted cells, a secondary or a primary cancer cell line or primary cells. In a preferred embodiment the cell line and/or cells is derived from a cancer biopsy, in more preferred embodiment the biopsy or blood sampling or cerebrospinal fluid sampling or pleural fluid sampling or amniotic fluid sampling or peritoneal fluid sampling is taken from the patient to be treated with the combination according the invention. The cancer cell line can represent a homogenous cell line based only on one cancer cell type or a heterogeneous cancer cell line comprising of different cell types.

The analysis of the opioid receptor expression in step (b) can be performed by techniques which are known to the person skilled in art. A non-limiting list of examples include immunofluorescence using an antibody or antibody fragment directed against said opioid receptor, the immunoprecipitation of the opioid receptors, or the use of labelled opioid receptor ligands such as naloxone-fluorescein.

For the analysis of the cell viability and apoptosis in step (c) there are several techniques which are known to the person skilled in art. A non-limiting list of examples include (a) cytolysis or membrane leakage assays such as the lactate dehydrogenase assay, the propidium iodide assay, the Trypan blue assay, the 7-Aminoactinomycin D assay, (b) mitochondrial activity or caspase assays such as the Resazurin and Formazan (MTT/XTT) can assay for various stages in the apoptosis process that foreshadow cell death, (c) functional assays which in the case of red blood cells measure the cell deformability, osmotic fragility, haemolysis, ATP level, and haemoglobin content; (d) genomic and proteomic assays which include the analysis of the activation of stress pathways using DNA microarrays and protein chips.

In a further preferred embodiment the cell viability is measured by the propidium iodide assay and the apoptosis is measured by determination of hypodiploid DNA (subG1) and FSC/SSC analyses by flow cytometry.

In step (d) the cultured cells are preferably treated in parallel experiments comprising the use of the opioid alone, the anticancer agent alone and a combination of the two substances. In a further embodiment the potency of the effect is analysed by studying the dose dependency of the respective effect. In alternative experiments several anticancer agents can be combined to increase the anti-apoptotic effect or opioid receptor expression or to reduce the side effect profile. In a further embodiment the initial selection of the test compounds will depend on the characteristics of the tumour. Furthermore also the patient characteristics can be taken in consideration including the age, the sex, the body weight, co-morbidities, individual metabolic capabilities, allergies and incompatibilities, genetic predisposition, the course of the disease and the family history.

For the in vitro analysis the opioid receptor agonists as described above can be used for testing. Preferably, D,L-methadone, L-methadone, fentanyl, buprenorphine, morphine, codeine, oxycodone, tramadol and tapentadol are used.

In a preferred embodiment, an anti cancer agent is chosen which is well known to have an effect on the respective cancer cell type, cell line or cells.

When testing an anticancer agent alone, the cultured cells are analysed for opioid receptor expression prior anticancer treatment and after the anticancer treatment under conditions which allow a comparison of the opioid receptor expression levels. Said comparison allows to identify anticancer agents which increase the opioid receptor expression on the respective cancer cell.

The selection in step (e) prioritizes the drug combination and/or the respective doses in order to maximise the efficacy while retaining a side effect profile which is acceptable for the patient.

The selection in step (f) prioritizes an anticancer agent with regard to its ability to increase the opioid receptor expression on the cancer cell. As a consequence the anti-apoptotic effect of the opioid agonist, as well as the anti-apoptotic affect of the anticancer agent is maximised.

In the case that in step (c) the cell culture was treated with a combination of opioid receptor agonist and anticancer agent the prioritization of the combination which is used, is done under the aspect which combination of doses has the better lethal effect on the cells in culture. The combination with the highest lethal effect or if observable, the dose with a up to 10% less effect in lethality of cells compared to the combination with the highest lethal effect on cells in culture but with the lower dose of opioid-receptor agonist should be used. FIG. 2c for example shows that with doxorubicin in conventional therapeutical dose as described in the instruction leaflet a D,L-methadone dose of 0.1 µg/mL would be preferable.

In a further aspect the invention provides a method for selection of an opioid receptor agonist for the treatment of cancer comprising the following steps:
(a) providing an vitro culture of cancer cells, cell lines or primary cells, preferably isolated from a cancer biopsy or from a liquid sample (such as e.g. blood, amniotic fluid, pleural fluid, or peritoneal fluid or cerebrospinal fluid);
(b) optionally testing the cells from step (a) for expression of opioid receptors;
(c) treating the cells from step (a);
(d) analysing the cells for cell death/viability or inhibition of proliferation;
(e) selecting the opioid receptor/anticancer drug combination and preferably a dose for said combination based on the desired extent of cell death; and/or
(f) selecting the opioid receptor agonist and preferably a dose for said opioid receptor agonist which shows the desired extent of induction of cell death.

For this method the steps (a) to (d) can be performed by methods and strategies as described above.

The analysis of the opioid receptor expression allows a selection of cancer type which might be treated with an opioid receptor agonist. Due to the in vitro treatment with an opioid receptor agonist, the individual dose for the cancer in vivo treatment can be determined.

I. EXPERIMENTAL PROCEDURES

Drugs and Reagents

For the in vitro experiments, D,L-methadone hydrochloride (D,L-methadone) and doxorubicin were purchased from Sigma (Taufkirchen, Germany), naloxone from Fagron GmbH&Co. KG (Barsbüttel, Germany), and pertussis toxin (PTX) from Calbiochem (Nottingham, UK). Prior to each experiment these substances were freshly dissolved in sterile distilled water to ensure the constant quality of the preparations. 3-Isobutyl-1-methylxanthine (IBMX, Sigma) was freshly dissolved in 0.01 N NaOH.

For in vivo application, we used D,L-methadone (Methaddict, Hexal, Germany) as 5 mg tablets purchased from the local pharmacy. The tablets were pulverized and solubilized freshly before use in 10% Tween 80 in saline. Doxorubicin (Hexal) was purchased as injection solution (5 mg/ml) and diluted freshly with saline to the appropriate concentrations.

Cell Lines

The human B-cell leukemia (BCP-ALL) cell lines Tanoue, Reh and Nalm6 were obtained from the DSMZ (Braunschweig, Germany) and cultured in RPMI 1640 (Invitrogen) containing 10% heat inactivated FCS (Lonza, Verviers, Belgium), 1 mmol/L glutamine (Invitrogen), 1% penicillin/streptomycin (Invitrogen), 25 mmol/L HEPES (Biochrom) at 37° C., 95% air/5% $CO_2$. In experimental settings, the leukemia cells were seeded in a density of 10,000 cells/mL.

Testing Opioid Receptor Signaling

Stimulation of opioid receptors (OR) by agonists like D,L-methadone leads to an activation of the inhibitory $G_i$-protein. The $\alpha_i$-subunit inactivates adenylyl cyclase (AC) resulting in a reduction of cAMP levels within the cell which in turn leads to apoptosis which might be mediated by several different modulators. Also the $\beta_\gamma$-subunits of the $G_i$-protein modulate the activity of different effectors like the inhibition of $Ca^{2+}$- and the activation of $K^+$-channels. Naloxone as opioid receptor antagonist inhibits competitively opioid receptors. PTx (pertussis toxin) inactivates $G_i$-proteins and blocks downregulation of cAMP. IBMX (Isobutyl-1-methylxanthine) inhibits phosphodiesterase and increases cAMP levels.

Serum Concentrations of Methadone

Determination of methadone in serum samples was carried out after liquid/liquid extraction using a mass spectrometer equipped with a gas chromatograph (GC/MS). As internal standard $d_9$-methadone was added. The mass selective detector was operated in electron impact mode. Data were acquired in the selected-ion monitoring mode. The analytes were identified with the following masses m/z 294, 223, 72 (target ion) for methadone and m/z 303, 226, and 78 for $d_9$-methadone with a limit of detection of 0.8 ng/ml and a limit of quantification of 1.2 ng/ml.

Serum Concentrations of Doxorubicin

Determination of doxorubicin and its main metabolites in serum were performed as described previously (Hilger et al., 2005; Richly et al., 2006) Using this validated method, the quantification of doxorubicin, doxorubicinol, and 7-deoxy-doxorubicinolon was possible with a LLQ of 0.2 ng/ml.

Patient-Derived-ALL Xenografts

For in vivo use ALL-SCID6 model was chosen. Fragments from in vivo passaged tumours were transplanted at day zero subcutaneously to 32 male NOD/SCID/IL2rγ null (NSG) mice. After randomization oral treatment (by gavage) with D,L-methadone was initiated one day later and performed daily until the end of the experiment with increasing doses: $1^{st}$ week 20 mg/kg/d, $2^{nd}$ week 30 mg/kg/d, $3^{rd}$ week 40 mg/kg/d, $4^{th}$ week 60 mg/kg/d, $5^{th}$-$10^{th}$ week 2×60 mg/kg/inj. The dose adaptation was necessary to avoid toxic deaths because of an overdosage of D,L-methadone. The maximum tolerated dose of D,L-methadone in the employed mouse strain is 2×60 mg/kg/inj. At day 46, 53, 60 and 76 doxorubicin 3 mg/kg was administered i.v. Tumour size was measured twice weekly at two dimensions and tumour volumes were calculated according to the formula (length× $width^2$)/2. Mean tumour volumes and standard deviations were calculated per group. Treated to control values (T/C) in percent were calculated by relating mean tumour volumes of each group at each measurement day to the controls. Individual body weight was determined twice per week as parameter for tolerability and body weight changes in percent were calculated by relating the mean values of each group to the first measurement day.

Serum from D,L-methadone treated mice was taken 0.5, 1, 4 and 24 hours after last D,L-methadone treatment at day 76, respectively, and stored at −20° C. until the determination of methadone concentration. Mice were sacrificed at day 77 for ethical reasons.

For the in vitro investigations, cell suspensions of human xenograft-derived-ALL-cells from patients with T-cell (ALL-SCID6, ALL-SCID3), B-cell (ALL-SCID7) and B-cell precursor (BCP, pre-B-ALL-SCID) acute leukemia were gained and cultivated in vitro and were phenotypic and genotypic characterized as described (Borgmann et al., 2000). All animal experiments were approved by the local responsible authorities (LaGeSo Berlin) and performed according to the guidelines for animal welfare in oncological experiments (Workman et al. 2000).

Flow Cytometric Assay for Determination of Cell Surface Opioid-Receptors

Cells were washed in PBS supplemented with 1% FCS, centrifuged and resuspended in PBS/1% FCS containing naloxone-fluoresceine (0.05 mM, Invitrogen) (Hedin et al., 1997). After 30 min of incubation at RT, the cells were washed twice with PBS/1% FCS, centrifuged and resuspended in icecold PBS/1% FCS. Flowcytometry analysis was performed using FACSCalibur (BD, Heidelberg, Germany).

Induction of Apoptosis

ALL cells were treated with D,L-methadone (≤3 μg/mL therapeutic plasma concentration) alone or in addition to doxorubicin in 175 $cm^2$ flasks or 96-well plates. Further experiments were performed simultaneously after addition of 60 μg/mL naloxone, 200 μM IBMX or 200 ng/mL PTX. After different points in time, apoptosis rates were measured by flowcytometry (Carbonari et al., 1994; Nicoletti et al., 1991). To determine apoptosis, cells were lysed with Nicoletti-buffer containing sodium citrate (0.1%), Triton X-100 (0.1%) and propidium iodide (50 μg/mL) as described by Nicoletti (Nicoletti et al., 1991). Apoptotic cells were determined by hypodiploid DNA (subG1) or forward scatter/side scatter analysis (Carbonari et al., 1994). The percentage of specific apoptosis was calculated as follows: 100×[experimental dead cells (%)−spontaneous dead cells in medium (%)]/[100%−spontaneous dead cells in medium (%)]. The spontaneous dead cells were in the rage of 5 to 10% using cell lines. The viability of the untreated patient cells (spontaneous dead cells) was less than 35% at 24 h and 48 h.

General Caspase Inhibition by zVAD.fmk

For inhibition of apoptosis, leukemia cells were treated with the pancaspase inhibitor of caspases, zVAD.fmk (benzoylcarbonyl-Val-Ala-Asp-fluoromethylketone; Enzyme-Systems-Products, Dubli, USA) as described (Friesen et al., 2007). 500 zVAD.fmk was added to the cells 1 h before stimulation with D,L-methadone and doxorubicin. After different time points, the percentage of apoptotic cells was determined by FSC/SSC analysis via flowcytometry (Carbonari et al., 1994).

Western Blot Analysis

Western blot analyses were performed as described (Classen et al., 2003; Friesen et al., 2004). Whole cell lysates were immunodetected for PARP, caspase-3, caspase-9, caspase-2, XIAP, Bcl-$x_L$ and β-actin using rabbit-anti-PARP-polyclonal-antibody (1:5000, Roche), mouse-anti-caspase-2-monoclonal-antibody (1:1000, BD-Transduction-Laboratories, Heidelberg, Germany), anti-XIAP-monoclonal-antibody (1:1000, BD-Transduction-Laboratories), mouse-anti-caspase-3-monoclonal-antibody (1:1000, Cell-Signaling, Boston, Mass./USA), rabbit-anti-caspase-9-polyclonal-antibody (1:1000, Cell-Signaling) rabbit-anti-Bcl-$x_L$-polyclonal-antibody (1:1000, Santa-Cruz, Heidelberg, Germany) and mouse-anti-β-actin-monoclonal-antibody (1:5000, Sigma). As secondary antibodies peroxidase-conjugated-goat-anti-mouse IgG or peroxidase-conjugated-goat-anti-rabbit IgG (1:5000, Santa-Cruz) were used for the enhanced chemoluminescence system (ECL, Amersham-Pharmacia, Freiburg, Germany). Equal protein loading was controlled by β-actin detection.

Analysis of Doxorubicin Uptake and Efflux

For analysis of doxorubicin uptake, the BCP-leukemia cell line Tanoue was seeded in a density of 100,000 cells/mL in 175 $cm^2$ flasks and was either left untreated or incubated with 0.3 μg/mL doxorubicin or a combination of 0.3 μg/mL doxorubicin and 3 μg/mL D,L-methadone at 37° C./5% $CO_2$. After 24 h, cells were washed twice with ice-cold PBS/1% FCS. Relative doxorubicin uptake in cells was analyzed using flowcytometry.

For analysis of doxorubicin efflux, cells were washed to remove doxorubicin from medium after incubation for 24 h. Next, cells were incubated with fresh medium without doxorubicin or fresh medium containing 3 μg/mL D,L-methadone at 37° C./5% $CO_2$ without doxorubicin to measure doxorubicin efflux. After different time points cells were harvested, washed and relative doxorubicin content in leukemia cells was analyzed using flowcytometry.

II. EXAMPLES

Example 1

D,L-Methadone Induces Cell Death in Xenograft-Derived All-Cells Depending on Opioid Receptor Expression To show the clinical relevance of D,L-methadone in treatment of leukemia and the role of opioid receptor triggering in cell death induction, the anti-cancer effect of D,L-methadone was analyzed in different xenograft-derived ALL-cells. The xenografts were originally established from patients with T-cell (ALL-SCID6, ALL-SCID3), B-cell (ALL-SCID7) (Borgmann et al., 2000) and B-cell precursor (BCP, pre-B-ALL-SCID) acute leukemia. At first, the opioid-receptor expression on xenograft-derived-ALL-cells was measured. It was observed that the ALL-SCID6, ALL-SCID3 and the ALL-SCID7 leukemia cells displayed opioid-receptors in high amounts (FIG. 1A), whereas the pre-B-ALL-SCID expressed only moderate levels of opioid-receptors (FIG. 1A).

To analyze if cell death induction using D,L-methadone depends on the levels of opioid receptor expression, ALL-SCID6, ALL-SCID3, ALL-SCID7 and pre-B-ALL-SCID were treated with different concentrations of D,L-methadone (FIG. 1B).

Therapeutic plasma concentrations of D,L-methadone (3 µg/mL) were used but also a higher concentration of 10 µg/mL D,L-methadone was used, because levels of D,L-methadone in lymphatic tissue and marrow may be higher, but have not been measured (Singh et al., 2011). It was found that therapeutic plasma concentrations of D,L-methadone (3 µg/mL) induced a strong cell death in xenograft-derived ALL-cells expressing high amounts of opioid-receptors on their cell surface (FIG. 1A,B). In comparison to these observations, the pre-B-ALL-SCID having a moderate opioid-receptor level (FIG. 1A) could only be slightly killed with therapeutic concentrations of D,L-methadone (FIG. 1B). This clearly reveals that apoptosis induction by D,L-methadone is depend on the level of opioid-receptor expression.

Example 2

Combination Treatment with D,L-Methadone and Doxorubicin Kills and Activates Caspases in ALL-Cells with Moderate Opioid Receptor Expression In analogous studies, the cytotoxic potential of D,L-methadone on BCP-ALL-cell lines (Tanoue, Reh, Nalm6) expressing opioid-receptors in a moderate level on their cell surface (FIG. 2A) was tested.

These BCP-ALL-cell lines could only be killed slightly by D,L-methadone (FIG. 2b) as observed for the pre-B-ALL-SCID (FIG. 1B). In order to show if different substances will act synergistically, the cell lines Tanoue, Reh, Nalm6 and pre-B-ALL-SCID were treated with different concentrations of D,L-methadone and doxorubicin alone or in combination with each other (FIG. 2B, 2C). It was observed that the combination treatment strongly induced cell kill in BCP-ALL-cell lines as well as in xenograft-derived-BCP-ALL-patient-cells (pre-B-ALL-SCID) (FIG. 2B,C).

In order to analyze the molecular pathways of cell killing in more detail and to find out how the combination treatment with D,L-methadone and doxorubicin induced apoptosis, it was analyzed at first which effector molecules of apoptosis signaling are activated in BCP-ALL-cells upon this combination treatment compared to cells treated with D,L-methadone or doxorubicin alone. 120 h after treating the BCP-ALL-cell line Tanoue with D,L-methadone in addition to doxorubicin, the activation of the caspase cascade in BCP-ALL-cells was observed. The analysis revealed a strong activation of caspase-3, caspase-9, and caspase-2 and cleavage of the prototype substrate of caspase-3, poly-(ADP-ribose)-polymerase (PARP) (FIG. 3A).

The role of the caspase cascade in apoptosis induction was further investigated with the broad-spectrum inhibitor of caspases zVAD.fmk. BCP-ALL-cells were pre-incubated with or without 50 µM of zVAD.fmk and treated with D,L-methadone in addition to doxorubicin. zVAD.fmk strongly decreased cell death after combination treatment with D,L-methadone and doxorubicin in BCP-ALL-cells (FIG. 3B) underlining the dependence on caspases activation.

The apoptotic machinery is tightly controlled by anti-apoptotic factors like XIAP and Bcl-$x_L$ (Fulda, 2009a; Fulda, 2009b) which we found to be strongly downregulated in BCP-ALL-cells treated with D,L-methadone in addition to doxorubicin (FIG. 3C). These results indicate that the combination of D,L-methadone and doxorubicin sensitizes BCP-ALL-cells for apoptosis via the activation of caspases and downregulation of XIAP and Bcl-$x_L$.

Example 3

Doxorubicin Strongly Induces Opioid-Receptor Expression in Leukemia Cells

The efficiency of cell death induction and activation of effector molecules in apoptosis pathways after treating leukemia cells with D,L-methadone seems to depend on the amount of opioid-receptors displayed on the cell's surface. Combination treatment with D,L-methadone and doxorubicin profoundly kills leukemia cells with moderate opioid receptor expression, which could only be killed slightly by D,L-methadone or doxorubicin alone. Chemotherapeutics enhance the expression of receptors like CD95 in leukemia cells (Posovszky et al., 1999). To analyze whether doxorubicin might influence the opioid-receptor expression, the BCP-ALL-cell line Tanoue was treated with doxorubicin for 96 h. Afterwards, the relative amount of opioid-receptors compared to untreated cells was measured by flowcytometry. It was found that doxorubicin strongly increased opioid-receptor expression (FIG. 4A) suggesting that D,L-methadone can bind in higher amounts to cells co-treated with doxorubicin. This effect could presumably result in the higher cytotoxic potential of the combination treatment with D,L-methadone and doxorubicin.

Example 4

Opioids Like D,L-Methadone Enhances the Uptake of Doxorubicin and Inhibits Its Efflux Opioids are substrates of the in multi-drug resistances-involved efflux pump P-glycoprotein (P-gp). To analyze whether D,L-methadone might influence the uptake and/or efflux of doxorubicin in leukemia cells, the BCP-ALL-cell line Tanoue was incubated for different intervals with doxorubicin alone or with a combination of doxorubicin and D,L-methadone. After 24 h (0 h), an enhanced doxorubicin concentration in the cells co-incubated with doxorubicin and D,L-methadone (FIG. 4B) was observed. After removing doxorubicin from the supernatant, fresh medium was added without doxorubicin and D,L-methadone was applied. After 8 h and 24 h, D,L-methadone reduced the doxorubicin efflux strongly (FIG. 4B) indicating that D,L-methadone increases doxorubicin uptake and inhibits doxorubicin efflux out of leukemia cells. This explains how D,L-methadone as well as doxorubicin mutually increase their cytotoxic potential.

Example 5

Apoptosis Induction by D,L-Methadone and Doxorubicin Depends Critically on Opioid Receptor Activation and cAMP Concentration To further analyze the role of opioid-receptor triggering in apoptosis induction and consequently activation of apoptotic pathways, the BCP-ALL-cell line Tanoue was treated with D,L-methadone, doxorubicin or with the opioid-receptor antagonist naloxone alone or in different combinations with each other (FIG. 5A,B).

After 96 h it was found that blocking opioid-receptors by naloxone strongly reduced the apoptosis rates of the combination treatment with D,L-methadone and doxorubicin (FIG. 5A). In addition, opioid-receptor blocking by naloxone drastically reduced the activation of caspase-9, caspase-2 and caspase-3 and cleavage of PARP after treating BCP-ALL-cells with D,L-methadone in addition to doxorubicin (FIG. 5B). This indicates that opioid-receptor triggering is critically involved in apoptosis induction and in caspase activation (FIG. 7).

Opioid receptor stimulation activates inhibitory $G_i$-proteins which in turn block adenylyl cyclase activity reducing cAMP (FIG. 7). cAMP is an inhibitor of DNA-damage—as well as doxorubicin-induced apoptosis in leukemia cells (Naderi et al., 2009; Safa et al., 2010a). Pertussis toxin (PTX) inactivates $G_i$-proteins and blocks downregulation of cAMP (Law et al., 1985) (FIG. 7). IBMX however increases cAMP levels as a result of phosphodiesterase inhibition (FIG. 7). To analyze the critical role of cAMP in opioid receptor activation-induced apoptosis, the BCP-ALL-cell line Tanoue was treated with D,L-methadone, doxorubicin, and IBMX or PTX either alone or in different combinations with each other (FIG. 5C,D). After 96 h it was found that upregulation of cAMP by IBMX (FIG. 5C) and blocking downregulation of cAMP by PTX (FIG. 5D) strongly reduced the apoptosis rates of combination treatment with D,L-methadone and doxorubicin. In addition, the upregulation of cAMP by IBMX also decreased doxorubicin-induced apoptosis (FIG. 5C). These results indicate that the activation of opioid receptor coupled $G_i$-proteins is essential for the induction of apoptosis which might be regulated via the intracellular cAMP levels.

Example 6

D,L-Methadone Alone or in Addition to Doxorubicin Inhibits Tumour Growth In Vivo in an ALL-Xenograft-Model In vitro results demonstrated that D,L-methadone could induce apoptosis in several leukemia cell lines and increased the cytotoxicity of doxorubicin. To confirm the clinical relevance of the anti-cancer potential of D,L-methadone alone or in combination with doxorubicin and to verify the results obtained so far an ALL-xenograft study was undertaken.

For the in vivo study, a patient-derived-ALL-xenograft-model (ALL-SCID6) was used. Its phenotypic and genotypic identity with the original patient sample was proven (Borgmann et al., 2000). The experiment started at day 0 with subcutaneous inoculation of ALL-SCID6 fragments from an in vivo passage into male NOD/SCID/IL2ry null (NSG) mice. After randomization, D,L-methadone was orally administered starting at day one after ALL-inoculation with increasing doses. When tumours were palpable, doxorubicin treatment was initiated. D,L-methadone and doxorubicin treatment led to a significant inhibition of tumour growth at comparable levels (FIG. 6).

Combination treatment with D,L-methadone and doxorubicin had a similar anti-tumour efficacy as D,L-methadone or doxorubicin alone until day 70. At later time points, the tumour inhibition was longer lasting during the combined treatment of D,L-methadone and doxorubicin. The therapy was well-tolerated with body weight changes of −10% for the combination and −8% or −4% for the D,L-methadone or doxorubicin treatment, respectively. To analyze D,L-methadone serum concentrations in mice, 0.5, 1, 4 and 24 hours after the last D,L-methadone application, serum was taken and D,L-methadone quantified by mass spectrometry. The serum concentrations of methadone were found between 28 ng/mL and 138 ng/mL in the time course of 0.5 until 4 hours after D,L-methadone application indicating that levels comparable with the in vitro concentrations could be reached. The serum concentrations of doxorubicin were found between 156 ng/mL and 198 ng/mL. These results demonstrate that D,L-methadone and the co-treatment using doxorubicin and D,L-methadone significantly inhibited tumour growth in vivo.

Example 7

D,L-Methadone Sensitizes Glioblastoma Cells for Doxorubicin Treatment

As shown by flow cytometry, the glioblastoma cell lines A172 and U118MG (s. FIG. 8) as well as primary glioblastoma cells (s. FIG. 11A) and glioblastoma-initiating stem cells (s. FIG. 12A) express opioid receptors. In all these cells and cell lines the combination treatment of D,L-methadone and doxorubicin dose-dependently induces apoptosis (see FIGS. 9, 10, 11B and 12B). As exemplified for the glioblastoma cell line A172 it could be shown that cell death induction of glioma cells using D,L-methadone and doxorubicin cotreatment depends on caspase activation (s. FIG. 13). Furthermore, it could be shown that D,L-methadone reversed deficient activation of apoptosis pathways by doxorubicin in glioblastoma-initiating stem cells (s. FIG. 14).

Example 8

Effect of D,L-Methadone on Doxorubicin Uptake and Efflux

In vitro results using the glioblastoma cell line A172 demonstrated that D,L-methadone could enhance the uptake and also inhibit the efflux of doxorubicin (s. FIG. 15). This gives an explanation for the sensitization of cancer cell towards treatment with anticancer drugs.

Example 9

Effect of Doxorubicin or Cisplatin on Opioid Receptor Expression on Cancer Cells As shown for the glioblastoma cell line A172, doxorubicin leads to a 6-fold increase in opioid receptor expression (s. FIG. 16). It could be shown that this mechanism holds also true for other cancer types and anticancer drugs since in the promyelocytic leukemia cell line HL60, the cisplatin-treatment leads to a 2.1-fold increase in opioid receptor expression (s. FIG. 19).

Example 10

Sensitization of Leukemia, Pancreatic and Ovarian Cancer Cells for Treatment with Different Anticancer Agents In further in vitro analyses it could be demonstrated that D,L-methadone sensitizes leukemia cancer cells (Nalm-6), pancreatic cancer cells (Nalm6) and ovarian cancer cells (A2780) for etoposide or cisplatin treatment (s. FIG. 17). Furthermore, also chronic lymphocytic leukemia cells (CLL) could be sensitized by D,L-methadone for apoptotic treatment using Fludarabine (s. FIG. 18).

Example 11

Sensitization of Mamma Carcinoma Cells for Treatment with Different Anticancer Agents As shown by flow cytometry, the Her2/Neu-resistent mamma carcinoma cell line JIMT-1 expresses the µ-opioid receptor (s. FIG. 20). As shown by FACS analysis the combination treatment of D,L-methadone and doxorubicin dose-dependently induces apoptosis in JIMT-1 cells (see FIG. 21). It could be shown that cell death induction of JIMT-1 cells using D,L-methadone and doxorubicin cotreatment depends on caspase activation (s. FIGS. 22 and 23).

Example 12

Sensitization of Cancer Cells for Doxorubicin Treatment by the Opioid Fentanyl

As exemplified for the T-cell derived leukemia cell line CEM it could be shown that also the opioid fentanyl was able to sensitize the CEM cells for treatment using doxorubicin (s. FIG. 24). In a further in vitro experiment, the opioid buprenorphine sensitized leukemia cells (HL-60) for apoptosis due to doxorubicin (s. FIG. 25).

Example 13

Combination Treatment with D,L-Methadone and Cisplatin (CDDP) Kills and Activates Caspases in Different Leukemia Cells The cell death potential of D,L-methadone on different leukemia-cell lines was shown on human T cell leukemia, human acute myeloid leukemia, human B cell precursor leukemia, human B cell leukemia. All tested cell lines expressing opioid-receptors in a moderate level on their cell surface (FIG. 27).

These leukemia cells could only be killed slightly by D,L-methadone (FIG. 28, white bars). In order to show that different anticancer agents (substances) will act synergistically, human T cell leukemia, human acute myeloid leukemia, human B cell precursor leukemia and human B cell leukemia were treated with different concentrations of D,L-methadone (−CDDP) or cisplatin alone or with D,L-methadone in addition to cisplatin (+CDDP) (FIG. 28). The combination treatment strongly induced cell death in different leukemias depending on different concentrations of cisplatin or/and D,L-methadone.

The molecular pathways of cell killing was shown in more detail and it was shown how the combination treatment with an opioid receptor agonist i.e. D,L-methadone and an anticancer agent i.e. cisplatin induce apoptosis. First the effector molecules of apoptosis signaling was shown, that are activated in different leukemia cells (human T cell leukemia, human acute myeloid leukemia, human B cell precursor leukemia). Combination treatment of D,L methadone in combination with Cisplatin (+CDDP) was compared to cells treated with D,L-methadone (−CDDP) or cisplatin alone.

It was shown that treating the different leukemia cells with D,L-methadone in addition to cisplatin (+CDDP), the activation of the caspase cascade in leukemia cells was induced. A strong activation of caspase-3 (active caspase-3 p19, p17), caspase-9 (active caspase-9 p37), and caspase-2 and cleavage of the prototype substrate of caspase-3, poly-(ADP-ribose)-polymerase (PARP) (cleavage p85 and or a downregulation of PARP p116) was induced depending on the combination treatment (FIG. 29).

The role of the caspase cascade in apoptosis induction was further investigated with the broad-spectrum inhibitor of caspases zVAD.fmk. Different leukemia cells (human T cell leukemia, human acute myeloid leukemia, human B cell precursor leukemia) were pre-incubated with 500 of zVAD.fmk (+zVAD.fmk, white bars) or without zVAD.fmk (−zVAD.fmk, black bars) and treated with D,L-methadone in addition to cisplatin. zVAD.fmk strongly decreased cell death after combination treatment with D,L-methadone and cisplatin (FIG. 30) underlining the dependence on caspases activation.

The apoptotic machinery is tightly controlled by anti-apoptotic factors like XIAP and Bcl-xL and pro-apoptotic factors like Bax (Fulda, 2009a; Fulda, 2009b). XIAP was strongly downregulated (p57) and or cleaved (p30) in different leukemia cells treated with D,L-methadone in addition to cisplatin (+CDDP) (FIG. 29) depending on different concentrations of cisplatin or/and different concentration of D,L-methadone. A strong upregulation of Bax (p21) is induced in human T cell leukemia induced after treatment with D,L-methadone in addition to cisplatin (+CDDP). The combination of D,L-methadone and cisplatin sensitizes different leukemia cells for apoptosis via the activation of caspases and by downregulation and inhibition of anti-apoptotic factors such as XIAP and upregulation of pro-apoptotic factors such as Bax. So it shown that the opioid receptors are receptors which induce cell death and activate apoptosis pathways involving caspase activation, downregulation and or cleavage of PARP, and or downregulation of anti-apoptotic factors, and or upregulation of pro-apoptotic factors, and or downregulation and inhibition of inhibitory apoptotic proteins (IAP). Therefore the opioid receptors are a new unknown way with an new mechanism of inducing cell death, beside the common known cell death receptors/death inducing ligands systems and mechanisms like the CD95/CD95L-System.

Example 14

Cisplatin Strongly Induces Opioid-Receptor Expression in Leukemia Cells

The efficiency of cell death induction and activation of effector molecules in apoptosis pathways after treating leukemia cells with opioid-receptor-agonists i.e. D,L-methadone depend on the amount of opioid-receptors displayed on the cell's surface. Combination treatment with D,L-methadone and cisplatin profoundly kills leukemia cells with moderate opioid receptor expression, which could only be killed slightly by D,L-methadone or cisplatin alone. Chemotherapeutics enhance the expression of the receptor CD95 (FAS, APO-1) in leukemia cells which is a special known death receptor (Posovszky et al., 1999). To show that cisplatin has an influence to the opioid-receptor expression, the different leukemia cells (human T cell leukemia, human acute myeloid leukemia, human B cell precursor leukemia) were treated with cisplatin. Afterwards, the relative amount of opioid-receptors compared to untreated cells was measured by flowcytometry. It was shown that cisplatin strongly increased opioid-receptor expression (FIG. 31). Therefore opioid receptor-agonists like D,L-methadone can bind in higher amounts to cells, co-treated with cisplatin or other anticancer agents which are able to induce a higher level of expressed opioid receptors. This effect results in the higher cell death potential of the combination treatment of an opioid receptor agonist i.e D,L-methadone and an anticancer agent i.e. cisplatin.

It is shown in the invention that the opioid receptor agonist which has a longer minimal duration of effectiveness like D,L methadone has a better result than one, that has a shorter minimal duration of effectiveness like morphine compared to D,L methadone (FIG. 33 and FIG. 34.

Example 15

Apoptosis Induction by D,L-Methadone and Doxorubicin Depends Critically on Opioid Receptor Activation in Glioblastomas To show the role of opioid-receptor triggering in apoptosis induction in glioblastomas which is a solid tumour, glioblastoma cells were treated with D,L-methadone, doxorubicin or with the opioid-receptor antagonist naloxone alone or in different combinations with each other (FIG. 32).

After 120 h and 144 h it was shown that blocking opioid-receptors by naloxone strongly reduced the apoptosis rates of the combination treatment with D,L-methadone and doxorubicin (FIG. 32).

Example 16

Different Duration of Effectiveness of Different Opioids Induces Different Rates of Apoptosis Using D,L-Methadone or Morphine in Combination with Anticancer Drugs Such as Doxorubicin in Glioblastomas or in Leukemias The efficiency of cell death induction after treating glioblastoma cells or leukemia cells with opioids depends on the duration of effectiveness of the opioids. The minimal duration of effectiveness of methadone is 5-7 hours and the minimal duration of effectiveness of morphine is 2-4 hours. Combination treatment with D,L-methadone and doxorubicin strongly induced high cell death rates in glioblastoma cells (FIG. 33A) and leukemia cells (FIG. 34A). In contrast, combination treatment with morphine and doxorubicin induced lower cell death rates in glioblastoma cells (FIG. 33B) and leukemia cells (FIG. 34B). This indicates that the rates of induction of cell death after combination treatment of opioids with anticancer drugs depend also on the duration of effectiveness of opioids. The effect is found also at other anticancer agents.

Example 17

Combination Treatment Using D,L-methadone in Addition to Doxorubicin Mediated Cell Proliferation Inhibition and G2/M Cell Cycle Arrest in Glioblastoma Cells Cell proliferation is governed by the eukaryotic cell cycle (Sherr C J. Cancer cell cycles. Science 1996; 274:1672-7), which is regulated not only by growth factors but also by a variety of signals that act to inhibit cell cycle progression. Most of cancer cells have 4 cell division cycle stages: gap 1 (G1), synthesis (S), G2, and mitosis (M). Chromosomal DNA replicates during the S phase. As glioblastoma cells divide, the cell cycle should move from the S stage to the G2/M stage. This tightly controlled temporal order is imposed by the sequential activation of a number of protein kinases known as cyclin-dependent kinases (CDKs), by the formation of complexes with various cyclins. Opioid receptor agonist for example Methadone in combination with doxorubicin inhibits proliferation of cancer cells such as glioblastoma cells and induces S/G2-M cell cycle arrest in glioblastoma cells.

Example 18

Apoptosis Induction and Caspase Activation Depend on Opioid Receptor Activation Inducing cAMP Downregulation in Glioblastoma cAMP-related signaling can control apoptosis induction and cell growth. To analyze the role of opioid receptor activation in apoptosis induction and caspase activation in glioblastoma cells, glioblastoma cells A172 were treated with the opioid receptor agonist D,L-methadone, the anticancer agent doxorubicin or with the opioid receptor antagonist naloxone alone or in different combinations (FIGS. 36A, 36B and 36C). Blocking opioid receptors by naloxone strongly reduced apoptosis (FIGS. 36A and 36B) and activation of caspase-9, caspase-3 and cleavage of PARP (FIG. 36C) induced by combination treatment with D,L-methadone and doxorubicin. This indicates that opioid receptor activation plays a critical role in apoptosis induction and caspase activation. Opioid receptor stimulation activates inhibitory Gi-proteins which in turn block adenylyl cyclase activity reducing cAMP. IBMX, however, increases cAMP levels due to phosphodiesterase inhibition. To analyze the critical role of cAMP in opioid receptor activation-induced apoptosis, A172 cells were treated with D,L-methadone, doxorubicin, and IBMX either alone or in different combinations (FIG. 36D). Upregulation of cAMP by IBMX strongly reduced apoptosis induction by combination treatment with D,L-methadone and doxorubicin indicating that opioid receptor activation via cAMP downregulation sensitizes glioblastoma cells for doxorubicin-induced apoptosis and caspases activation.

Example 19

Opioid Receptor Activation Using D,L-Methadone Inhibits Tumour Growth In Vivo

U87MG glioblastoma cells were subcutaneously inoculated per nude-mouse. After randomization of 16 mice, D,L-methadone was daily orally administered in 8 mice starting at day 1 until the end of experiment. D,L-Methadone dosage was increased weekly from 60 to 120 to 240 mg/kg/d bid. At day 33, 24 h after the last treatment with D,L-methadone the mice were sacrificed. For analyzing serum concentrations of D,L-methadone in mice 0.5, 1 and 4 h after last D,L-methadone-application, serum was taken and D,L-methadone quantified by mass spectrometry. In comparison to vehicle treated mice of the control group, the D,L-methadone treated mice had a significantly reduced tumour size at day days 19 to 33 with an optimum T/C value of 49% (see FIG. 37). The D,L-methadone treatment was well tolerated in the dose used and induced only a minor body weight loss of 9%. Serum concentrations were found between 136 ng/ml and 1608 ng/mL of methadone in the time course of 0.5 to 4 h after D,L-methadone application. These findings demonstrate that opioid receptor activation using D,L-methadone inhibits growth of glioblastoma in vivo.

Example 20

Opioids Such as D,L-Methadone Increase Cisplatin-Induced Cell Death in Ovarian Cancer Cell After Short Term Treatment A2780 ovarian cancer cells were treated with cisplatin (5, 3 µg/mL) or D,L-methadone (3, 1 µg/mL) alone or in combination. As shown in FIG. 38, a strong induction of cell death was observed by co-treatment of D,L-methadone and cisplatin. This suggests that opioids such as D,L-methadone strongly potentiates cisplatin-induced apoptosis in ovarian cancer cells.

Example 21

Opioids Such as D,L-Methadone Increase Cisplatin-Induced Cell Death in Ovarian Cancer Cell After Long Term Treatment A2780 ovarian cancer cells were treated with cisplatin (2, 1, 0.5, 0.3 µg/mL) or D,L-methadone (10, 3, 1 µg/mL) alone or in combination. As shown in FIG. 39, a strong induction of cell death was observed by co-treatment of D,L-methadone and cisplatin. This suggests that opioids such as D,L-methadone strongly potentiates cisplatin-induced apoptosis in ovarian cancer cells and breaks chemoresistance.

Example 22

Opioids Such as D,L-Methadone Increase Cisplatin-Induced Cell Death in Cisplatin-Resistant Ovarian Cancer Cell A2780cis ovarian cancer cells were treated with cisplatin (3, 2, 1 µg/mL) or D,L-methadone (10, 3, 1 µg/mL) alone or in combination. As shown in FIG. 40, a strong induction of cell death was observed by co-treatment of D,L-methadone and cisplatin. This suggests that opioids such as D,L-methadone strongly potentiates cisplatin-induced apoptosis in cisplatin-resistant ovarian cancer cells.

Example 23

Opioids Such as D,L-Methadone Increase the Effectiveness of Cisplatin in Treatment of Ovarian Cancer Cell A2780 ovarian cancer cells were treated with cisplatin (2 µg/ml) alone. As shown in FIG. 41, cisplatin in a concentration of 2 µg/mL induced cell death of 90% after 144 h. However, treatment with 0.5 µg/mL cisplatin in addition to D,L-methadone (10, 3, 1 µg/mL) induced a cell death of 95%. Furthermore, treatment with 0.2 µg/mL cisplatin in addition to D,L-methadone (10, 3, 1 µg/mL) induced a cell death of between 70 and 85% depending on concentrations of D,L-methadone. This indicates that opioids such as D,L-methadone strongly potentiates cisplatin-induced apoptosis/cell death in ovarian cancer cells. D,L-methadone increases the effectiveness of cisplatin in treatment of ovarian cancer, suggesting that a strong reduction of anti-cancer drugs concentrations can be used by cotreatment with D,L-methadone to get comparable cell death rates and therefore less side effects of the anti-cancer drugs will be observed. Based on the present data, the anticancer agent can be given at a dose which it at least 2 or 3 times lower and up to 100 times lower than the recommended dose for the treatment of the respective cancer.

Example 24

Opioid Receptor Activation Reverses Deficient Caspase Activation by Cisplatin in Ovarian Cancer Cells Deficient caspase activation was observed in chemo- and radio resistant ovarian cancer cells treated with anticancer drugs or radiation. To clarify the involvement of caspases activation in combination therapy of D,L-methadone and cisplatin-induced apoptosis in ovarian cancer cells, A2780 ovarian cancer cells were treated with D,L-methadone (3, 1 µg/mL) or cisplatin (5, 3 µg/mL) alone or in combination. As shown in FIG. 42, the combination treatment using cisplatin and D,L-methadone leads to a strong caspase activation in ovarian cancer cells by activating caspase-3, caspase-9, and caspase-8 and cleavage of Poly-(ADP-ribose)-polymerase (PARP). This demonstrates that opioid receptor activation using D,L-methadone reverses deficient activation of caspases by cisplatin in ovarian carcinoma cells.

Example 25

Opioid Receptor Activation Using D,L-Methadone Plays a Critical Role in Sensitizing Breast Cancer Cells for Doxorubicin Treatment To analyze the role of opioid receptor activation in apoptosis induction in breast cancer, the Trastuzumab resistant breast cancer cells JIMT-1 were treated with the opioid receptor agonist D,L-methadone, doxorubicin or with the opioid receptor antagonist naloxone alone or in different combinations (FIG. 43). Blocking opioid receptors by naloxone strongly reduced apoptosis induced by combination treatment with D,L-methadone and doxorubicin. This indicates that opioid receptor activation plays a critical role in apoptosis induction.

Example 26

Opioids Such as D,L-Methadone Increase Cisplatin-Induced Cell Death in Prostate Cancer Cells Prostate cancer cells PC-3 were treated with cisplatin (5, 3 µg/mL) or D,L-methadone (10, 3, 1 µg/mL) alone or in combination. As shown in FIG. 44, a strong induction of cell death was observed by co-treatment of D,L-methadone and cisplatin. This suggests that opioids such as D,L-methadone strongly potentiates cisplatin-induced apoptosis in prostate cancer cells.

Example 27

Opioids Such as D,L-methadone Increase Cell Death Induction of Different Anti-Cancer Drugs from Different Anti-Cancer Drug Classes in Leukemia Cells Leukemia cells Nalm6 were treated with different anti-cancer drugs alone (white columns) or in combination with D,L-methadone (black columns). As shown in FIG. 45, a strong induction of cell death was observed by co-treatment of D,L-methadone and anti-cancer drugs (black columns). This suggests that opioids such as D,L-methadone strongly potentiates apoptosis induction of different anticancer drugs from different anticancer classes in leukemia cells.

Example 28

Opioids Such as D,L-Methadone Increase Anti-Cancer Drug-Induced Cell in Glioblastoma Cells Glioblastoma cells A172 were treated with different anti-cancer drugs from the same anti-cancer drug class such as anthracyclines (Doxorubicin, Idarubicin, and Daunorubicin). Glioblastoma cells were treated with anthracyclines alone (white columns) or in combination with D,L-methadone (black columns). As shown in FIG. 46, a strong induction of cell death was observed by co-treatment of D,L-methadone and different anthracyclines. This suggests that opioids such as D,L-methadone strongly potentiates apoptosis induction of different anti-cancer drugs from the same class in glioblastoma cells.

Example 29

Opioid Receptor Expression on Pancreatic Cancer Cells

Pancreatic cancer cells Colo 357 were stained with naloxone fluorescein measuring opioid receptor expression by flow cytometry. As a result a strong expression of opioid receptors on the surface of pancreatic cancer was found (see FIG. 47).

Example 30

Opioids Such as D,L-Methadone Increase Anti-Cancer Drug-Induced Cell in Pancreatic Cancer Cells Pancreatic cancer cells Colo 357 were treated with different anti-cancer drugs from the same anti-cancer drug class such as cisplatin metal complexes (oxaliplatin, cisplatin). Pancreatic cancer cells Colo 357 were treated with different concentration of cisplatin metal complexes, oxaliplatin or cisplatin alone or in combination with D,L-methadone. As shown in FIG. 48, a strong induction of cell death was observed by co-treatment of D,L-methadone and the platin metal complexes (A) oxaliplatin or (B) cisplatin. This suggests that opioids such as D,L-methadone strongly potentiates apoptosis induction of different anticancer drugs from the same anti-cancer drug class in pancreatic cancer cells.

Example 31

Opioid Receptor Activation Reverses Deficient Caspase Activation by Cisplatin and Oxaliplatin in Pancreatic Cancer Cells Deficient caspase activation was observed in chemo- and radioresistant pancreatic cancer cells Colo 357 treated with anti-cancer drugs or radiation. To clarify the involvement of caspases activation in combination therapy of D,L-methadone and cisplatin-induced apoptosis or D,L-methadone and oxaliplatin-induced apoptosis in pancreatic cancer, pancreatic cancer cells Colo 357 were treated with D,L-methadone (3, 1 µg/mL) or oxaliplatin (3, 2 µg/mL; see FIG. 49A) or cisplatin (0.5, 0.7 µg/mL; see FIG. 49 B) alone or in combination with methadone and oxaliplatin (see FIG. 49A) or cisplatin (see FIG. 49B). As shown in FIG. 49, the combination treatment leads to strong caspase activation in pancreatic cancer cells by activation of caspase-3, caspase-9, and cleavage of Poly-(ADP-ribose)-polymerase (PARP). This demonstrates that opioid receptor activation using D,L-methadone reverses deficient activation of caspases by cisplatin or oxaliplatin in pancreatic cancer cells.

Example 32

Inhibition of Caspases Activation Blocks Opioid-Sensitized Pancreatic Cancer Cells for Oxaliplatin- or Cisplatin-Induced Apoptosis To investigate the critical role of caspases in opioid receptor activation-induced apoptosis, pancreatic cancer cells Colo 357 were incubated with the broad spectrum inhibitor of caspases zVAD.fmk. Incubation with zVAD.fmk almost completely inhibited apoptosis in pancreatic cancer cells induced by D,L-methadone in addition to oxaliplatin (see FIG. 50 A,B) or by D,L-methadone in addition to cisplatin (see FIG. 50 C,D), suggesting that caspases are central for opioid receptor activation-mediated sensitization of pancreatic cancer cells for oxaliplatin and cisplatin treatment. This demonstrates that opioid receptor activation such as D,L-methadone reverses deficient activation of caspases by oxaliplatin or cisplatin in pancreatic cancer cells.

Example 33

Opioids Such as D,L-Methadone Increase Temozolomide (Temodal)—Induced Cell Death in Glioblastoma Cells Glioblastoma cells A172 were treated with temozolomide or D,L-methadone (3, 1 µg/mL) alone or in combination. As shown in FIG. 51, a strong induction of cell death was observed by co-treatment of D,L-methadone and temozolomide. This suggests that opioids such as D,L-methadone strongly potentiates temozolomide-induced apoptosis in glioblastoma cells.

Example 34

Opioids Such as D,L-Methadone Increase the Effectiveness of Oxaliplatin and Cisplatin in Pancreatic Cancer Treatment Pancreatic cancer cells Colo 357 were treated with different concentrations of oxaliplatin (A) or cisplatin (B) alone or in combination with D,L-methadone (hatched columns, white columns). As shown in FIG. 52, a strong induction of cell death was observed by co-treatment of D,L-methadone and different cisplatin metal complexes oxaliplatin (A) or cisplatin (B).

Pancreatic cancer cells Colo357 were treated with (A) oxaliplatin (10 µg/ml) alone. 10 µg/mL cisplatin induced cell death of 60% after 120 h. However, treatment with 3 µg/mL oxaliplatin in addition to D,L-methadone (10, 3, 1 µg/mL) induced a cell death of 65%. In addition, treatment with 2 µg/mL oxaliplatin in addition to D,L-methadone (10, 3, 1 µg/mL) induced a cell death of 45%.

Pancreatic cancer cells Colo 357 were treated with (B) cisplatin (10 µg/ml) alone. 10 µg/mL cisplatin induced cell death of 70% after 144 h. However, treatment with 0.7 µg/mL cisplatin in addition to D,L-methadone (10, 3, 1 µg/mL) induced a cell death of 85%. In addition, treatment with 0.5 µg/mL cisplatin in addition to D,L-methadone (10, 3, 1 µg/mL) induced a cell death of 60%.

This suggests that D,L-methadone increases the effectiveness of cisplatin or oxaliplatin in treatment of pancreatic cancer, suggesting that a strong reduction of anti-cancer drugs concentrations can be used by cotreatment with D,L-methadone to get comparable cell death rates and therefore less side effects of the anti-cancer drugs will be observed. In addition, this demonstrates that opioids such as D,L-methadone breaks chemoresistance because conventional therapies using anti-cancer drugs are limited by the toxicity of anti-cancer drugs concentrations used for patients treatment.

Example 35

Opioids Such as D,L-Methadone Increase the Effectiveness of Doxorubicin in Leukemia Treatment BCP-ALL cell lines (Nalm6, Reh and Tanoue) were treated with doxorubicin alone or in combination with D,L-methadone and doxorubicin (hatched columns). As shown in FIG. 53, a strong induction of cell death was observed by co-treatment using D,L-methadone. This suggests that D,L-methadone increases the effectiveness of doxorubicin in treatment of leukemia cells, suggesting that a strong reduction of anti-cancer drugs concentrations can be used by cotreatment with D,L-methadone to get comparable cell death rates and therefore less side effects of the anti-cancer drugs will be observed.

Example 36

Opioids Such as D,L-Methadone Increase the Effectiveness of Doxorubicin in Breast Cancer Treatment Trastuzumab resistant breast cancer cells (JIMT-1) were treated with doxorubicin alone or in combination with D,L-methadone and doxorubicin (hatched columns). As shown in FIG. 54, a strong induction of cell death was observed by co-treatment of D,L-methadone. 0.1 µg/mL doxorubicin induced cell death of 70% after 120 h. However, treatment with 0.015 µg/mL doxorubicin in addition to D,L-methadone (10, 3, 1, 0.1 µg/mL) induced a cell death between 70 and 55% depending on D,L-methadone concentration.

This suggests that D,L-methadone increases the effectiveness of doxorubicin in treatment of breast cancer cells, suggesting that a strong reduction of anti-cancer drugs concentrations can be used by cotreatment with D,L-methadone to get comparable cell death rates and therefore less side effects of the anti-cancer drugs will be observed.

Example 37

Opioids Such as D,L-Methadone Increase the Effectiveness of Doxorubicin in Glioblastoma Treatment Glioblastoma cells A172 were treated with different concentrations of doxorubicin alone or in combination with D,L-methadone (hatched columns, white columns). As shown in FIG. 55, a strong induction of cell death was observed by co-treatment of D,L-methadone and doxorubicin.

Glioblastoma cells A172 were treated with doxorubicin (1 µg/ml) alone. 1 µg/mL doxorubicin induced cell death of 80% after 144 h. However, treatment with 0.1 µg/mL doxorubicin in addition to D,L-methadone (10, 3, 1 µg/mL) induced a cell death of 85%-50% depending on concentrations of D,L-methadone.

This suggests that D,L-methadone increases the effectiveness of doxorubicin in treatment of glioblastoma, suggesting that a strong reduction of anti-cancer drugs concentrations can be used by cotreatment with D,L-methadone to get comparable cell death rates and therefore less side effects of the anti-cancer drugs will be observed. In addition, this demonstrates that opioids such as D,L-methadone breaks chemoresistance because conventional therapies using anti-cancer drugs are limited by the toxicity of anti-cancer drugs concentrations used for patients treatment.

Example 38

Combination Treatment of Different Opioids Shows a Synergistic Effect for Induction of Cell Death in Leukemia Cells Leukemia cells HL60 were treated with fentanyl (3, 1 µg/mL) alone (A) or morphine (3, 1 µg/mL) alone (A) or in combination of fentanyl and morphine (B) at concentrations as indicated. As shown in FIG. 56, a strong synergistically increased induction of cell death was observed by co-treatment of morphine and fentanyl (B). This suggests that the combination of different opioids enhances the pro-apoptotic effect and argues for a combined use of opioids also in the combination with a further anticancer agent.

Discussion

The examples provide evidence that D,L-methadone induces apoptosis, activates caspases and increases doxorubicin-induced cell death in leukemia cells depending on opioid-receptor activation inducing the downregulation of cAMP. In addition, it could be demonstrated for the first time, that D,L-methadone can strongly reduce tumour growth of ALL in a xenograft-model in vivo. Noticeably, this tumour-killing effect could be enhanced by the combination of D,L-methadone with the anticancer drug doxorubicin.

Methadone is a µ-opioid receptor agonist binding to µ-opioid receptors if presented on cells. It was found that D,L-methadone kills strongly xenograft-derived ALL-cells expressing high levels of opioid receptors. In contrast, D,L-methadone induces cell death only slightly in xenograft-derived ALL-cells and -cell lines expressing moderate opioid receptor amounts indicating that D,L-methadone-induced apoptosis seems to depend on critical levels of opioid receptor expression in leukemia cells.

Combination treatment may prove to be advantageous in malignancies that still partially respond to either treatment alone as different therapeutics are known to interact with each other amplifying weaker death signals. Combination treatment with D,L-methadone and doxorubicin enhances the anti-tumour efficacy of both agents synergistically in BCP-ALL-cells expressing moderate levels of opioid-receptors and increases strongly caspase activation playing a critical role in apoptosis induction in sensitive and resistant cancer cells (Fulda, 2009c). In addition, the downregulation of the anti-apoptotic proteins XIAP and Bcl-$x_L$ involved in the occurrence of resistances in many malignancies like ALL or NHL (Addeo et al., 2005) is markedly enhanced. This suggests that combination treatment of D,L-methadone and doxorubicin strongly increases apoptosis induction and could improve their anti-tumour efficacy synergistically.

Resistance to conventional chemotherapeutic drugs is a limiting factor in the effectiveness of therapies whereby multidrug resistances as a result of the overexpression of drug transporters such as P-gp are also well-characterized. While in healthy cells the P-gp expression belongs to the normal cellular defense system, in human cancer cells the overexpression of P-gp correlates with decreased survival and poor outcome (Diestra et al., 2003). D,L-methadone could be shown to be a substrate of P-gp inhibiting its action (Crettol et al., 2007). As shown herewith, co-treatment of doxorubicin with D,L-methadone enhances doxorubicin cell-uptake and furthermore inhibits doxorubicin-efflux out of leukemia cells, suggesting that D,L-methadone sensitizes leukemia cells for doxorubicin-induced apoptosis by increasing concentrations of doxorubicin within the cells.

Combination treatment using D,L-methadone and doxorubicin induced apoptosis and caspase activation in BCP-ALL-cells expressing moderate amounts of opioid-receptors on their surface. The enhanced toxicity of this combination treatment was found to be additionally associated with an increased expression of opioid-receptors after doxorubicin treatment. Therefore, D,L-methadone can bind in higher amounts to cells co-treated with doxorubicin. These results indicate that the enhanced toxicity in the combination treatment with D,L-methadone and doxorubicin is associated with the upregulation of opioid-receptor expression mediated by doxorubicin and furthermore with an increased uptake and decreased efflux of doxorubicin mediated by D,L-methadone. Both agents can hence exert their cytotoxic potential to a higher extent.

Opioid receptors signal by catalysing ligand-dependent nucleotide exchange on $G_i$, thereby inhibiting adenylyl cyclase and modulating N-type calcium channels as well as G protein-gated inwardly rectifying potassium (GIRK)-type potassium channels leading to changes in cell signalling (FIG. 7). Dependence of apoptosis induction on opioid-receptor triggering is underlined by their inhibition. Blocking opioid-receptor signaling with the opioid receptor antagonist naloxone inhibited combination treatment with D,L-methadone and doxorubicin-induced apoptosis and caspase activation in a high rate, suggesting that opioid-receptor triggering by D,L-methadone is involved in apoptosis induction and caspase activation (FIG. 7). Based on this mechanism of action every opioid receptor agonist independent of the individual opioid receptor should kill tumour cells by apoptosis since all opioid receptors are linked to the adenylyl cyclase via the $G_i$ pathway.

Further experiments prove the general applicability of the above described combination therapy:

Broad spectrum of cancers. Several diverse cancer types can be treated with the combination of opioid receptor agonists such as e.g. breast cancer, pancreatic cancer, prostate cancer, ovarian cancer, glioblastoma or leukemia.

Broad spectrum of opioids. In accordance with the Gi-associated mechanism of action, several structurally and pharmacologically distinct opioids like D,L-methadone, buprenorphine and fentanyl could sensitize the cancer cells for anticancer drugs.

Broad spectrum of anticancer drugs. For several structurally and pharmacologically distinct anticancer drugs it could be shown that they increase opioid receptor expression and show increased influx/decreased efflux due to the co-applied opioid agonist.

Summary

It has to be emphasized that the interaction between opioids and anticancer agents represents a self-reinforcing feedback loop as illustrated by FIG. 26. In the first path of this loop opioids enhance the cellular uptake and inhibit the efflux of anticancer drugs. On the second path of said loop the accumulating anticancer drugs lead to an increased expression of opioid receptors. Hence, both agents can exert their cytotoxic potential to a higher extent.

The present examples could verify the clinical relevance with patient-derived ALL-cells, patient-derived glioblastoma cells and glioblastoma initiating stem cells ex vivo and could show for the first time that D,L-methadone as monotherapy or in combination with doxorubicin leads to a strong tumour growth inhibition in a patient-derived leukemia model and in a glioblastoma xenograft model. The anti-leukemic efficacy, the tumour growth inhibition of glioblastoma and the side effects of D,L-methadone alone or in combination with doxorubicin were comparable with those of doxorubicin alone. However, only the combination treatment was able to achieve a longer lasting growth inhibition. The serum concentrations of methadone in mice correlated with the concentrations showing in vitro cytotoxicity.

In sum, a combination therapy of opioids and anticancer drugs could improve the cancer therapies in several ways:

Due to the upregulation of opioid receptors, former opioid insensitive cancer types could be subjected to an opioid therapy.

Due to the opioid-induced intracellular accumulation of anticancer drugs the efficacy of the treatment is enhanced.

Due to inhibition of anti-apoptotic proteins such as Bcl-$X_L$ and inhibition of inhibitory apoptotic proteins such as XIAP This could lead to therapy of cancer types which are difficult to treat.

Furthermore, this might allow a dose reduction for the anticancer drugs enhancing the safety and patient compliance of the chemotherapy.

Finally, also resistant cancer cells could be re-sensitized for an anticancer treatment.

In addition, the numerous opioids and numerous anticancer drugs on the market open up the way for new drug combinations which might represent improved treatment due to increased efficacy and/or safety.

(B) ALL-SCID6, ALL-SCID3, ALL-SCID7 and pre-B-ALL-SCID were treated with different concentrations of D,L-methadone (as indicated). After 24 h and 48 h, the percentages of apoptotic cells were measured by FSC/SSC-analysis. The percentage of specific apoptosis was calculated as follows: 100×[experimental dead cells (%)–spontaneous dead cells in medium (%)]/[100%–spontaneous dead cells in medium (%)]. Columns, mean of triplicates; bars, SD<10%.

Figure 2:
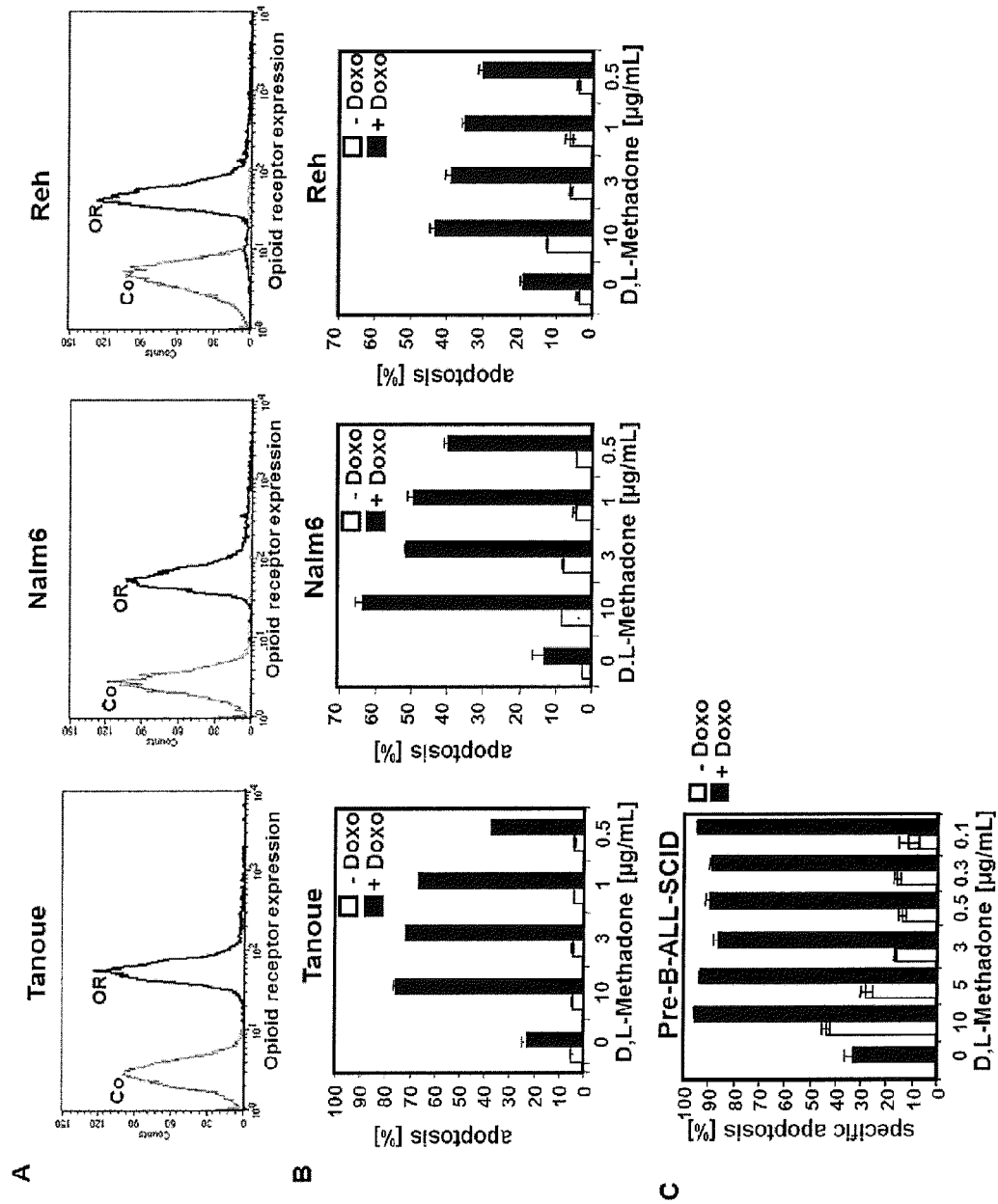

FIG. 2: Combination treatment with D,L-methadone and doxorubicin induces apoptosis in ALL-cells expressing moderate amounts of opioid receptors (A) Different BCP-ALL-cell lines (Tanoue, Nalm6 and Reh) express a moderate number of opioid-receptors on their cell surface. Tanoue, Nalm6 and Reh were stained with naloxone-fluoresceine measuring opioid-receptor expression (OR, thick black curve) and analyzed by flowcytometry. Controls (Co) are exhibited as thin black curves.

(B) BCP-ALL-cell lines (Tanoue, Nalm6 and Reh) were treated with different concentrations of D,L-methadone (as indicated) alone (–Doxo, white columns), with doxorubicin alone or with D,L-methadone (as indicated) in addition to doxorubicin (+Doxo, black columns). For the cell line Tanoue, we used doxorubicin in a concentration of 0.06 µg/mL, for Nalm6 and Reh a concentration of 0.01 µg/mL. 120 h after stimulation, percentages of apoptotic cells were measured by hypodiploid DNA analysis.

Figure 1:
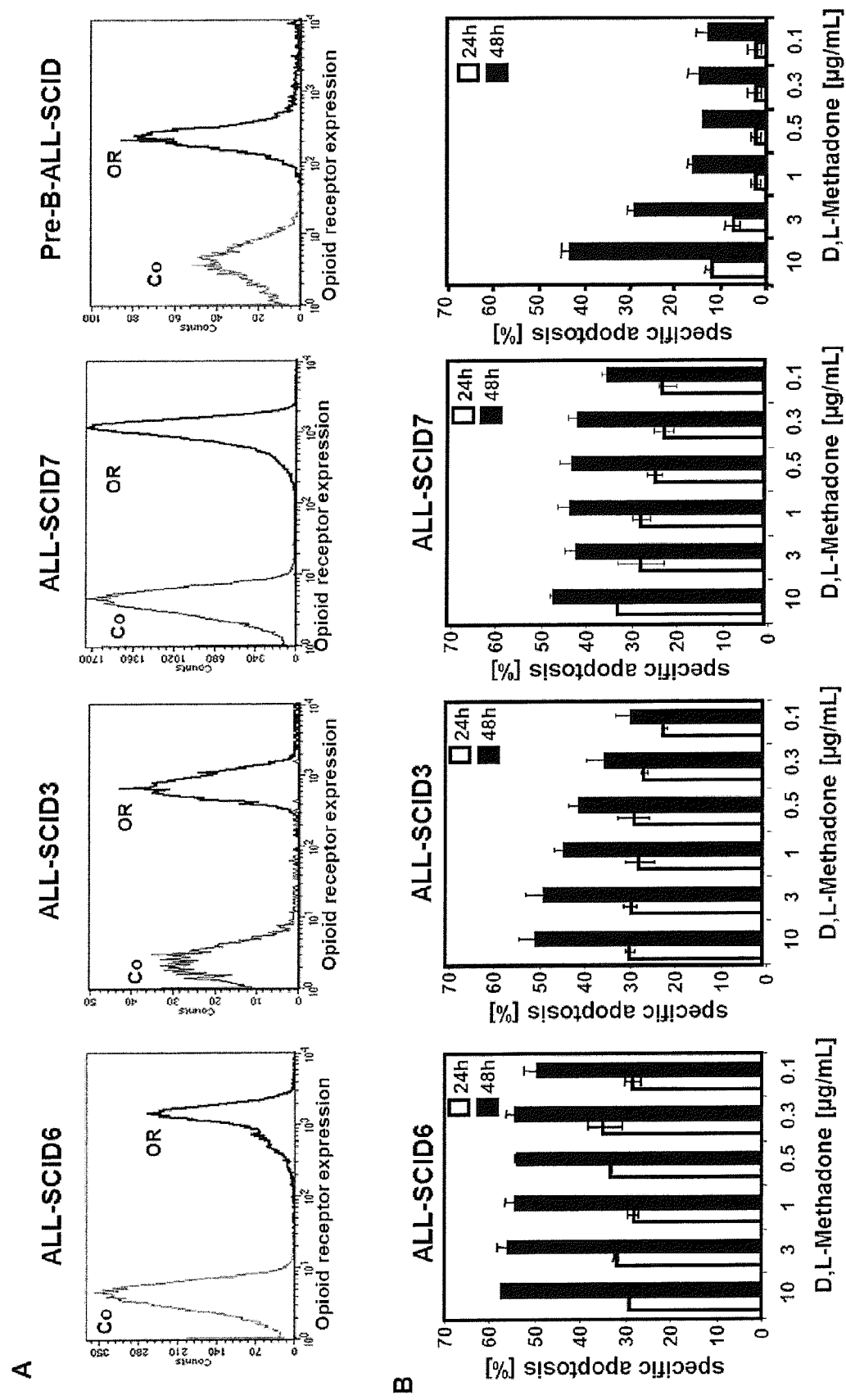
FIG. 1: D,L-methadone kills ALL cells ex vivo depending on critical levels of opioid receptor expression (A) Human ALL-SCID6 and ALL-SCID3, ALL-SCID7 and pre-B-ALL-SCID derived from xenografted mice display different levels of opioid-receptors on their cell surface. ALL-SCID6, ALL-SCID3 and ALL-SCID7 were stained with naloxone-fluoresceine measuring opioid-receptor expression (OR, thick black curve) and analyzed by flow-cytometry. Controls (Co) are exhibited as thin black curves.

(C) D,L-methadone strongly enhances doxorubicin sensitivity of xenograft-derived-BCP-ALL-patient-cells ex vivo. Xenograft-derived-BCP-ALL-cells (pre-B-ALL-SCID) were treated with different concentrations of D,L-methadone (as indicated) alone (–Doxo, white columns) with 0.01 µg/mL doxorubicin alone or with D,L-methadone in addition to doxorubicin (+Doxo, black columns). 48 h after stimulation, the percentages of apoptotic cells were measured by FSC/SSC-analysis. The percentage of specific apoptosis was calculated as described in FIG. 1B. Columns, mean of triplicates; bars, SD<10%.

Figure 3:
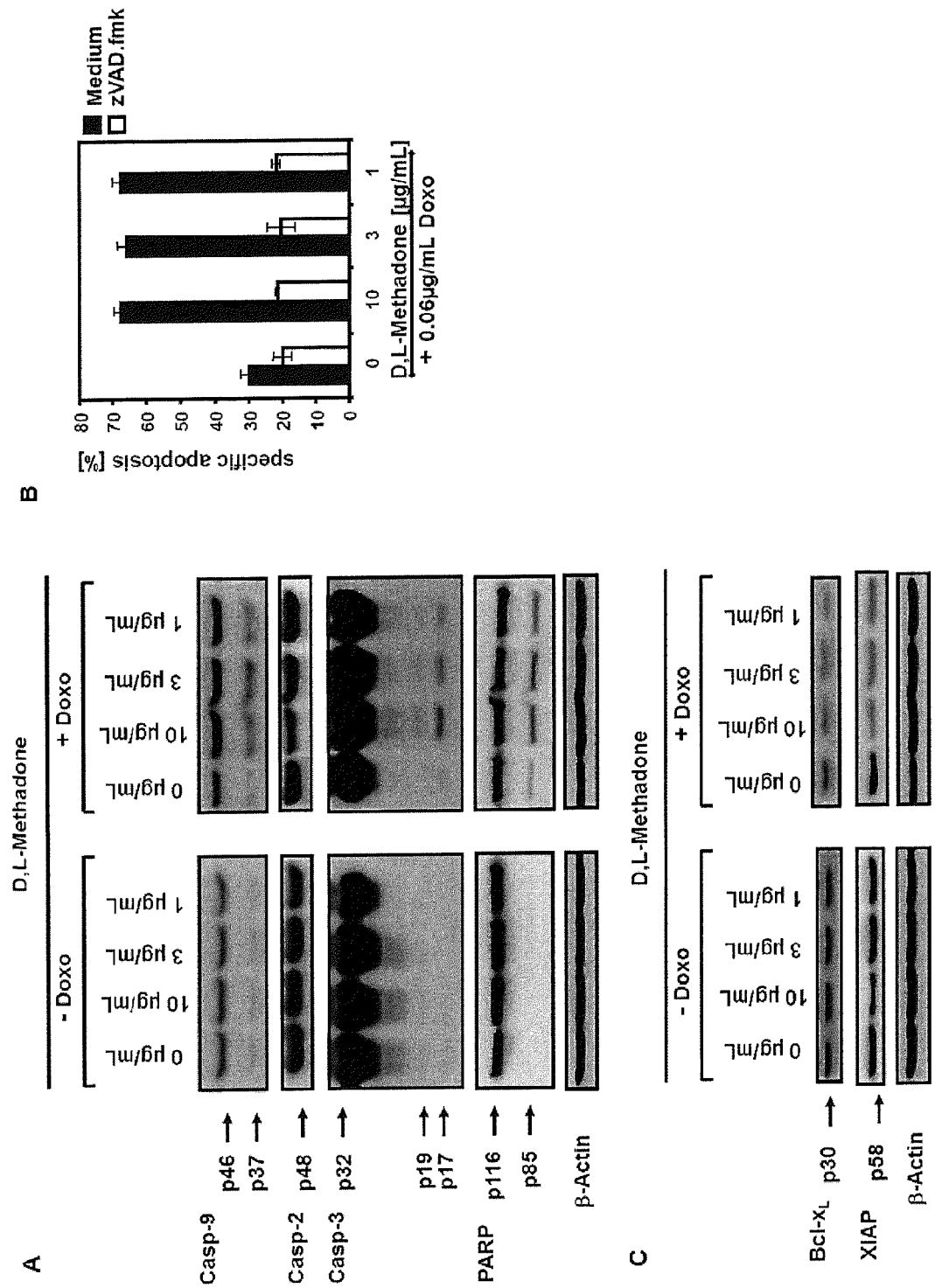

FIG. 3: D,L-methadone in combination with doxorubicin restores deficient activation of apoptotic pathways in BCP-ALL-cells expressing moderate amounts of opioid receptors in vitro (A) D,L-methadone and doxorubicin co-treatment provokes caspases activation. The BCP-ALL-cell line Tanoue was treated with D,L-methadone (as indicated) alone (–Doxo), with 0.06 µg/mL doxorubicin (+Doxo) alone or with D,L-methadone (as indicated) in addition to doxorubicin (+Doxo). After 120 h Western blot analyses for caspase-2, caspase-9, caspase-3 and PARP were performed. Downregulation of procaspase-2 was detected at ~48 kDa. The active fragment of caspase-9 was detected at ~37 kDa, the active fragment of caspase-3 at ~19 kDa and ~17 kDa and PARP cleavage at ~85 kDa. Equal protein loading was controlled by anti-β-actin antibody.

(B) D,L-methadone and doxorubicin-induced apoptosis depends on caspase activation. Pre-incubation of the cell line Tanoue with 50 µM of the caspase inhibitor zVAD.fmk for 1 h (white columns) or without pre-treatment (black columns) was followed by addition of D,L-methadone (as indicated) in combination with 0.06 µg/mL doxorubicin. Apoptosis induction was detected 120 h after stimulation by FSC/SSC-analysis. The percentage of specific apoptosis was calculated as described in FIG. 1B. Columns, mean of triplicates; bars, SD<10%.

(C) Downregulation of XIAP and Bcl-$x_L$ by D,L-methadone and doxorubicin co-treatment. The cell line Tanoue was treated with D,L-methadone (as indicated) alone (–Doxo), with 0.06 µg/mL doxorubicin (+Doxo) alone or with D,L-methadone (as indicated) in addition to doxorubicin (+Doxo). After 120 h Western blot analyses for XIAP and Bcl-$x_L$ were performed. XIAP was detected at 58 kDa and Bcl-$x_L$ at ~30 kDa. Equal protein loading was controlled by anti-β-actin antibody.

FIG. 4: Doxorubicin enhances opioid receptor expression whereas D,L-methadone enhances doxorubicin uptake and inhibits its efflux (A) Doxorubicin enhances opioid receptor expression on the cells' surface. The BCP-ALL-cell line Tanoue was treated for 96 h with 0.06 µg/mL doxorubicin. After staining of doxorubicin-treated (+Doxo) and untreated cells (–Doxo) with naloxone-fluoresceine relative fluorescence intensities were determined flowcytometrically. X-fold increase in opioid receptor expression is shown after subtracting the cells' autofluorescence (–Doxo) and doxorubicin fluorescence (+Doxo).

(B) D,L-methadone enhances doxorubicin uptake and inhibits its efflux. The BCP-ALL-cell line Tanoue was either pre-treated with 0.3 µg/mL doxorubicin (Doxo) alone or with a combination of doxorubicin and 10 µg/mL D,L-methadone (Doxo+methadone) for 24 h. Maximal doxorubicin cell uptake was analyzed via doxorubicin fluorescence in cells using flowcytometry after 24 h (0 h, max. uptake). After washing doxorubicin-treated cells, cells were either left untreated (Doxo) or treated with 10 µg/mL D,L-methadone (Doxo+Methadone) and incubated for different points in time (8 h, 24 h). Doxorubicin efflux was analyzed via doxorubicin fluorescence in cells using flowcytometry after 8 h and 24 h. Values are mean fluorescence intensities+/–SE.

Figure 5:
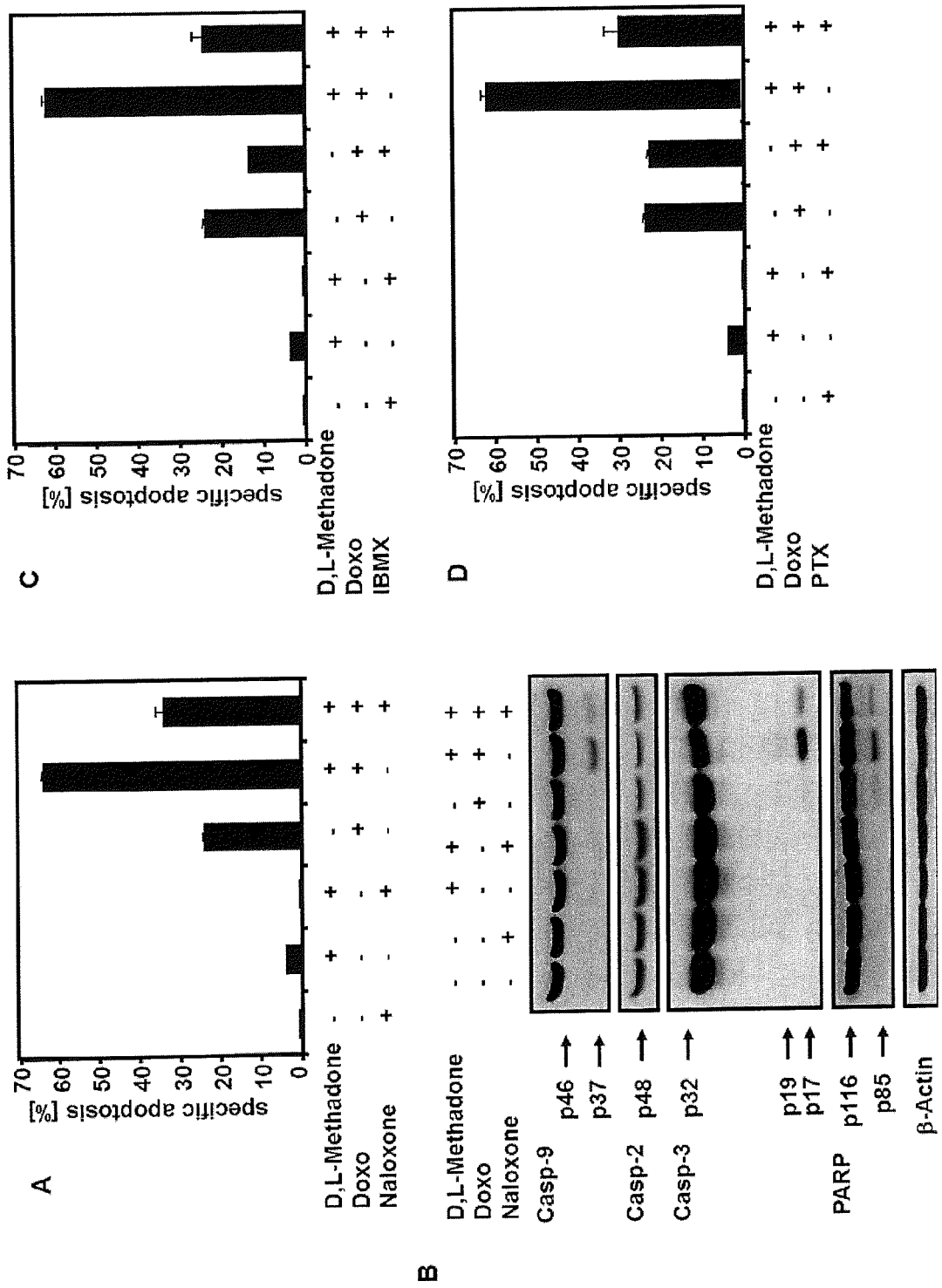

FIG. 5: Combination treatment with D,L-methadone and doxorubicin induced apoptosis depends on opioid-receptor triggering via downregulation of cAMP (A) Inhibition of opioid-receptor triggering inhibits apoptosis induction mediated by combination treatment with D,L-methadone and doxorubicin. The BCP-ALL-cell line Tanoue was incubated with 60 µg/mL naloxone (Naloxone), 3 µg/mL D,L-methadone (D,L-Methadone) and 0.06 µg/mL doxorubicin (Doxo) alone or in different combinations as indicated. After 96 h, the percentages of apoptotic cells were measured by FSC/SSC-analysis.

(B) Inhibition of opioid-receptor triggering inhibits caspase activation mediated by combination treatment with D,L-methadone and doxorubicin. The BCP-ALL-cell line Tanoue was incubated with 60 µg/mL naloxone (Naloxone), 3 µg/mL D,L-methadone (D,L-Methadone) and 0.06 µg/mL doxorubicin (Doxo) alone or in different combinations as indicated. Western blot analyses for caspase-2, caspase-9, caspase-3 and PARP were performed after 96 h of incubation. Downregulation of procaspase-2 was detected at ~48 kDa. The active fragment of caspase-9 was detected at ~37 kDa, of caspase-3 at ~19 kDa and ~17 kDa and PARP cleavage at ~85 kDa. Equal protein loading was controlled by anti-β-actin antibody.

(C) Increasing cAMP levels via repression of phosphodiesterase activity inhibits apoptosis. The BCP-ALL-cell line Tanoue was incubated for 96 h with 200 µM 3-Isobutyl-1-methylxanthine (IBMX), 3 µg/mL D,L-methadone (D,L-Methadone) and 0.06 µg/mL doxorubicin (Doxo) alone or in different combinations as indicated.

(D) Uncoupling inhibitory G-proteins from opioid receptors inhibits apoptosis by preventing inhibition of adenylyl cyclase. The BCP-ALL-cell line Tanoue was incubated with 20 ng/mL pertussis toxin (PTX), 3 µg/mL D,L-methadone (D,L-Methadone) and 0.06 µg/mL doxorubicin (Doxo) alone or in different combinations as indicated. After 96 h, the percentages of apoptotic cells were measured by FSC/SSC-analysis. The fraction of apoptotic cells were determined by FSC/SSC-analysis. The percentage of specific apoptosis was calculated as described in FIG. 1B. Columns, mean of triplicates; bars, SD<10%.

Figure 6:
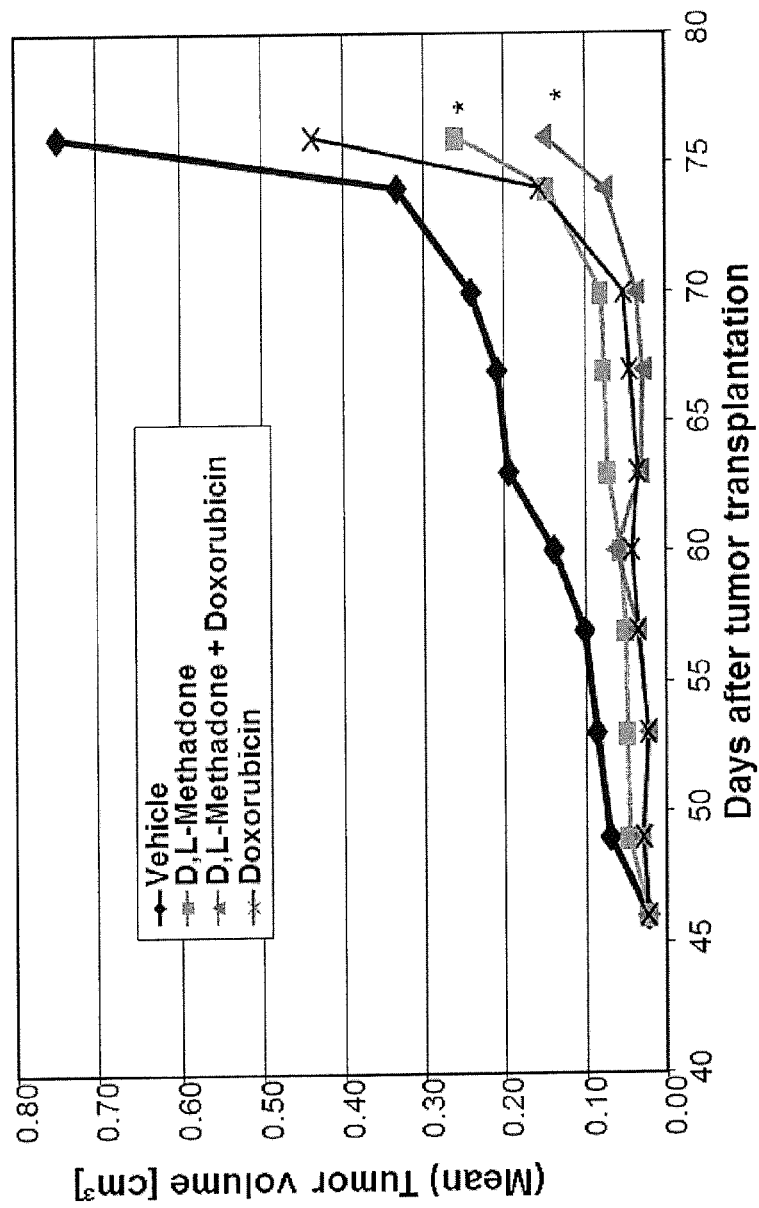

FIG. 6: D,L-methadone inhibits growth of leukemia xenografts and increases doxorubicin sensitivity Fragments of an in vivo passage of a patient-derived T-ALL (ALL-SCID6, see also FIG. 1) were transplanted into male NSG mice. Mice were treated with D,L-methadone alone (n=8, orally day 1-76, D,L-Methadone), with doxorubicin alone (n=8, i.v. day 46, 53, 60, 76, Doxorubicin) or with a combination treatment with D,L-methadone and doxorubicin (n=8, D,L-Methadone+Doxo). D,L-methadone was used in weekly increasing doses from 20 up to 120 mg/kg/day and doxorubicin in a dose of 3 mg/kg. As control group xenografted mice were treated i.v. with 10% Tween 80 in saline (n=8, Vehicle). For 76 days after transplantation all mice were monitored for tumour growth, body weight and health condition. *significant to vehicle (p<0.05, Mann-Whitney U test).

Figure 7:
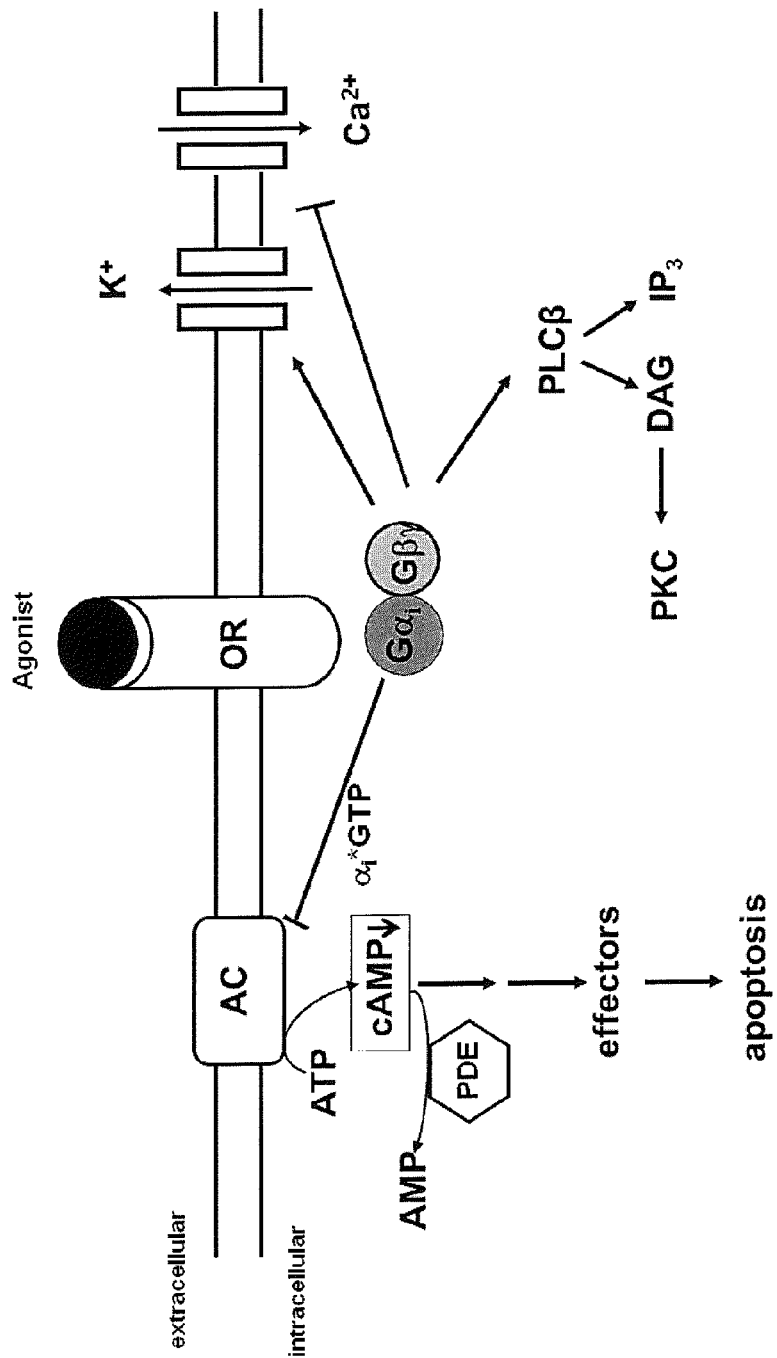

FIG. 7: Opioid receptor signaling. Stimulation of opioid receptors (OR) by agonists like D,L-methadone leads to an activation of the inhibitory $G_i$-protein. The $\alpha_i$-subunit inactivates adenylyl cyclase (AC) resulting in a reduction of cAMP levels within the cell which in turn leads to apoptosis which might be mediated by several different modulators. Also the $\beta_\gamma$-subunits of the $G_i$-protein modulate the activity of different effectors like the inhibition of $Ca^{2+}$- and the activation of $K^+$-channels.

Figure 8:
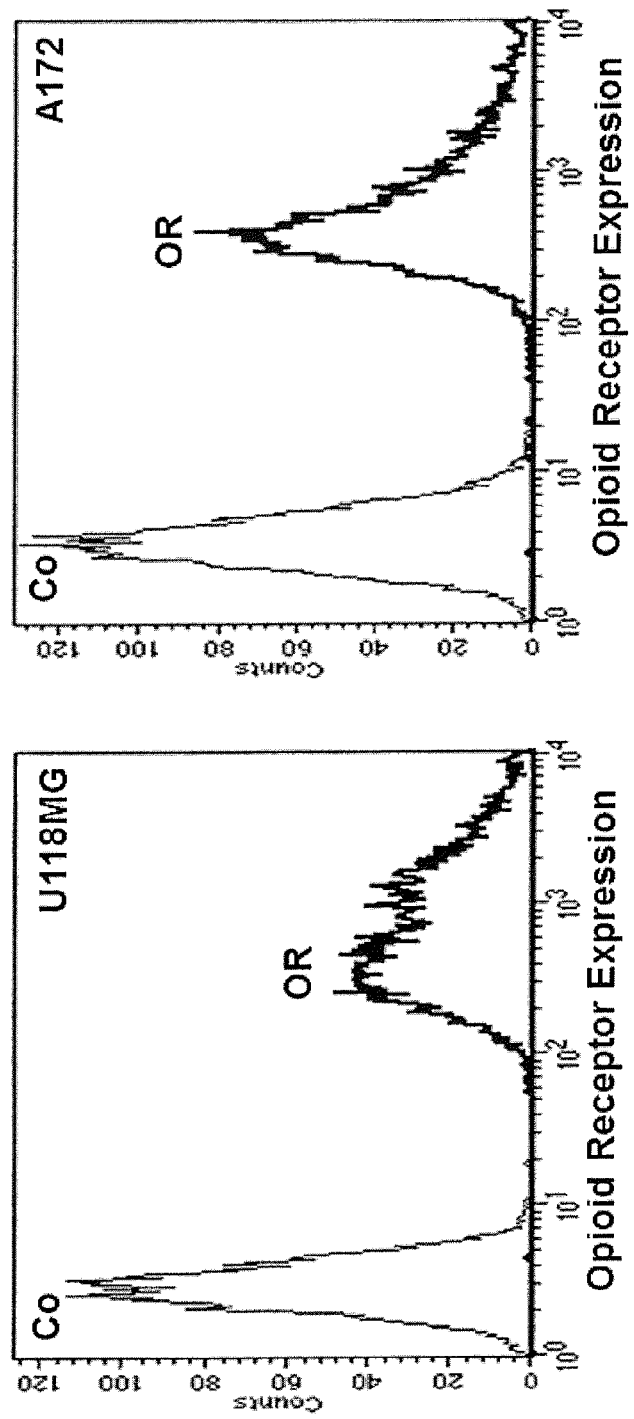

FIG. 8: Opioid receptor expression on glioblastoma cells. The glioblastoma cell lines U118MG and A172 were stained with naloxone fluorescein measuring opioid receptor expression (OR, thick black curve) and analysed by flow cytometry. Controls (Co) are exhibited as thin black curves.

Figure 9:
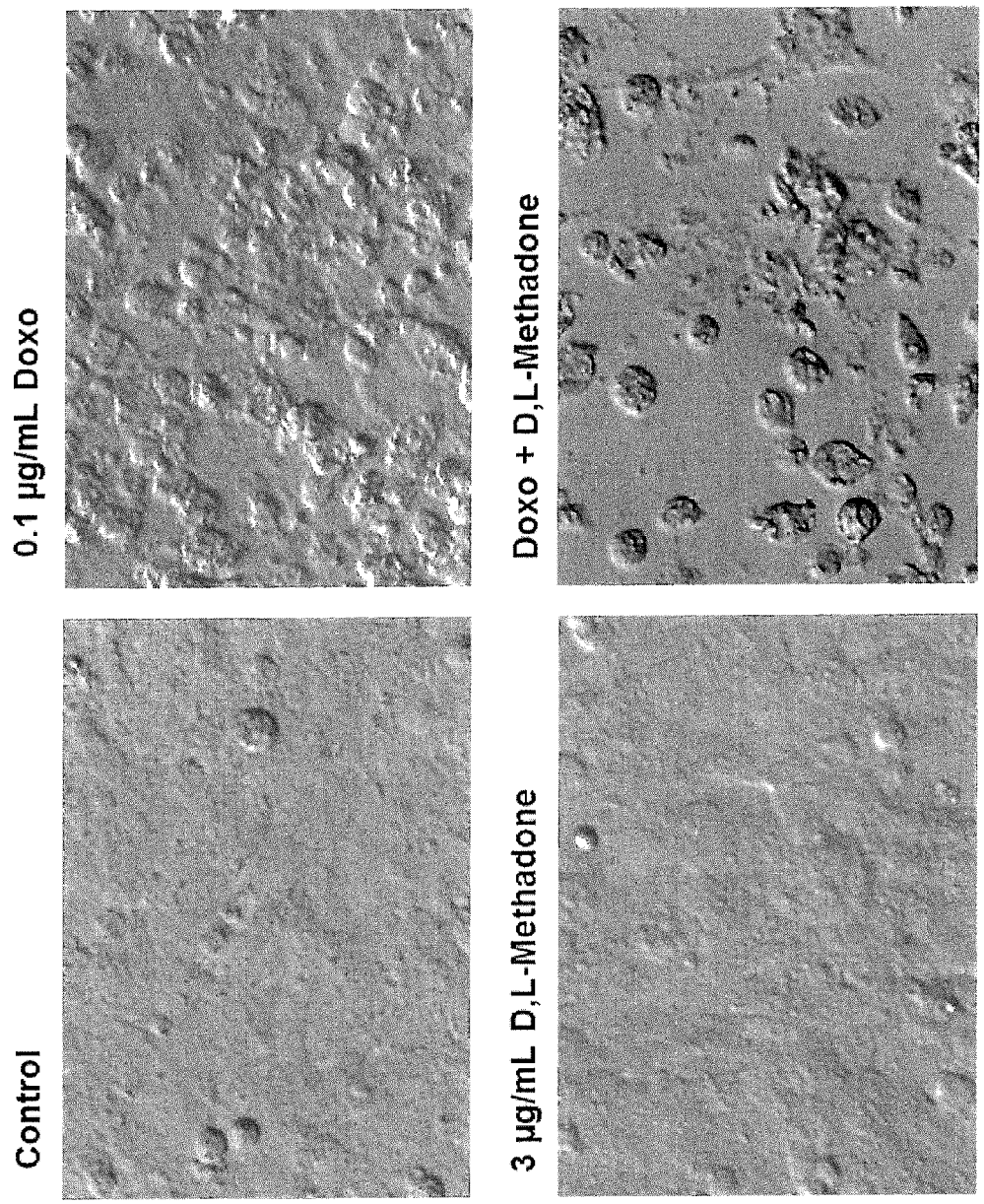

FIG. 9: D,L-methadone sensitizes glioblastoma cells for doxorubicin treatment. Glioblastoma cells A172 were incubated with 3 µg/mL D,L-methadone alone, with 0.1 µg/mL doxorubicin (0.1 µg/mL Doxo) alone or with 3 µg/mL D,L-methadone in combination with 0.1 µg/mL doxorubicin (Doxo+D,L-Methadone). Control represents untreated glioblastoma cells. After 144 h light microscopy pictures were taken. Cotreatment of A172 with 3 µg/mL D,L-methadone and 0.1 µg/mL doxorubicin led to detachment of the cells from the ground, membrane-blebbing and cell-shrinkage.

Figure 10:
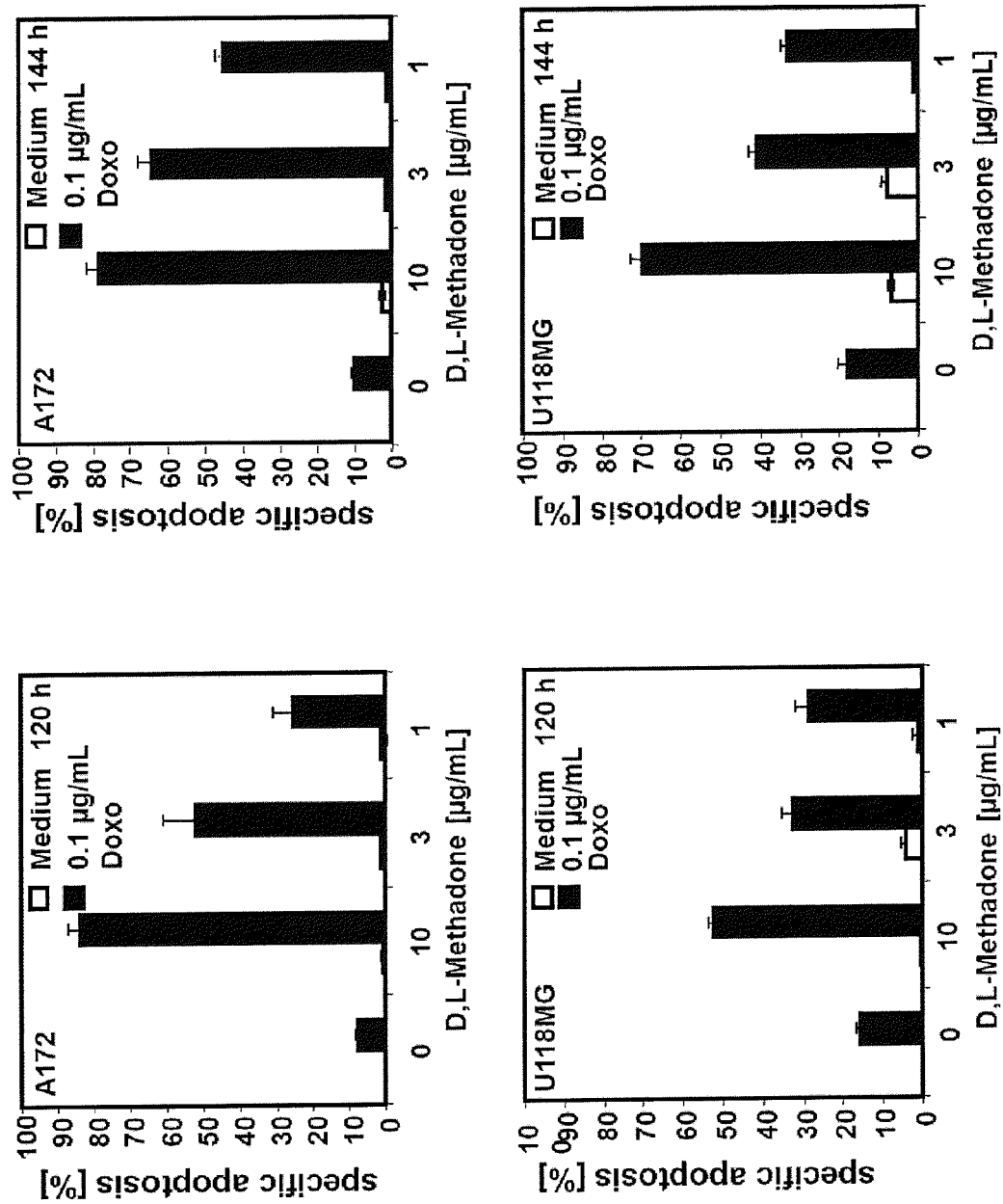

FIG. 10: Combination treatment with D,L-methadone and doxorubicin induces apoptosis in glioblastoma cells. A172 and U118MG glioblastoma cells were treated with different concentrations of D,L-methadone (10, 3, 1 µg/mL) alone (Medium, white columns), with doxorubicin (0.1 µg/mL Doxo, black columns) alone or with different concentrations of D,L-methadone (10, 3, 1 µg/mL) in addition to doxorubicin (0.1 µg/mL Doxo, black columns). After 120 h and 144 h the percentages of apoptotic cells were measured by hypodiploid DNA analysis. The percentage of specific apoptosis was calculated as follows: 100×[experimental dead cells (%)−spontaneous dead cells in medium (%)]/[100%−spontaneous dead cells in medium (%)]. Columns, mean of triplicates; bars, SD<10%. Similar results were obtained in three independent experiments.

Figure 11:
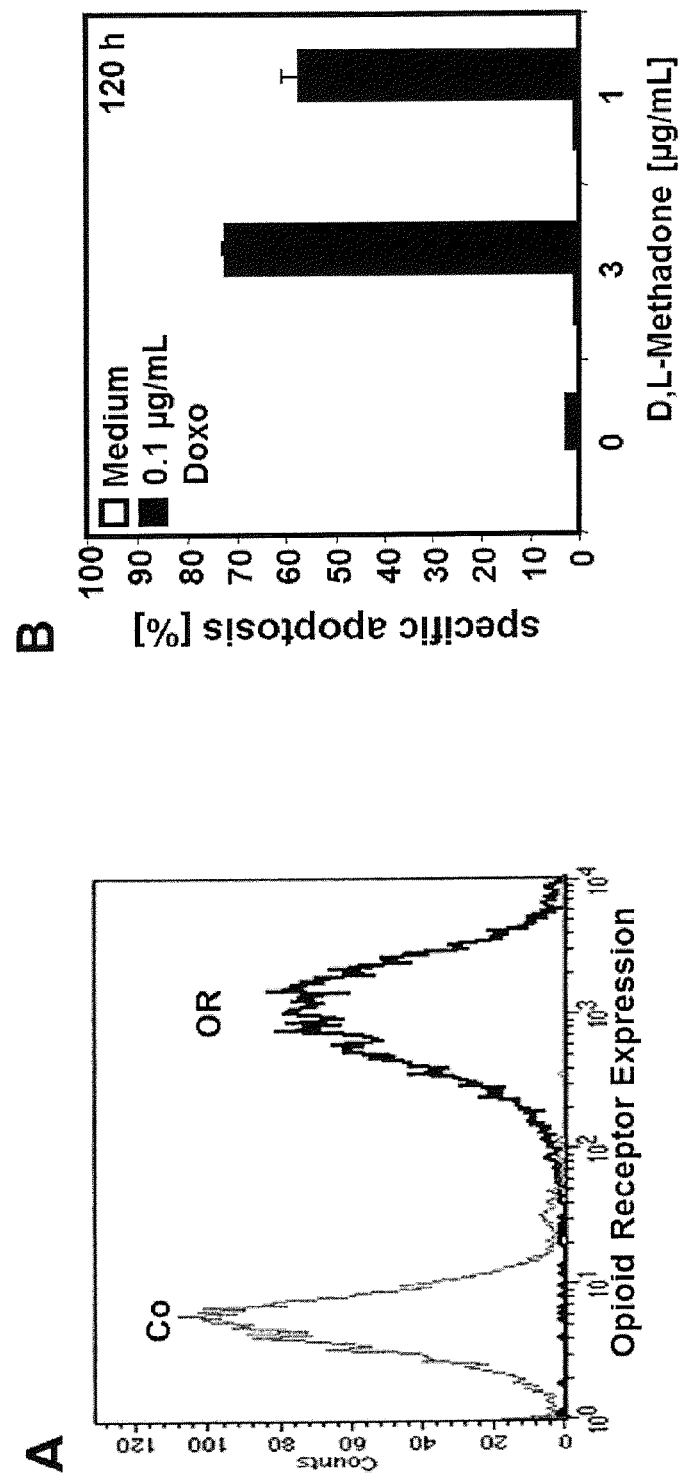
Figure 12:
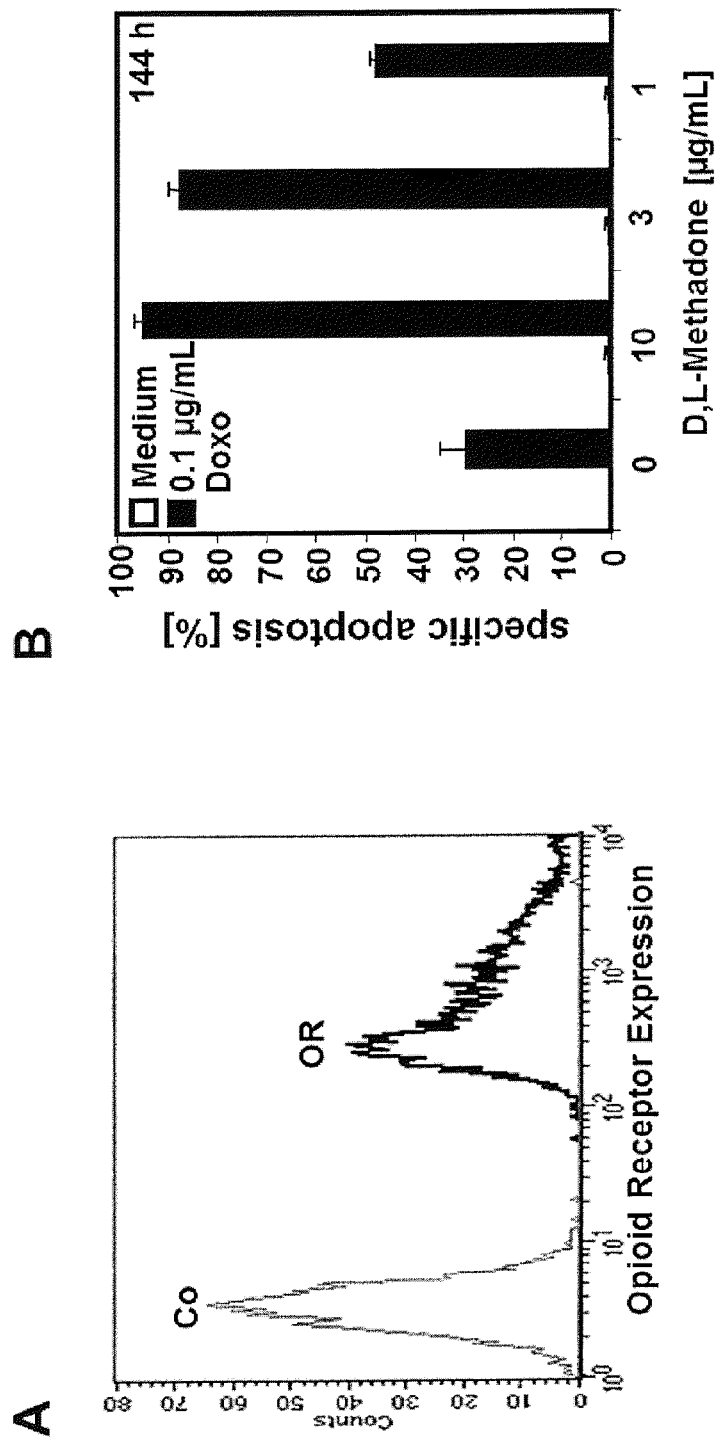

FIG. 11: D,L-methadone sensitizes primary human glioblastoma cells for doxorubicin treatment. (A) Primary human glioblastoma cells were stained with naloxone fluorescein measuring opioid receptor expression (OR, thick black curve) and analyzed by flow cytometry. Control (Co) is exhibited as thin black curve. (B) Primary human glioblastoma cells were treated with different concentrations of D,L-methadone (3, 1 µg/mL) alone (Medium, white columns) with 0.1 µg/mL doxorubicin (0.1 µg/mL Doxo, black columns) alone or with D,L-methadone (3, 1 µg/mL) in addition to 0.1 µg/mL doxorubicin (0.1 µg/mL Doxo, black columns). After 120 h the percentages of apoptotic cells were measured by hypodiploid DNA analysis. The percentage of specific apoptosis was calculated as described in FIG. 1c. Columns, mean of triplicates, bars, SD <10%. Similar results were obtained in three independent experiments FIG. 12: D,L-methadone sensitizes glioblastoma-initiating stem cells for doxorubicin treatment. (A) Glioblastoma-initiating stem cells were stained with naloxone fluorescein measuring opioid receptor expression (OR, thick black curve) and analyzed by flow cytometry. Control (Co) is exhibited as thin black curve. (B) Glioblastoma-initiating-stem cells were treated with different concentrations of D,L-methadone (10, 3, 1 µg/mL) alone (Medium, white columns), with 0.1 µg/mL doxorubicin (0.1 µg/mL Doxo, black columns) alone or with D,L-methadone (3, 1 µg/mL) in addition to 0.1 µg/mL doxorubicin (0.1 µg/mL Doxo, black columns). After 144 h the percentages of apoptotic cells were measured by hypodiploid DNA analysis. The percentage of specific apoptosis was calculated as described in FIG. 1c. Columns, mean of triplicates; bars, SD <10%. Similar results were obtained in three independent experiments.

FIG. 13: Cell death induction of glioblastoma cells using D,L-methadone and doxorubicin cotreatment depends on caspases activation. (A) D,L-methadone restored deficient caspases activation by doxorubicin in glioblastoma cells. A172 were treated with different concentrations of D,L-methadone (3, 1 µg/mL) alone, with 0.1 µg/mL doxorubicin (0.1 µg/mL Doxo) alone or with different concentrations of D,L-methadone (3, 1 µg/mL) in addition to doxorubicin (0.1 µg/mL Doxo). After 144 h Western blot analyses for caspase-10, -2, -9, -3 and PARP were performed. Downregulation of procaspase-10 was detected at ~58 kDa and of procaspase-2 at ~48 kDa. The active fragment of caspase-9 was detected at ~37 kDa, the active fragment of caspase-3 at ~17 kDa and PARP cleavage at ~85 kDa. Equal protein loading was controlled by anti-β-actin antibody. (B) Inhibition of caspases activation with the broad spectrum inhibitor of caspases zVAD.fmk blocks apoptosis induced by cotreatment of D,L-methadone and doxorubicin in A172 cells. Glioblastoma cells A172 were treated with different concentrations of D,L-methadone (10, 3, 1 µg/mL) in combination with 0.1 µg/mL doxorubicin (+0.1 µg/mL Doxo) in the absence (Medium, black columns) or presence of 50 µmol/L of zVAD.fmk (white columns, 50 µmol/L zVAD.fmk). After 120 h and 144 h, the percentages of apoptotic cells were measured by hypodiploid DNA analysis. The percentage of specific apoptosis was calculated as described in FIG. 1c. Columns, mean of triplicates; bars, SD<10%. Similar results were obtained in three independent experiments. (C) Downregulation of XIAP and Bcl-$x_L$ in glioblastoma cells by using D,L-methadone in combination with doxorubicin. Glioblastoma cells A172 were treated with different concentrations of D,L-methadone (3, 1 µg/mL) alone, with 0.1 µg/mL doxorubicin (0.1 µg/mL Doxo) alone or with D,L-methadone (3, 1 µg/mL) in addition to doxorubicin (0.1 µg/mL Doxo) for 144 h. Western blot analyses for XIAP and Bcl-$x_L$ were performed. XIAP was detected at 58 kDa and Bcl-$x_L$ was detected at 30 kDa. Equal protein loading was controlled by anti-β-actin antibody.

Figure 14:
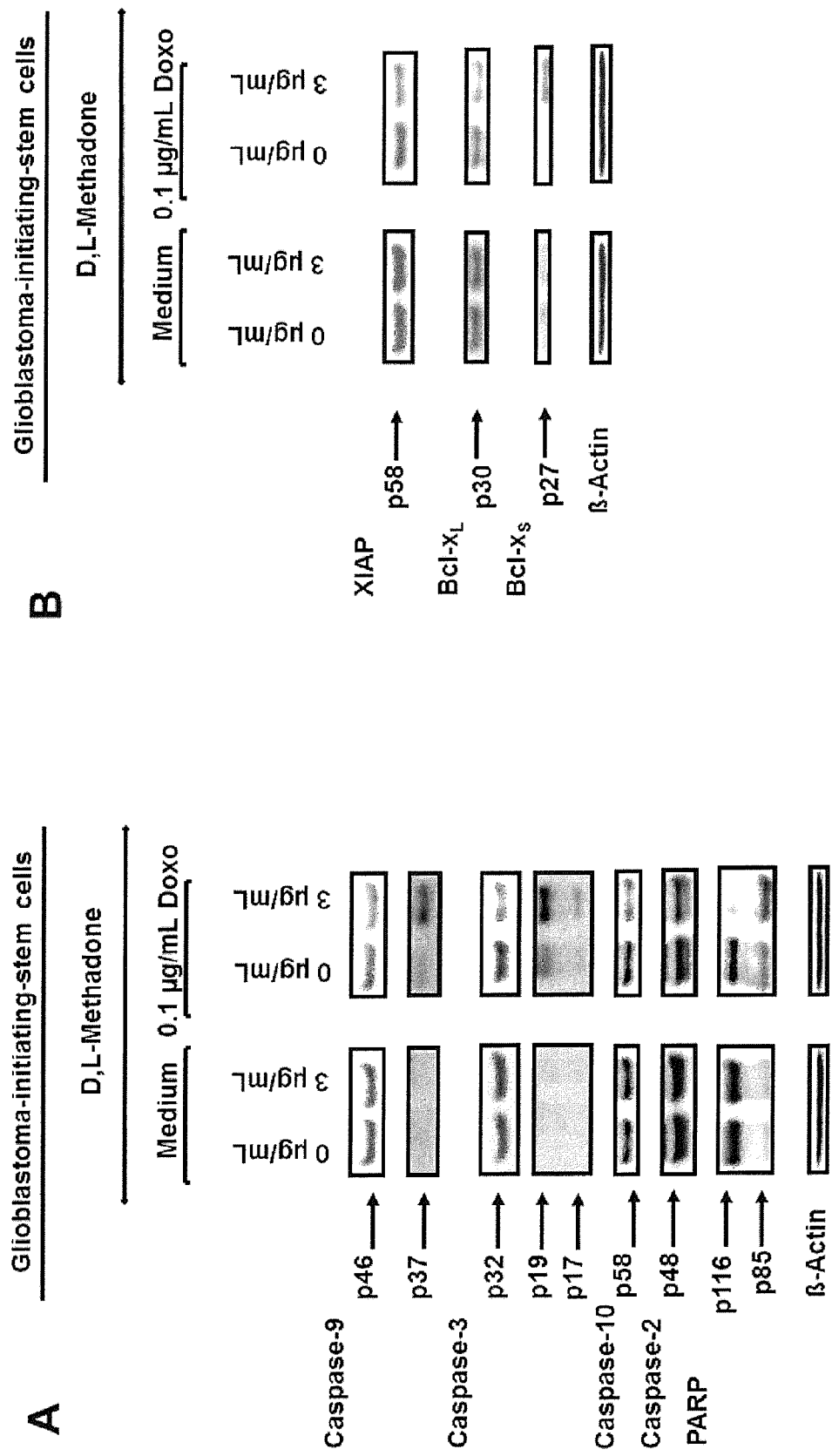

FIG. 14: D,L-methadone reversed deficient activation of apoptosis pathways by doxorubicin in glioblastoma-initiating-stem cells. (A) Glioblastoma-initiating-stem cells were treated with D,L-methadone (3 µg/mL) alone, with 0.1 µg/mL doxorubicin (0.1 µg/mL Doxo) alone or with D,L-methadone (3 µg/mL) in addition to doxorubicin (0.1 µg/mL Doxo). After 144 h Western blot analyses for caspase-10, -2, −9, −3 and PARP were performed. Downregulation of procaspase-10 was detected at ~58 kDa and of procaspase-2 at ~48 kDa. The active fragment of caspase-9 at ~37 kDa, the active fragment of caspase-3 at ~19 kDa and ~17 kDa and PARP cleavage at ~85 kDa. Equal protein loading was controlled by anti-β-actin antibody. (B) Glioblastoma-initiating-stem cells were treated with D,L-methadone (3 µg/mL) alone, with 0.1 µg/mL doxorubicin (0.1 µg/mL Doxo) alone or with D,L-methadone (3 µg/mL) in addition to doxorubicin (0.1 µg/mL Doxo) for 144 h. Western blot analyses for XIAP, Bcl-$x_L$ and Bcl-$x_S$ were performed. XIAP was detected at 58 kDa, Bcl-$x_L$ was detected at 30 kDa and Bcl-$x_S$ was detected at 27 kDa. Equal protein loading was controlled by anti-β-actin antibody.

Figure 15:
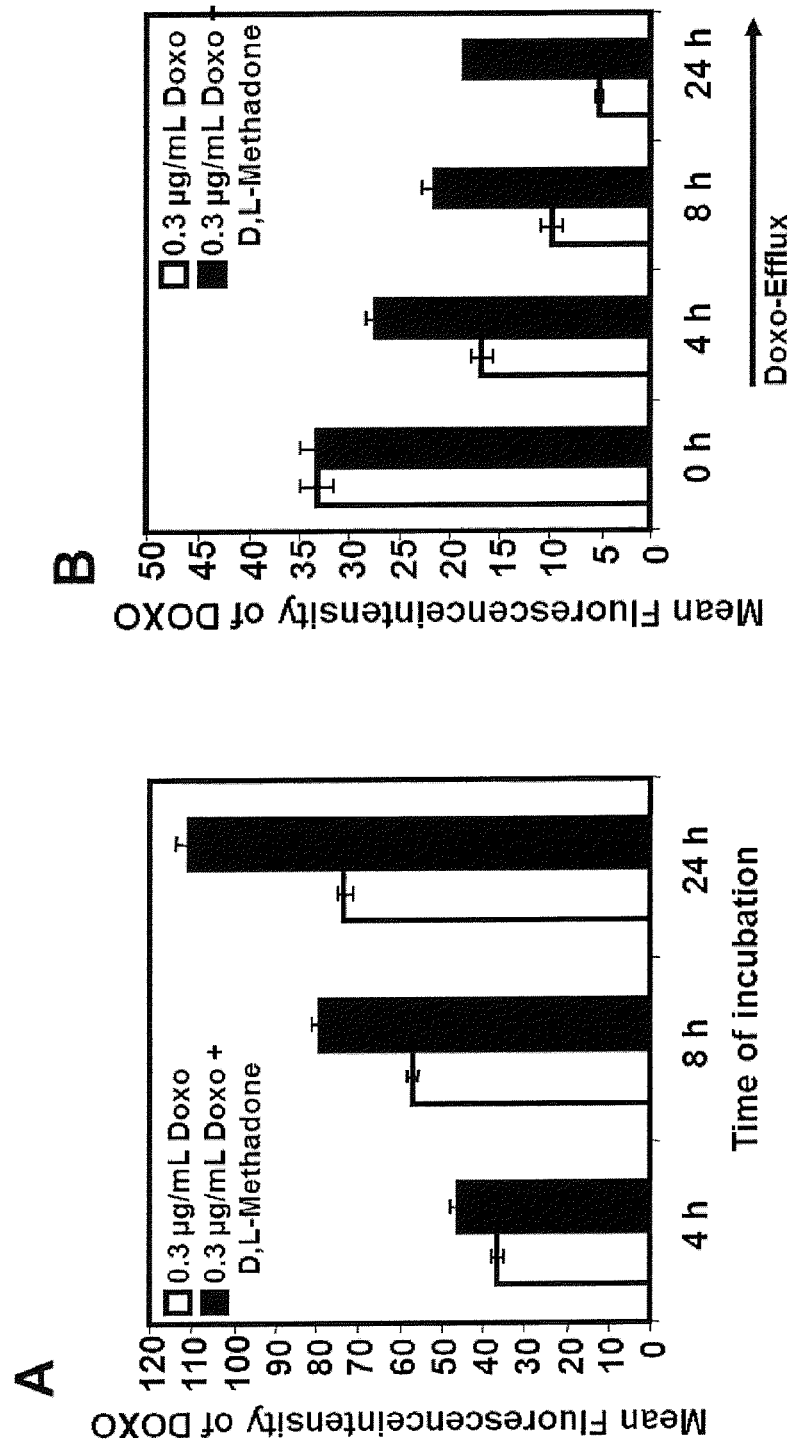

FIG. 15: D,L-methadone enhances doxorubicin uptake and inhibits its efflux. (A) D,L-methadone enhances doxorubicin-accumulation in the glioblastoma cell line A172. A172 were incubated with 0.3 µg/mL doxorubicin alone or in combination with 10 µg/mL D,L-methadone. After 4, 8 and 24 h incubation the fluorescence intensity of doxorubicin (Doxo) using flow cytometry analysis were determined. In the graphic the relative doxorubicin-uptake is shown. Columns, mean of triplicates; bars, SD<10%. Similar results were obtained in three independent experiments. (B) A172 were incubated with 0.3 µg/mL doxorubicin for 4 h. At distinct points in time (4, 8 and 24 h) after washing the doxorubicin-containing medium away (0 h) the fluorescence intensity of doxorubicin using flow cytometry analysis was determined. In the graphic the relative doxorubicin-content is shown. Columns, mean of triplicates; bars, SD<10%. Similar results were obtained in three independent experiments.

Figure 16:
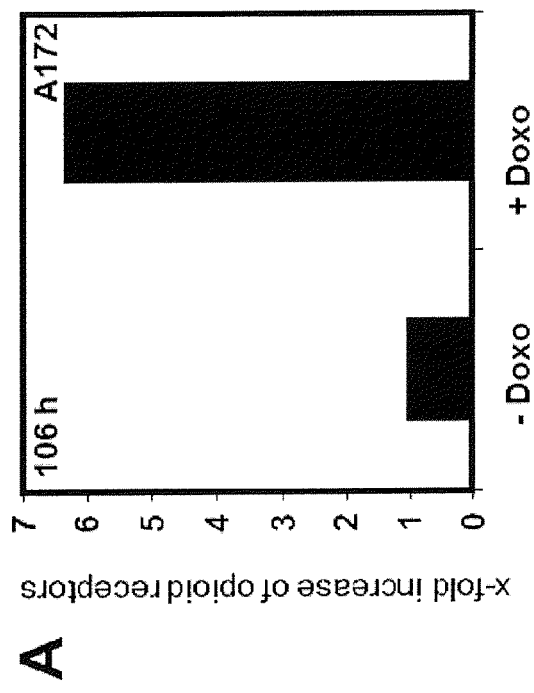

FIG. 16: 1 Doxorubicin enhances opioid receptor expression on the cell surface.

(A) The glioblastoma cell line A172 was treated for 106 h with 0.1 µg/mL doxorubicin. After staining of doxorubicin-treated (doxorubicin) and untreated cells with naloxone-fluorescein (naloxone) relative fluorescence intensities were determined flowcytometrically. (B) Tabular summary of untreated and doxorubicin control cells, naloxone treated cells, whereas $D_{(naloxone-control)}$ represents the median fluorescence intensities after subtracting the cells' autofluorescence (control).

Figure 17:
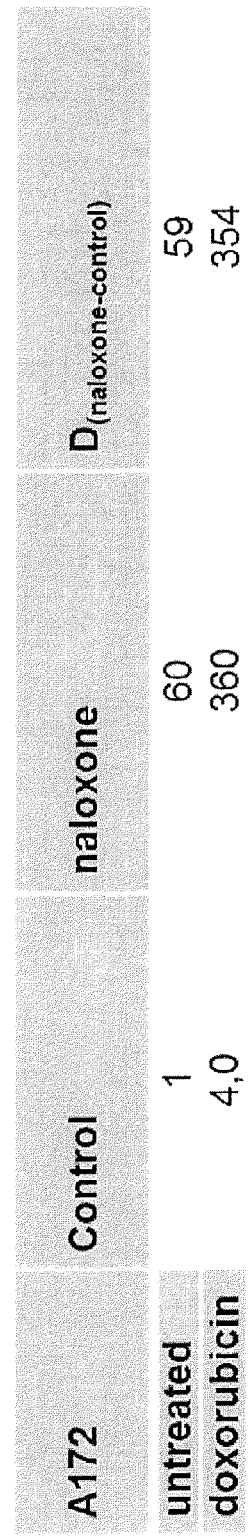
Figure 17:
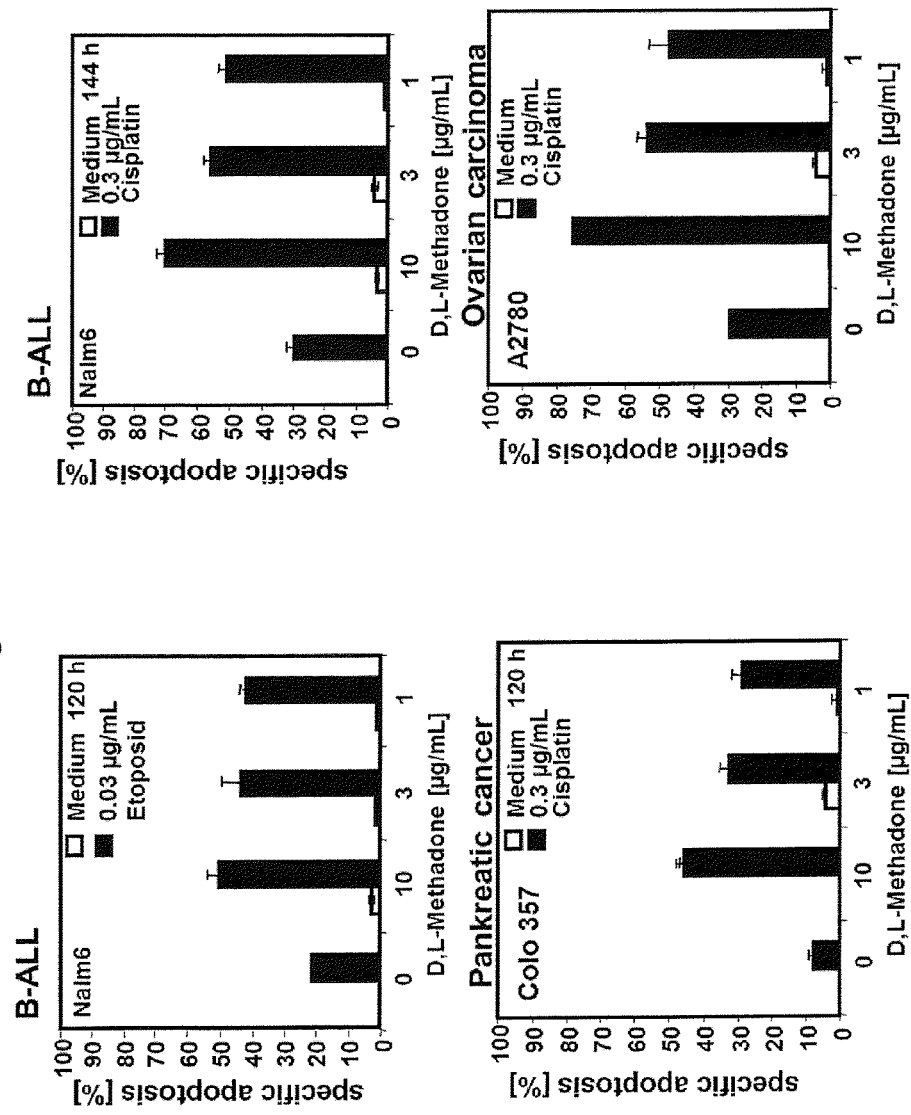

FIG. 17: D,L-methadone sensitizes leukemia cancer cells (Nalm-6), pancreatic cancer cells (Colo357) and ovarian cancer cells (A2780) for etoposide or cisplatin treatment. The Nalm6, Colo357 and A2780 cells were treated with different concentrations of D,L-methadone (10, 3, 1 µg/mL) alone (Medium, white columns), with 0.03 µg/mL Etoposide or 0.3 µg/mL cisplatin alone or with D,L-methadone (10, 3, 1 µg/mL) in addition to 0.03 µg/mL Etoposide (0.03 µg/mL Etoposide, black columns) or 0.3 µg/mL cisplatin (0.3 µg/mL cisplatin, black columns). After 120 to 144 h the percentages of apoptotic cells were measured by hypodiploid DNA analysis. The percentage of specific apoptosis was calculated as described in FIG. 1c. Columns, mean of triplicates; bars, SD<10%. Similar results were obtained in three independent experiments.

Figure 18:
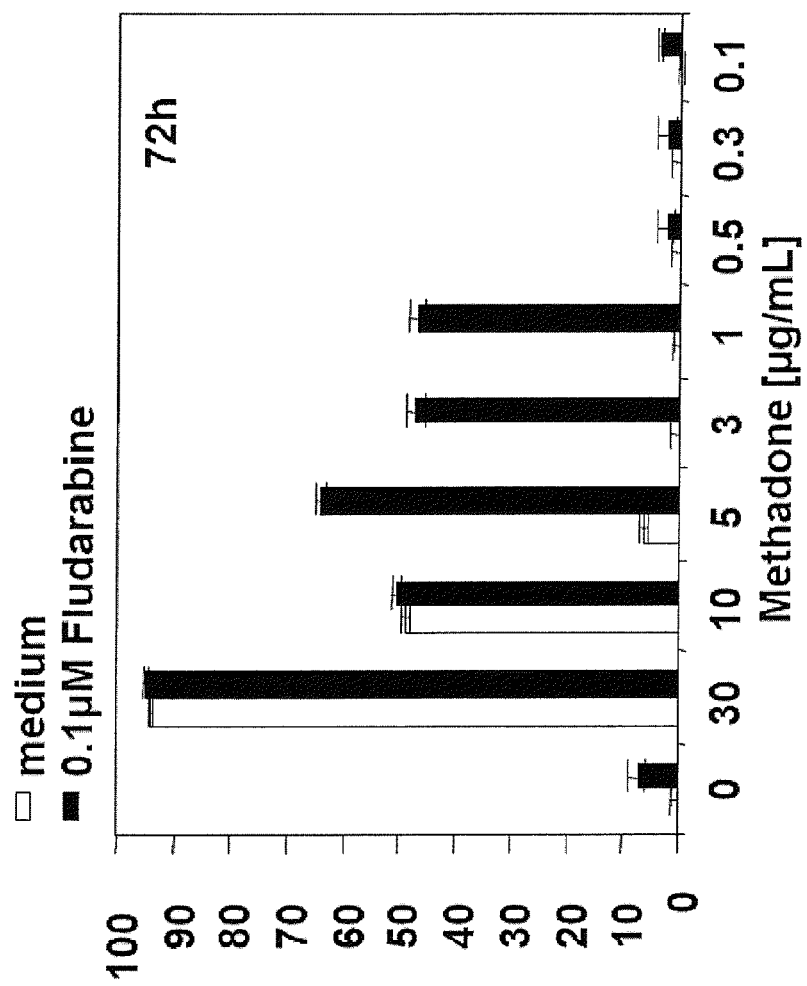

FIG. 18: D,L-methadone sensitizes chronic lymphocytic leukemia (CLL) cells for Fludarabine treatment. The CLL cells were treated with different concentrations of D,L-methadone (10, 3, 1 µg/mL) alone (Medium, white columns), with 0.1 µM Fludarabine (0.1 µM Fludarabine, black columns) alone or with D,L-methadone (30, 10, 5, 3, 1, 0.5, 0.3, 0.1 µg/mL) in addition to 0.1 µM Fludarabine (0.1 µM Fludarabine, black columns). After 72 h the percentages of apoptotic cells were measured by hypodiploid DNA analysis. The percentage of specific apoptosis was calculated as described in FIG. 1B. Columns, mean of triplicates; bars, SD<10%. Similar results were obtained in three independent experiments.

Figure 19:
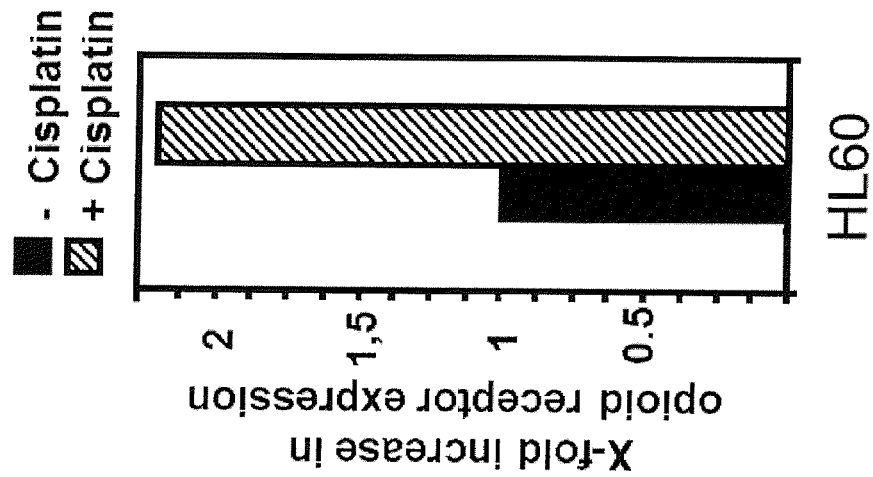

FIG. 19: Cisplatin enhances opioid receptor expression in HL60 cells

Cisplatin enhances opioid receptor expression on the surface of the promyelocytic leukemia cell line HL60. The HL60 cell line was treated for 24 h with 0.3 µg/mL cisplatin. After staining of cisplatin-treated (+Cisplatin) and untreated cells (−Cisplatin) with naloxone-fluoresceine relative fluorescence intensities were determined flowcytometrically. 2.1-fold increase in opioid receptor expression is shown after subtracting the cells autofluorescence.

Figure 20:
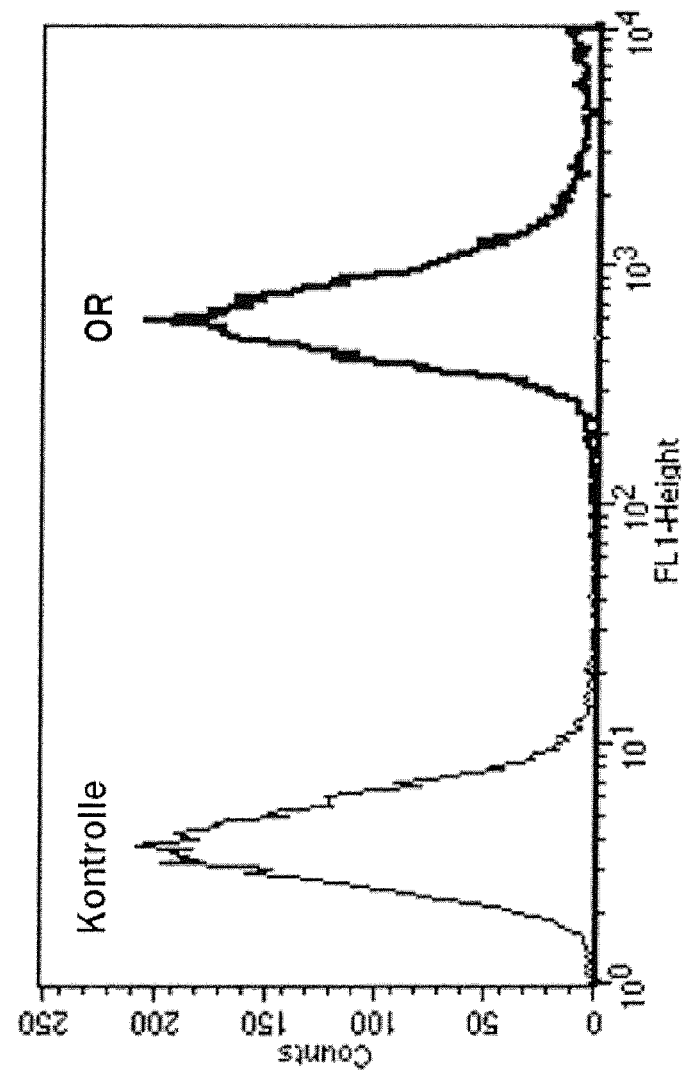

FIG. 20: The Her2/neu-resistant mamma carcinoma cell line JIMT-1 expresses high levels of the µ-opioid receptor The human JIMT-1 cell line, derived from a pleural metastasis of a 62-year old patient with breast cancer who was clinically resistant to Herceptin displays opioid-receptors on its cell surface. JIMT-1 cells were stained with naloxone-fluorescein measuring opioid-receptor expression (OR, thick black curve) and analyzed by flow cytometry. Controls (Co) are exhibited as thin black curves.

Figure 21:
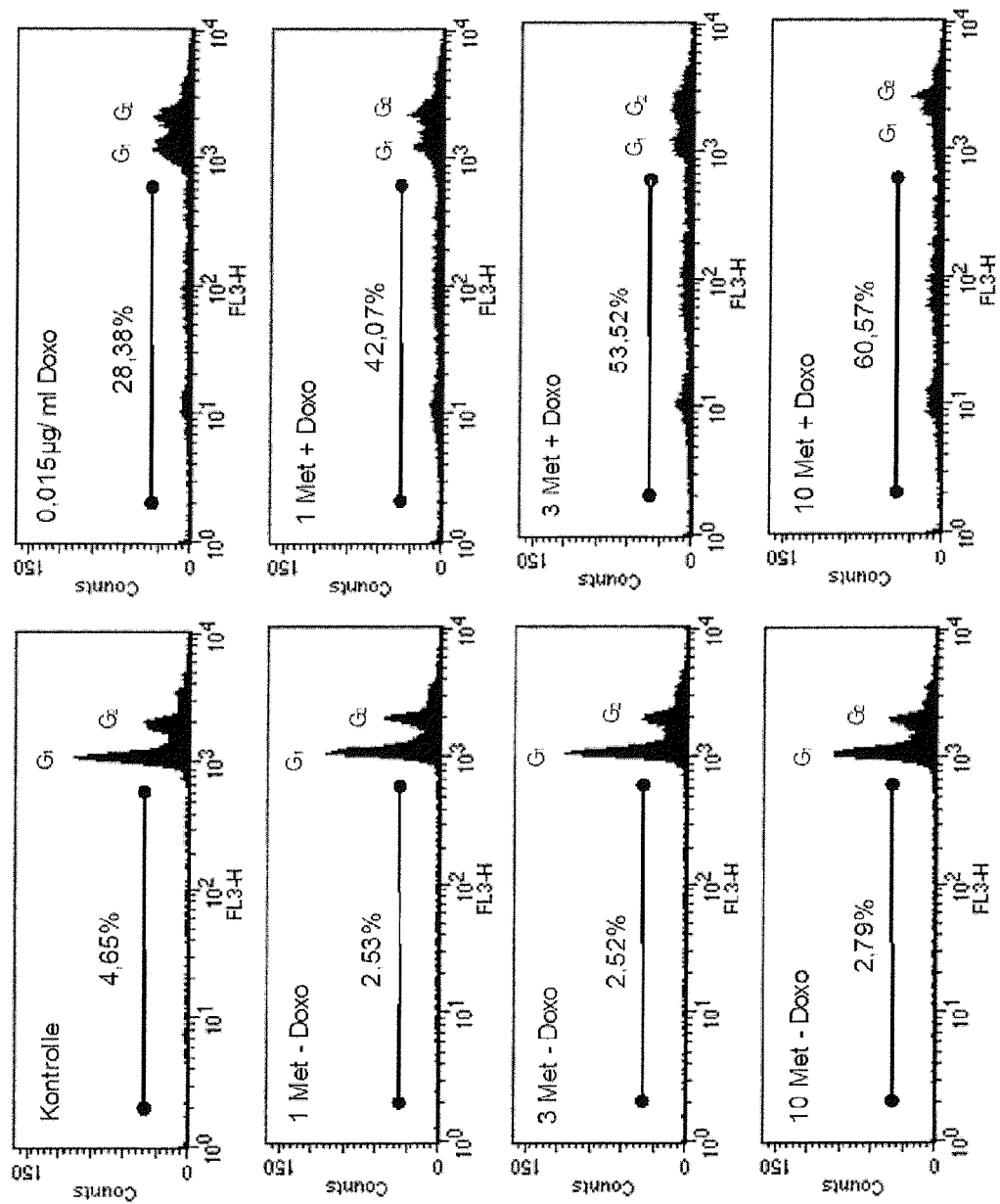
Figure 21:
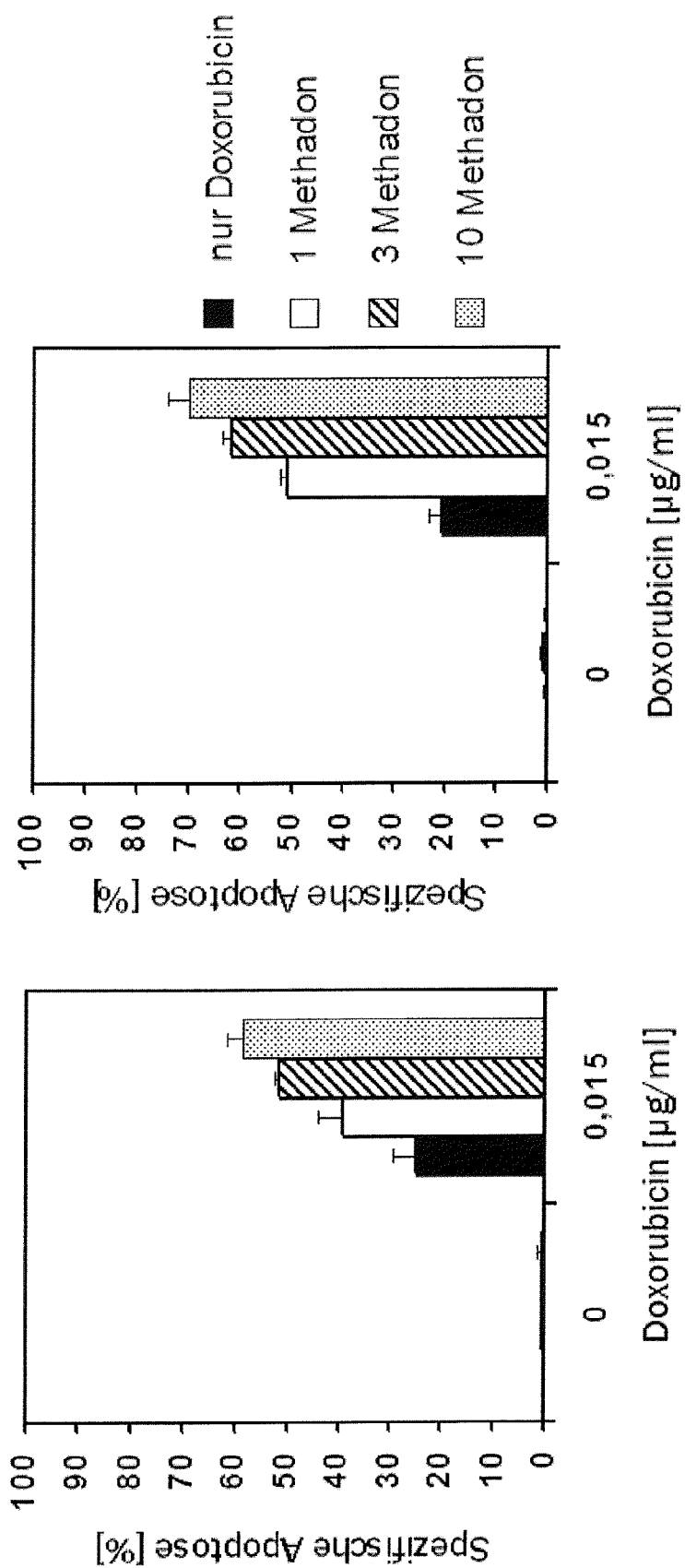

FIG. 21: Cell cycle analysis and apoptosis of the Her2/neu-resistant mamma carcinoma cell line JIMT-1 treated with a combination of D,L-methadone and doxorubicin. The human JIMT-1 cell line was treated with 1, 3 or 10 µg/mL of methadone alone (1, 3, 10 Met−Doxo), with 0.015 µg/mL of doxorubicin (Doxo) or a combination of 0.015 µg/mL of doxorubicin with 1, 3 or 10 µg/mL of methadone (1, 3, 10 Met+Doxo). (A) A FACS analysis of the cells revealed that the combination of both substances dose-dependently increased apoptosis of the JIMT-1 cells at 96 hours after treatment. (B) A FACS analysis performed at 96 hours (left side of the figure) and 120 hours (right side of the figure) after treatment showed further increased levels of apoptosis due to combination treatment. 0 or 0.015 µg/ml doxorubicin (black bars), 1 µg/mL methadone plus 0 or 0.015 µg/ml doxorubicin (white bars), 3 µg/mL methadone plus 0 or 0.015 µg/ml doxorubicin (hatched bars), 10 µg/mL methadone plus 0 or 0.015 µg/ml doxorubicin (doted bars).

Figure 22:
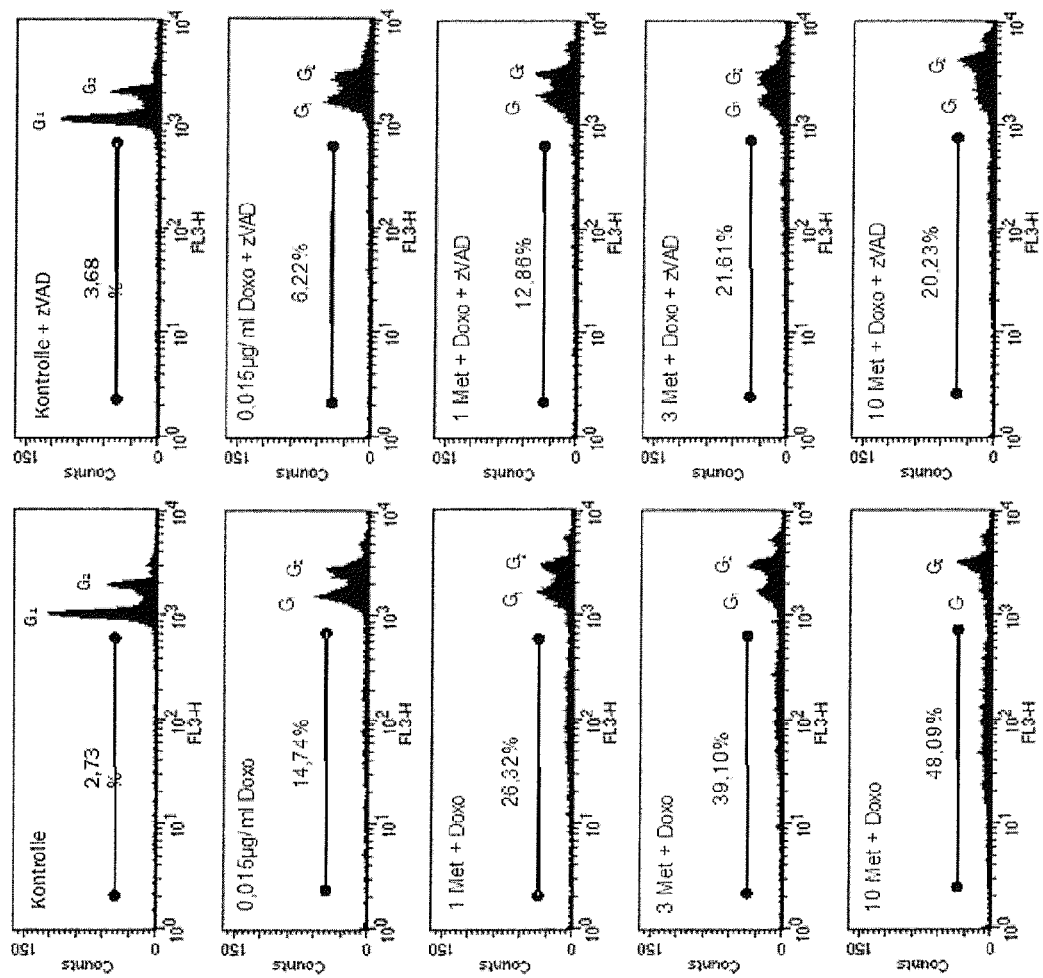
Figure 22:
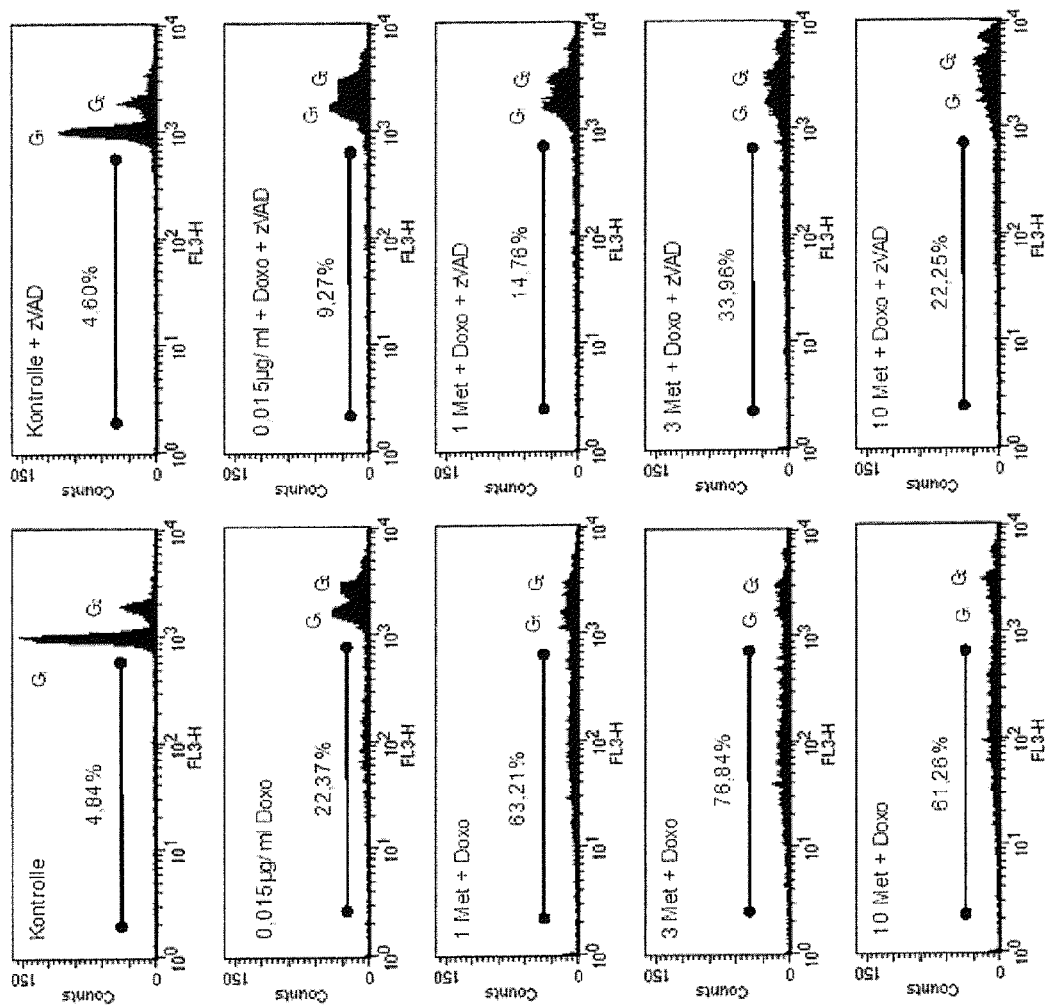

FIG. 22: Cell death induction of JIMT-1 cells using D,L-methadone and doxorubicin cotreatment depends on caspases activation. Inhibition of caspase activation with the broad spectrum caspase inhibitor zVAD.fmk blocks apoptosis induced by cotreatment of D,L-methadone and doxorubicin in JIMT-1 cells. The human cell line JIMT-1 was treated with different concentrations of D,L-methadone (10, 3, 1 µg/mL) in combination with 0.015 µg/mL doxorubicin (+0.015 µg/mL Doxo) in the absence (left sided diagrams) or presence of 50 µmol/L of zVAD.fmk (diagrams on the right side). At 96 hours (A) or 120 hours (B) after addition of the drug combination, the cells were analysed using flow cytometry.

Figure 23:
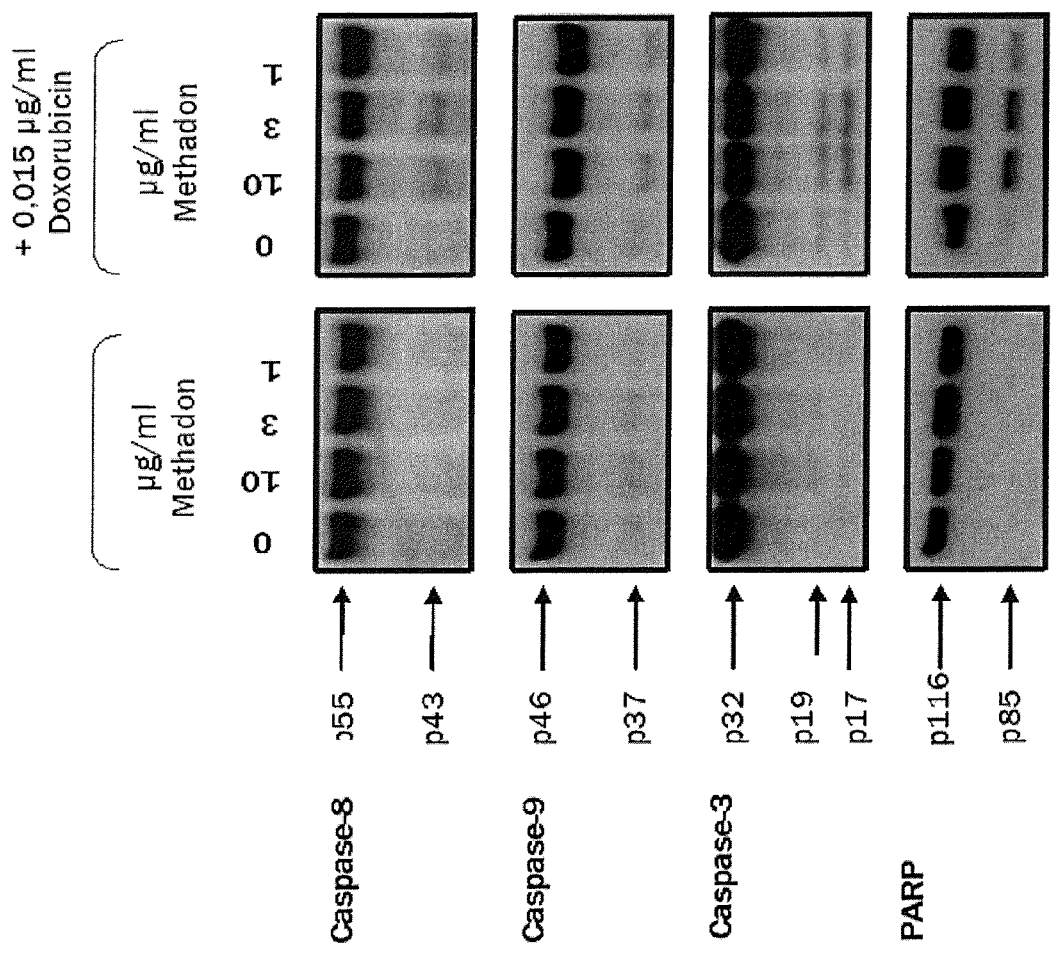
Figure 23:
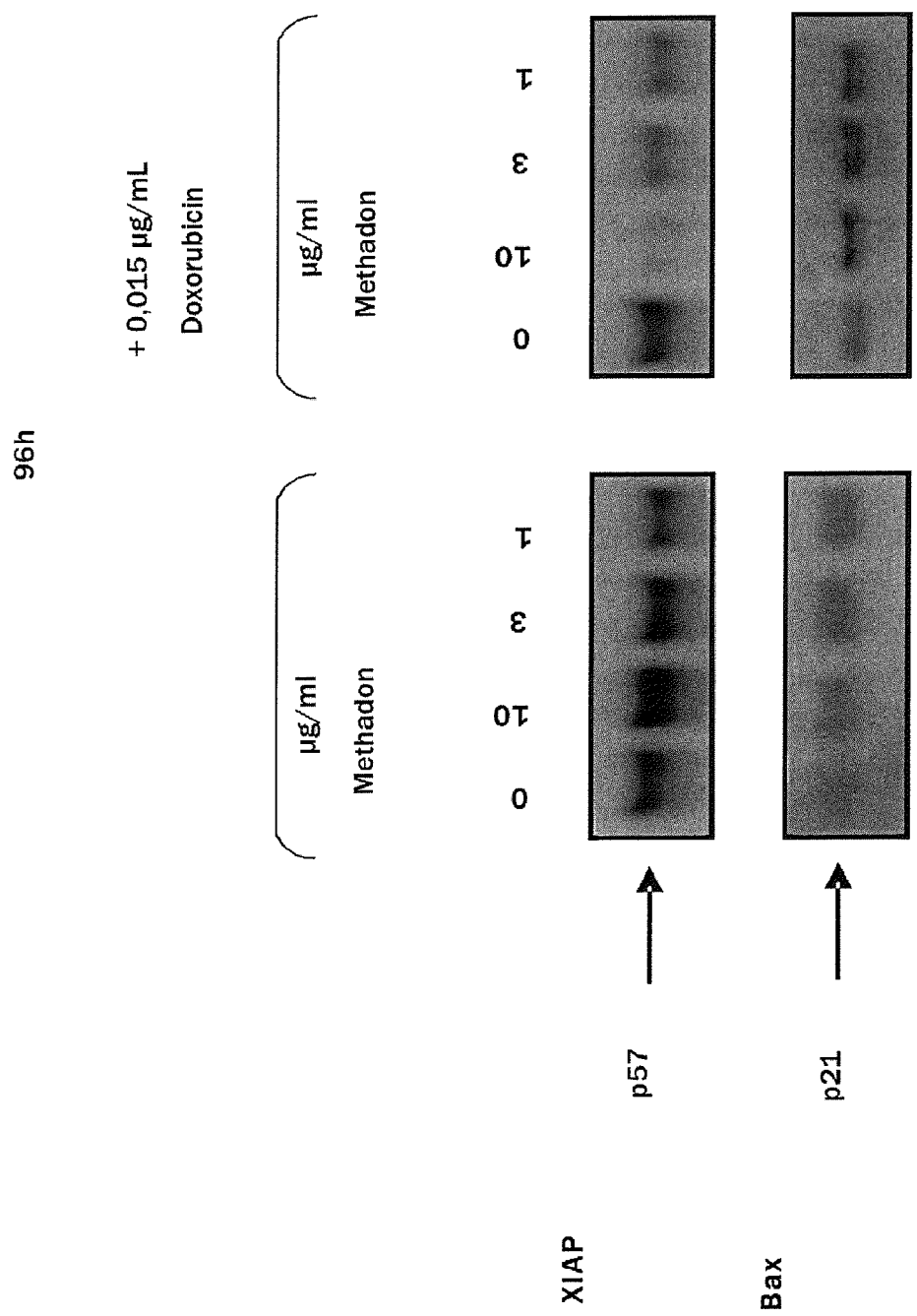

FIG. 23: Cell death induction of JIMT-1 cells using D,L-methadone and doxorubicin cotreatment depends on caspases activation. (A) D,L-methadone restored deficient caspases activation by doxorubicin in JIMT-1. A172 were treated with different concentrations of D,L-methadone (10, 3, 1 µg/mL) alone, with 0.015 µg/mL doxorubicin alone or with different concentrations of D,L-methadone (10, 3, 1 µg/mL) in addition to 0.015 µg/ml doxorubicin. After 96 h Western blot analyses for caspase-8, -9, -3 and PARP were performed. The active fragment of caspase-8 was detected at ~43 kDa, the active fragment of caspase-9 was detected at ~37 kDa, the active fragment of caspase-3 at ~17 kDa and PARP cleavage at ~85 kDa. Equal protein loading was controlled by anti-β-actin antibody. (B) Downregulation of XIAP and Bcl-$x_L$ in JIMT-1 cells by using D,L-methadone in combination with doxorubicin. Mamma carcinoma cells JIMT-1 were treated with different concentrations of D,L-methadone (10, 3, 1 µg/mL) alone, with 0.015 µg/mL doxorubicin alone or with D,L-methadone (10, 3, 1 µg/mL) in addition to doxorubicin (0.015 µg/mL Doxo) for 96 h. Western blot analyses for XIAP and Bcl-$x_L$ were performed. XIAP was detected at 57 kDa and Bcl-$x_L$ was detected at 21 kDa. Equal protein loading was controlled by anti-β-actin antibody.

Figure 24:
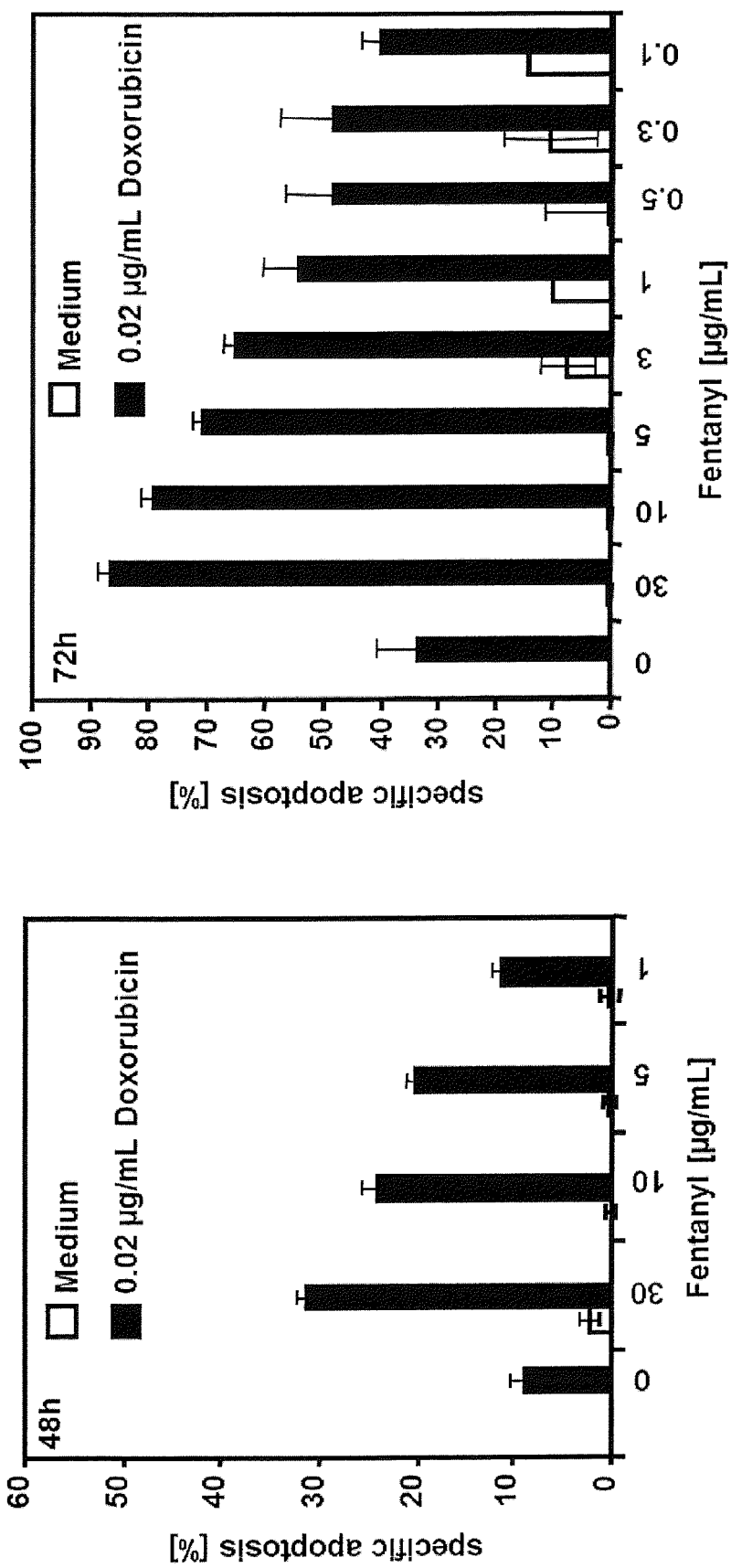

FIG. 24: Induction of apoptosis in T-Cell leukemia CEM cells by a combination of doxorubicin and fentanyl. Human T-Cell leukemia CEM cell line (10000 cells/100 µl) were treated with 30, 10, 5, 3, 1, 0.5, 0.3, 0.1 µg/mL fentanyl alone (white bars) or in addition to 0.02 µg/mL doxorubicin (black bars). After 48 h and 72 h quantification of apoptosis was measured by flow cytometry.

Figure 25:
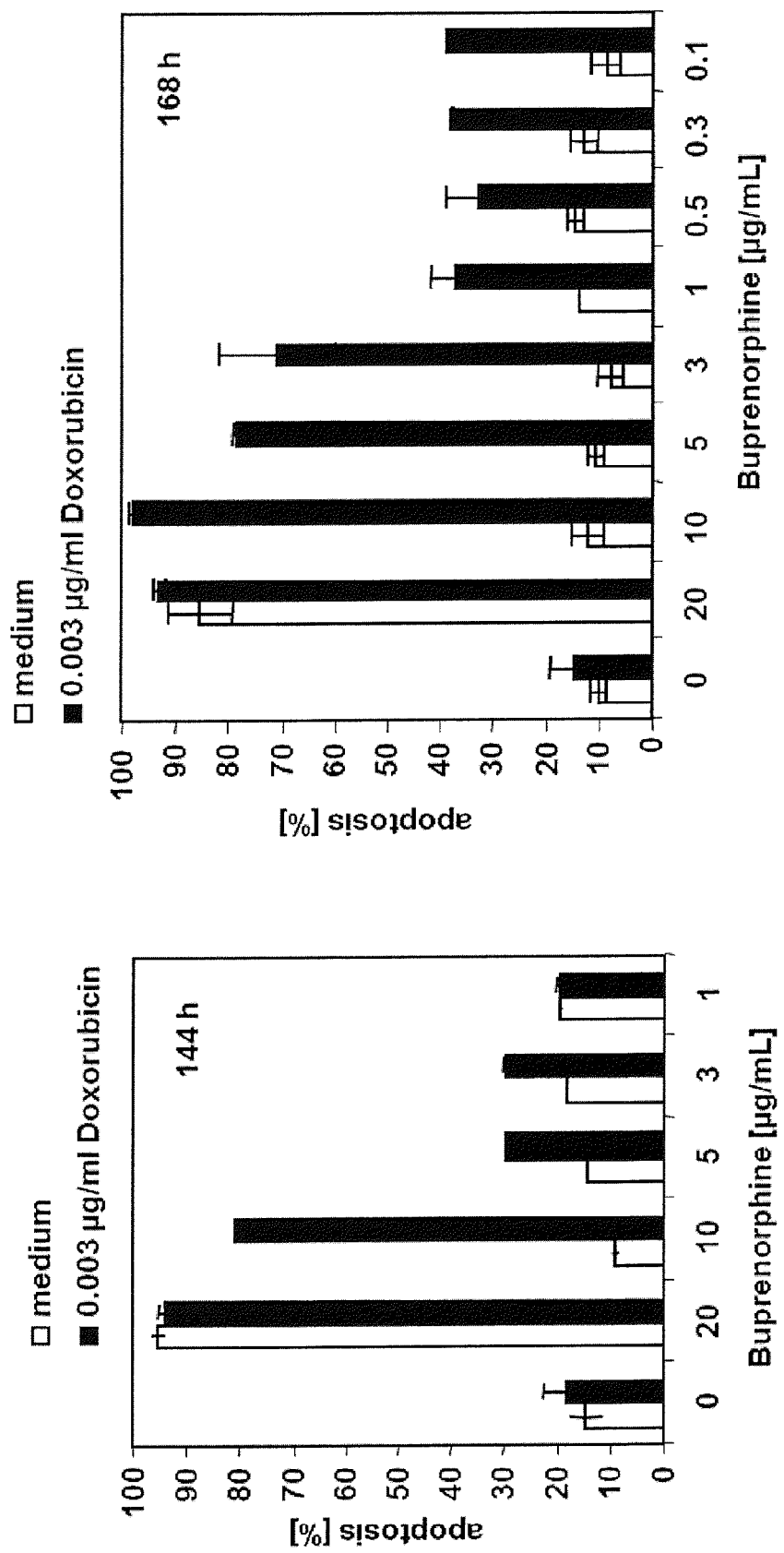

FIG. 25: Induction of apoptosis in human acute myeloid leukemia HL-60 cells by a combination of doxorubicin and buprenorphine. Human acute myeloid leukemia HL-60 cell line (5000 cells/100 µl) were treated with 20, 10, 5, 3, 1, 0.5, 0.3, 0.1 µg/mL buprenorphine alone (white bars) or in addition of 0.003 µg/mL doxorubicin (black bars). After 144 h or 168 h quantification of apoptosis was measured by flow cytometry.

Figure 26:
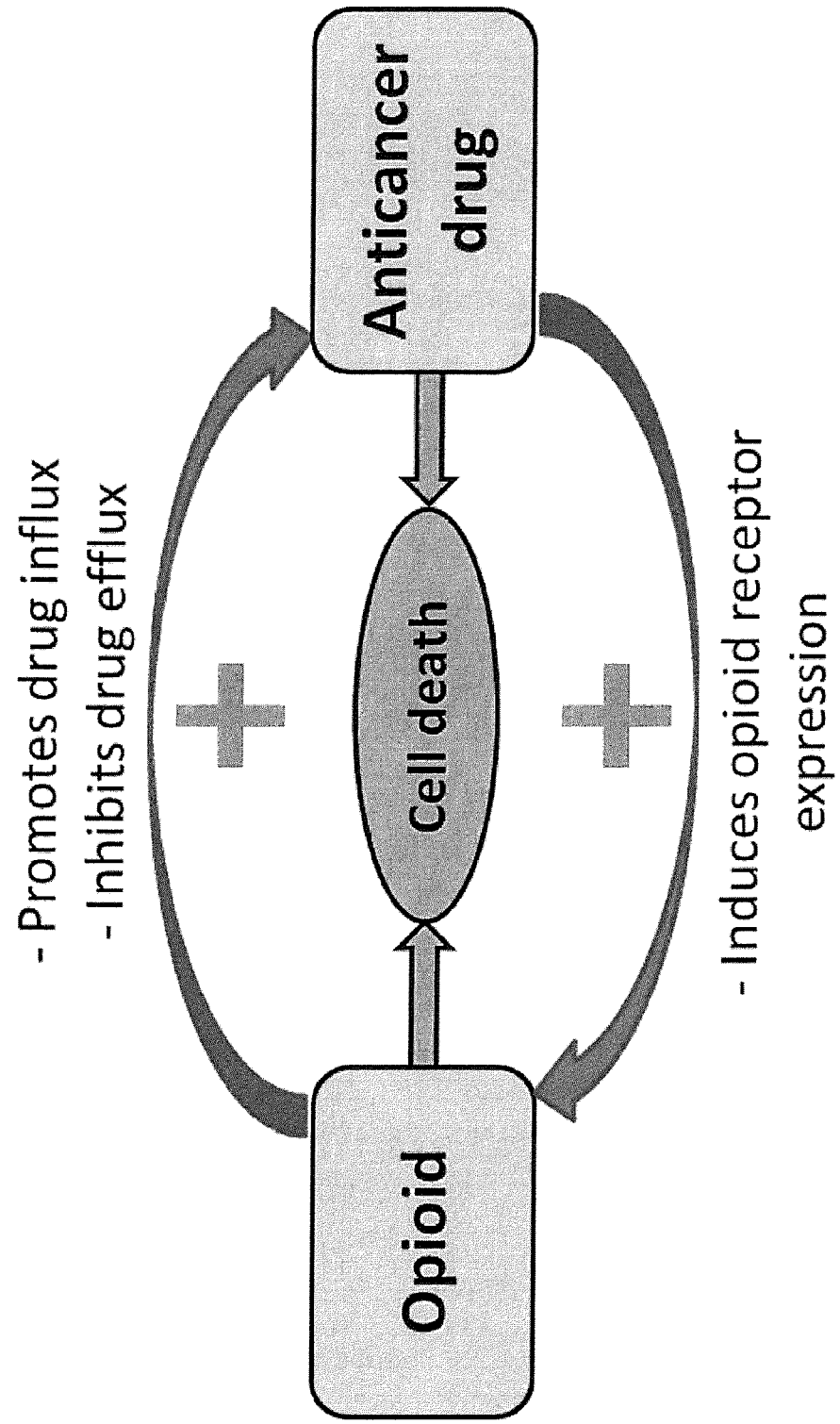

FIG. 26: Schematic diagram showing the mutual positive interaction between opioids and anticancer drugs. On one side, opioids enhance the cellular uptake and inhibit the efflux of anticancer drugs. On the other sides anticancer drugs lead to an increased expression of opioid receptors. Hence, both agents can exert their cytotoxic potential to a higher extent.

Figure 27:
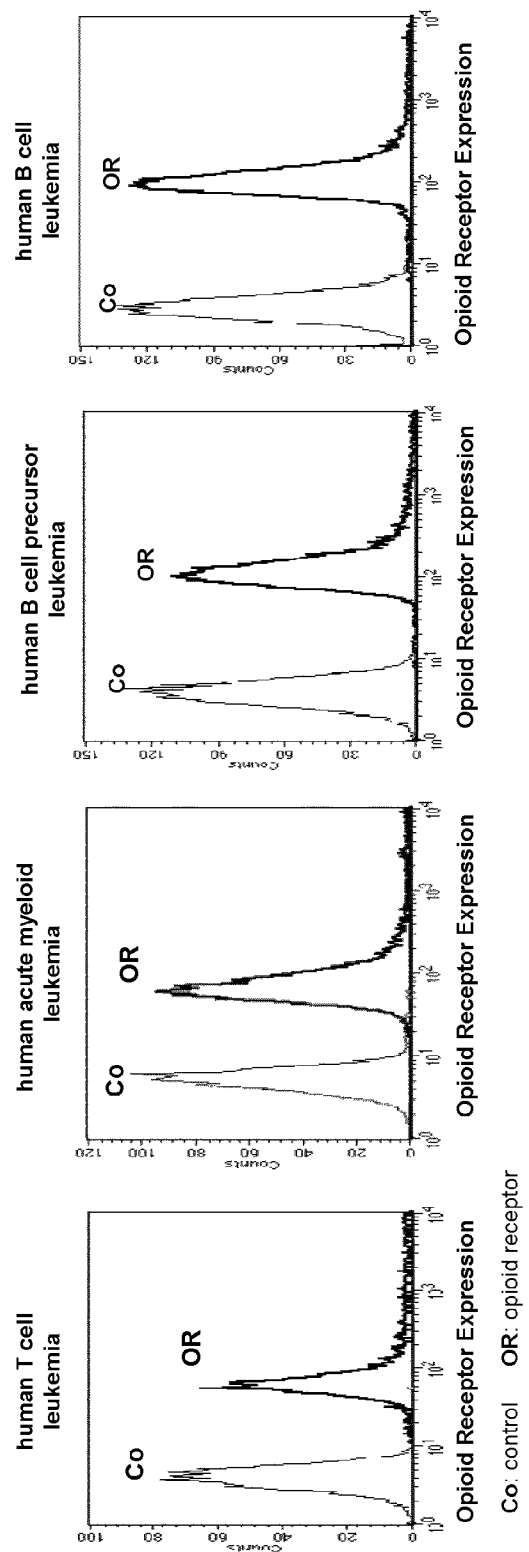

FIG. 27: Opioid receptor expression on different leukemia

Different leukemia cells (human T cell leukemia, human acute myeloid leukemia, human B cell precursor leukemia and human B cell leukemia) express different moderate number of opioid-receptors on their cell surface. Leukemia cells were stained with naloxone-fluoresceine measuring opioid-receptor expression (OR, thick black curve) and analyzed by flowcytometry. Controls (Co) without naloxone are exhibited as thin black curves.

Figure 28:
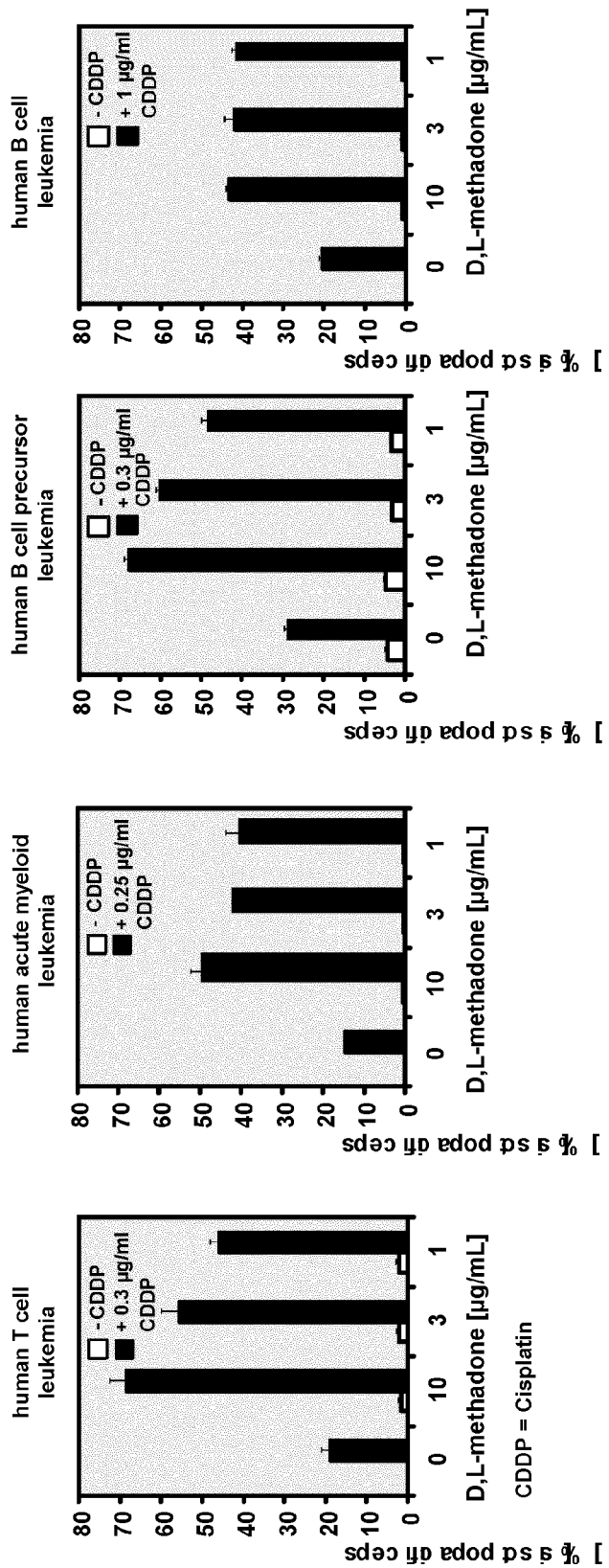

FIG. 28: Effect of combination therapy of opioid receptor agonist and anticancer agent D,L-methadone strongly enhances cisplatin sensitivity of different leukemia cells. Different leukemia cells (human T cell leukemia, human acute myeloid leukemia, human B cell precursor leukemia and human B cell leukemia) were treated with different concentrations of D,L-methadone (as indicated) alone (−CDDP, white columns) with cisplatin alone or with D,L-methadone in addition to cisplatin (+CDDP, black columns). After time of incubation, the percentages of apoptotic cells were measured by FSC/SSC-analysis. The percentage of specific apoptosis was calculated as described in FIG. 1B. Columns, mean of triplicates; bars, SD<10%.

Figure 29:
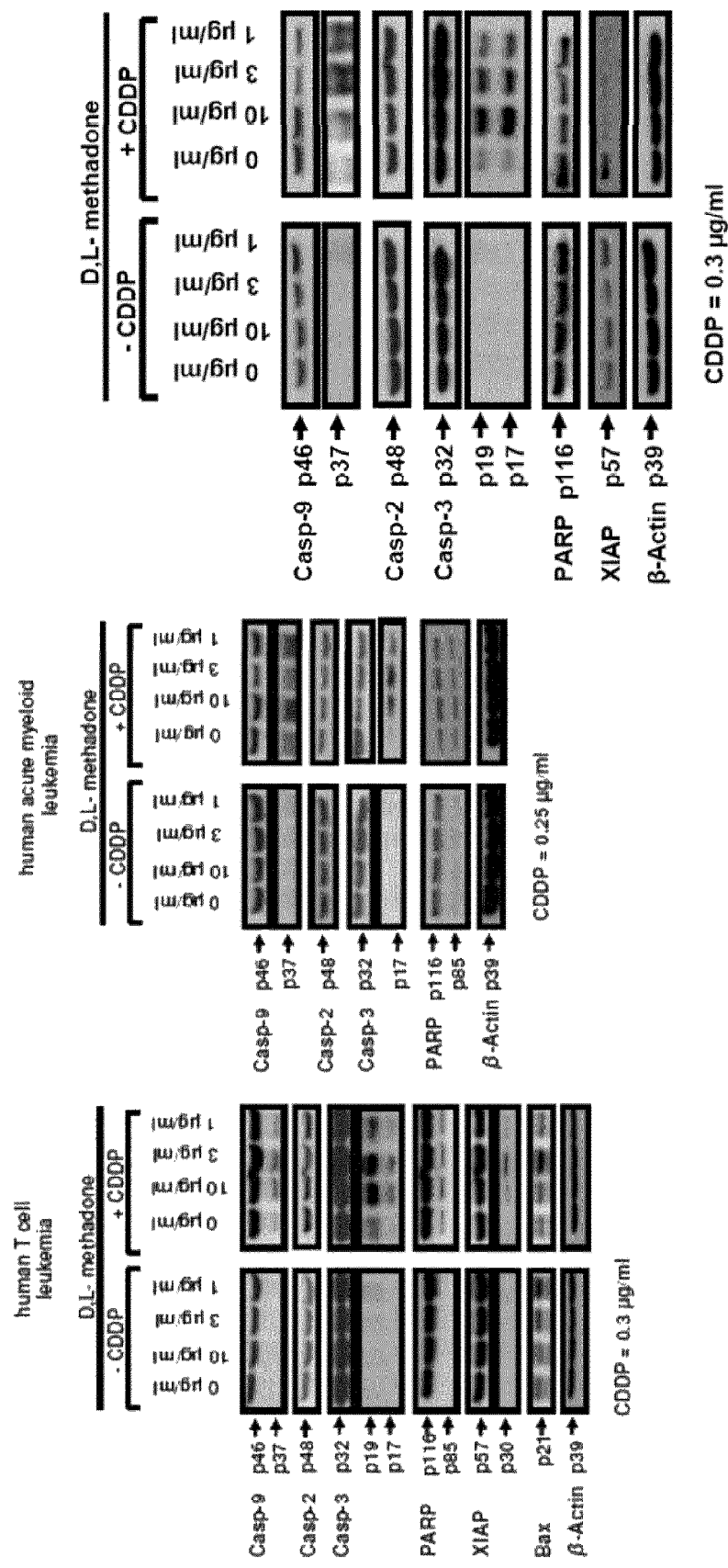

FIG. 29: D,L-methadone in combination with cisplatin restores deficient activation of apoptotic pathways in leukemia cells. D,L-methadone and cisplatin co-treatment provokes caspases activation and induces downregulation and cleavage of XIAP and upregulation of Bax. Different leukemia cells (human T cell leukemia, human acute myeloid leukemia, human B cell precursor leukemia) were treated with D,L-methadone (as indicated) alone (−CDDP), with cisplatin (CDDP) alone or with D,L-methadone (as indicated) in addition to cisplatin (+CDDP). After time of incubation Western blot analyses for caspase-2, caspase-9, caspase-3, PARP, XIAP and Bax were performed. Downregulation of procaspase-2 was detected at ~48 kDa. The active fragment of caspase-9 was detected at ~37 kDa, the active fragment of caspase-3 at ~19 kDa and or ~17 kDa, PARP at ~116 kDa, PARP cleavage at ~85 kDa, XIAP was detected at ~58 kDa and XIAP cleavage at ~30 kDa and Bax at ~21 kDa. Equal protein loading was controlled by anti-β-actin antibody.

Figure 30:
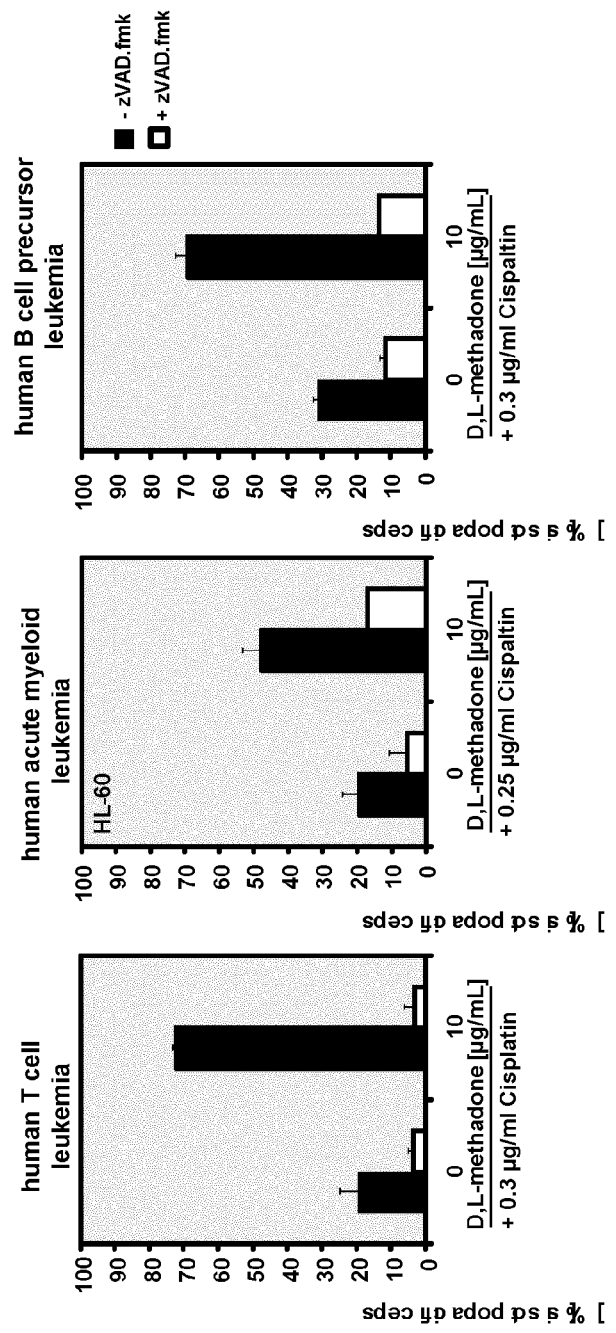

FIG. 30: D,L-methadone and cisplatin-induced apoptosis depends on caspase activation. Pre-incubation of different leukemia cells (human T cell leukemia, human acute myeloid leukemia, human B cell precursor leukemia) with 50 µM of the caspase inhibitor zVAD.fmk for 1 h (+zVAD.fmk, white columns) or without pre-treatment (−zVAD.fmk, black columns) was followed by addition of D,L-methadone (as indicated) in combination with cisplatin (as indicated). Apoptosis induction was detected after time of incubation by FSC/SSC-analysis. The percentage of specific apoptosis was calculated as described in FIG. 1B. Columns, mean of triplicates; bars, SD<10%.

Figure 31:
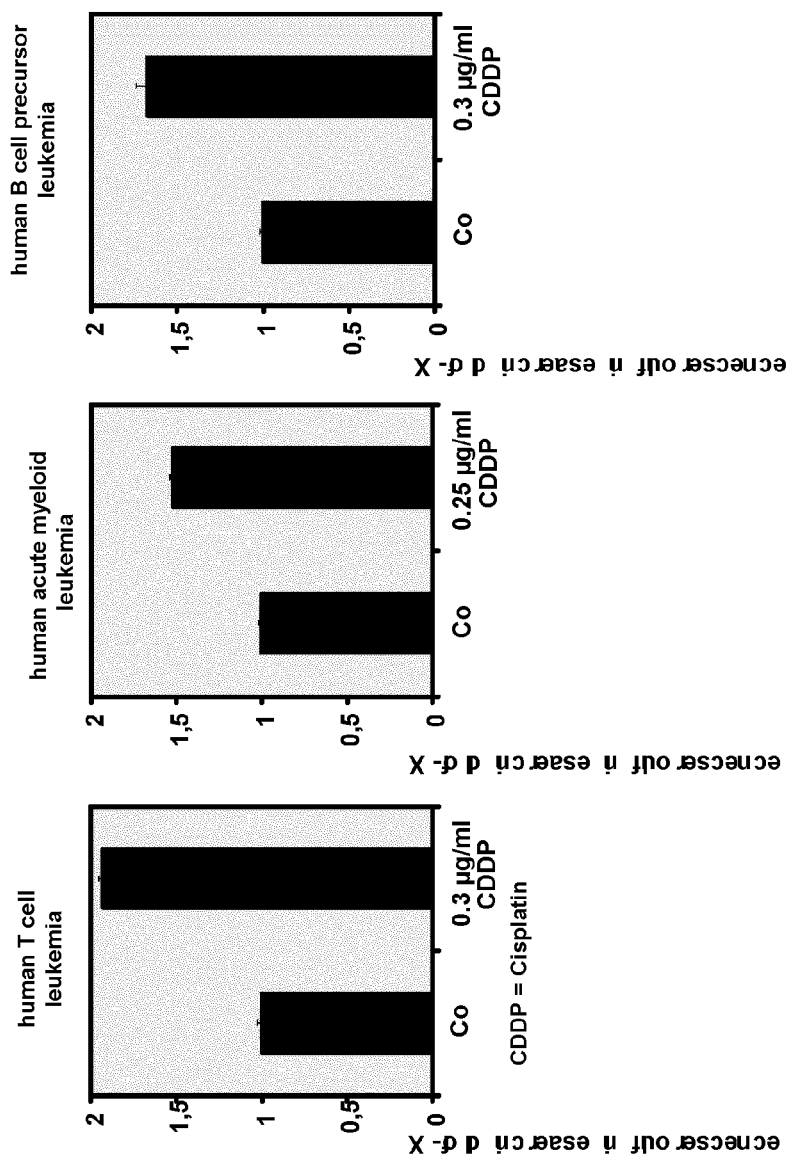

FIG. 31: Cisplatin enhances opioid receptor expression. (A) Cisplatin enhances opioid receptor expression on the cells' surface of different leukemia cells (human T cell leukemia, human acute myeloid leukemia and human B cell precursor leukemia) were treated with cisplatin (as indicated). After staining of cisplatin-treated cells (CDDP) and untreated cells (Co) with naloxone-fluoresceine relative fluorescence intensities were determined flowcytometrically. X-fold increase in opioid receptor expression compared to the untreated control group is shown after subtracting the cells' autofluorescence and cisplatin fluorescence.

Figure 32:
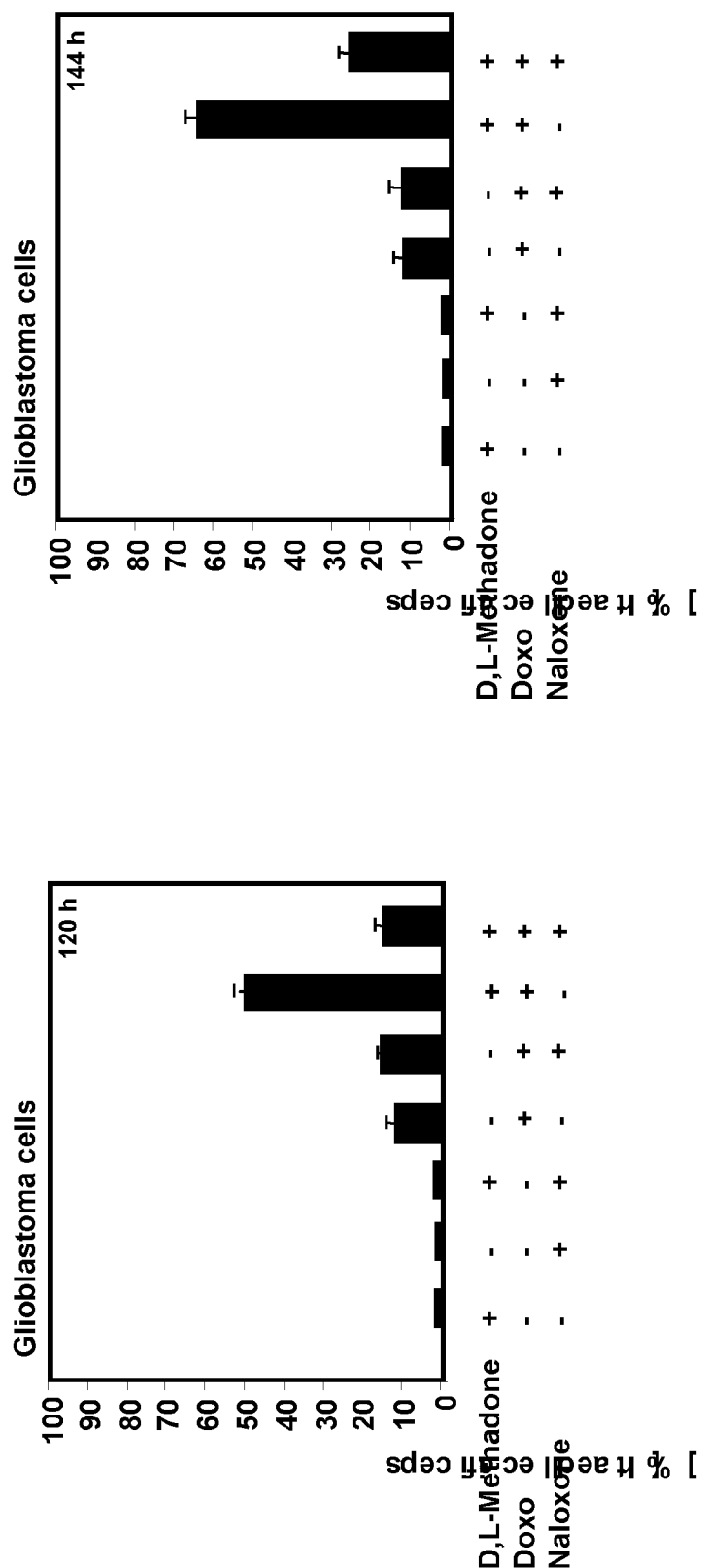

FIG. 32: Combination treatment with D,L-methadone and doxorubicin induced apoptosis depends on opioid-receptor triggering. Inhibition of opioid-receptor triggering inhibits apoptosis induction mediated by combination treatment with D,L-methadone and doxorubicin. Glioblastoma cells were incubated with 60 µg/mL naloxone (Naloxone), 3 µg/mL D,L-methadone (D,L-Methadone) and 0.1 µg/mL doxorubicin (Doxo) alone or in different combinations as indicated by the marks +and −. After 120 h and 144 h, the percentages of apoptotic cells were measured by FSC/SSC-analysis. The results of the different treatments which are indicated concerning the given substances under the single bars after 120 h (left side of the figure) and 144 h (right side of the figure) are shown in FIG. 32.

Figure 33:
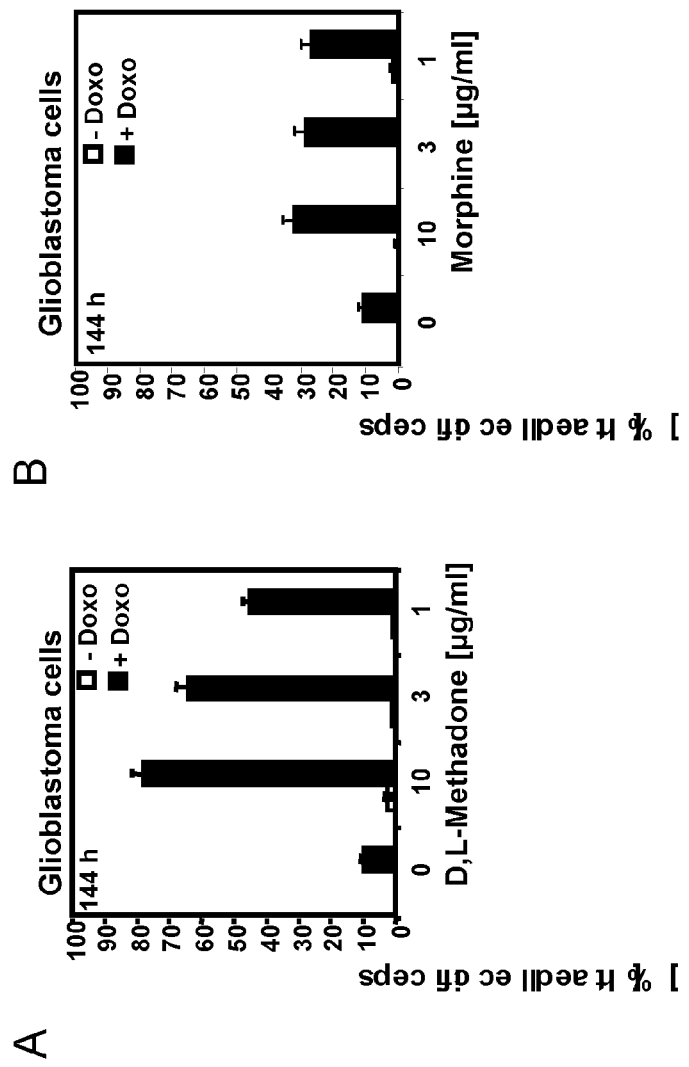

FIG. 33: Different duration of effectiveness of different opioids induces different rates of cell death in glioblastoma cells.

A) Glioblastoma cells were treated with different concentrations of D,L-methadone (as indicated) alone (−Doxo, white columns, which are very low and on the left side of a black bar), with doxorubicin alone or with D,L-methadone (as indicated) in addition to doxorubicin (+Doxo, black columns) using the same concentration of 0.1 µg/mL doxorubicin for all treatments and different concentrations of D,L-methadone as indicated. 144 h after stimulation, percentages of cell death and apoptotic cells were measured by hypodiploid DNA analysis.

B) Glioblastoma cells were treated with different concentrations of morphine (as indicated) alone (−Doxo, white columns which are very low and on the left side of a black bar), with doxorubicin alone or with morphine (as indicated) in addition to doxorubicin (+Doxo, black columns) using the same concentration of 0.1 µg/mL doxorubicin for all treatments and different concentrations of D,L-methadone as indicated. 144 h after stimulation, percentages of cell death and apoptotic cells were measured by hypodiploid DNA analysis.

The percentage of specific cell death was calculated as described in FIG. 1B. Columns, mean of triplicates; bars, SD<10%.

Figure 34:
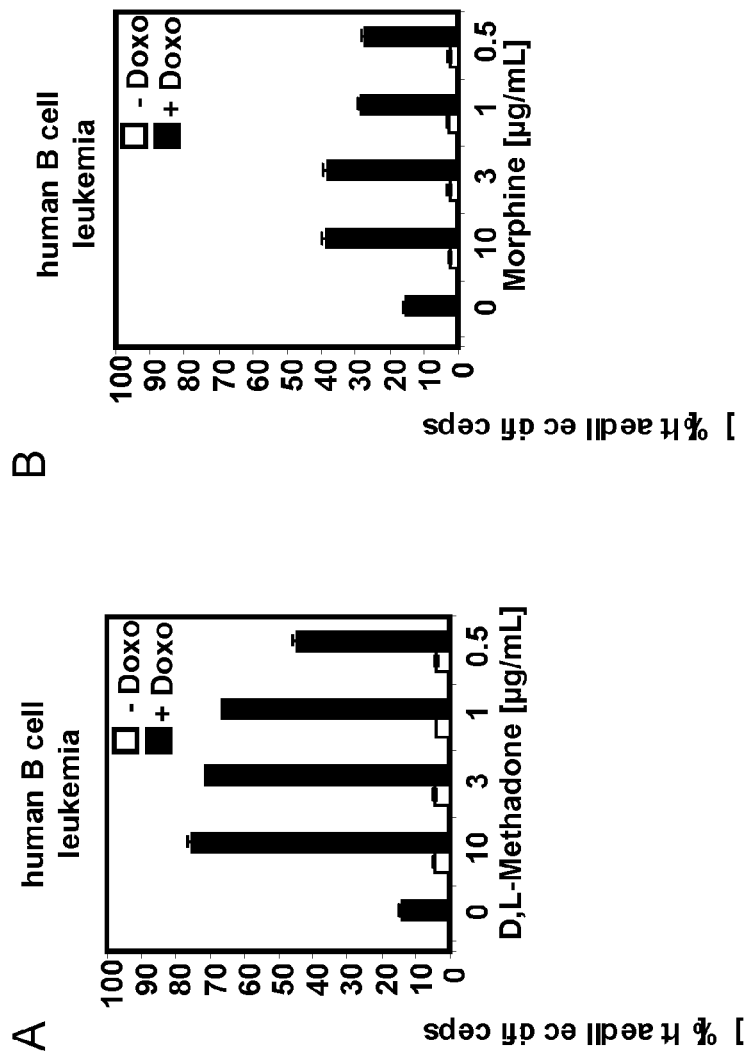

FIG. 34: Different duration of effectiveness of different opioids induces different rates of cell death in leukemia cells A) Leukemia cells (human B cell leukemia) were treated with different concentrations of D,L-methadone (as indicated) alone (−Doxo, white columns on the left side of a black bar), with doxorubicin alone or with D,L-methadone (as indicated) in addition to doxorubicin (+Doxo, black columns)) using the same concentration of 0.1 µg/mL doxorubicin for all treatments and different concentrations of D,L-methadone as indicated. 96 h after stimulation, percentages of apoptotic cells were measured by hypodiploid DNA analysis.

B) Leukemia cells (human B cell leukemia) were treated with different concentrations of morphine (as indicated) alone (−Doxo, white columns on the left side of a black bar), with doxorubicin alone or with morphine (as indicated) in addition to doxorubicin (+Doxo, black columns) using the same concentration of 0.1 µg/mL doxorubicin for all treatments and different concentrations of D,L-methadone as indicated. For the 96 h after stimulation, percentages of apoptotic cells were measured by hypodiploid DNA analysis.

The percentage of specific apoptosis was calculated as described in FIG. 1B. Columns, mean of triplicates; bars, SD<10%.

Figure 35:
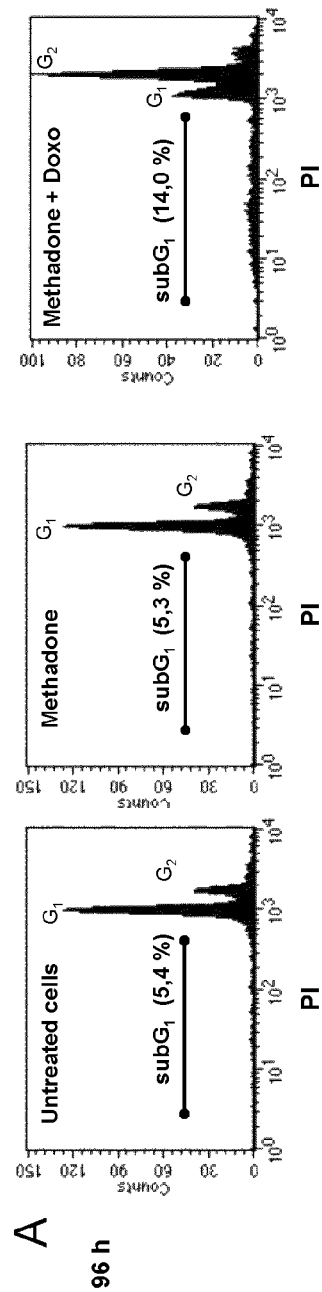

FIG. 35: Combination treatment with D,L-methadone and doxorubicin inhibits proliferation and induces S/G2-M cell cycle arrest in glioblastoma cells. Flow cytometric analysis of glioblastoma cells treated with methadone and doxorubicin was shown. Flow cytometric analysis of untreated cells (Untreated cells) (G1 peak is higher than G2 peak), cells treated with 1 µg/ml methadone (Methadone) (G1 peak is higher than G2 peak) and cells treated with methadone in addition to 0.1 µg/ml doxorubicin (Methadone+Doxo). Arrest of cell cycle progression at the G2/M phase (G1 peak lower than in untreated cells and G2 peak is higher than in untreated cells) was shown in glioblastoma cells treated with methadone in addition to doxorubicin after 96 h (A). subG1 peak in front of G1 is the fragmentated DNA (percentage of cell death). Results are representative of 3 independent experiments.

FIG. 36: Apoptosis induction and caspase activation depend on opioid receptor activation inducing cAMP downregulation in glioblastoma. Opioid receptor activation triggering downregulation of cAMP plays a critical role in sensitizing glioblastoma cells for doxorubicin treatment. (A, B) Blocking opioid receptor activation inhibits apoptosis induction. Glioblastoma cell line A172 was incubated with 100 µg/mL naloxone (Naloxone), 3 µg/mL D,L-methadone (D,L-Methadone) and 0.3 µg/mL doxorubicin (Doxo) alone or in different combinations as indicated. After (A) 120 h and (B) 144 h, the percentages of apoptotic cells were measured by hypodiploid DNA analysis. (C) Inhibition of opioid receptor-activation inhibits caspase activation. A172 cells were incubated with 100 µg/mL naloxone (Naloxone), 3 µg/mL D,L-methadone (D,L-Methadone) and 0.3 µg/mL doxorubicin (Doxo) alone or in different combinations as indicated. Western blot analyses for caspase-9, caspase-3 and PARP were performed after 120 h of incubation. The active fragment of caspase-9 was detected at ~37 kDa, of caspase-3 at ~19 kDa and ~17 kDa and PARP cleavage at ~85 kDa. Equal protein loading was controlled by anti-β-actin antibody. (D) Increasing cAMP levels via repression of phosphodiesterase activity inhibits apoptosis. A172 cells were incubated for 120 h with 25 µM 3-Isobutyl-1-methyl-xanthine (IBMX), 3 µg/mL D,L-methadone (D,L-Methadone) and 0.3 µg/mL doxorubicin (Doxo) alone or in different combinations as indicated. After 120 h, the percentages of apoptotic cells were measured by hypodiploid DNA analysis.

Figure 37:
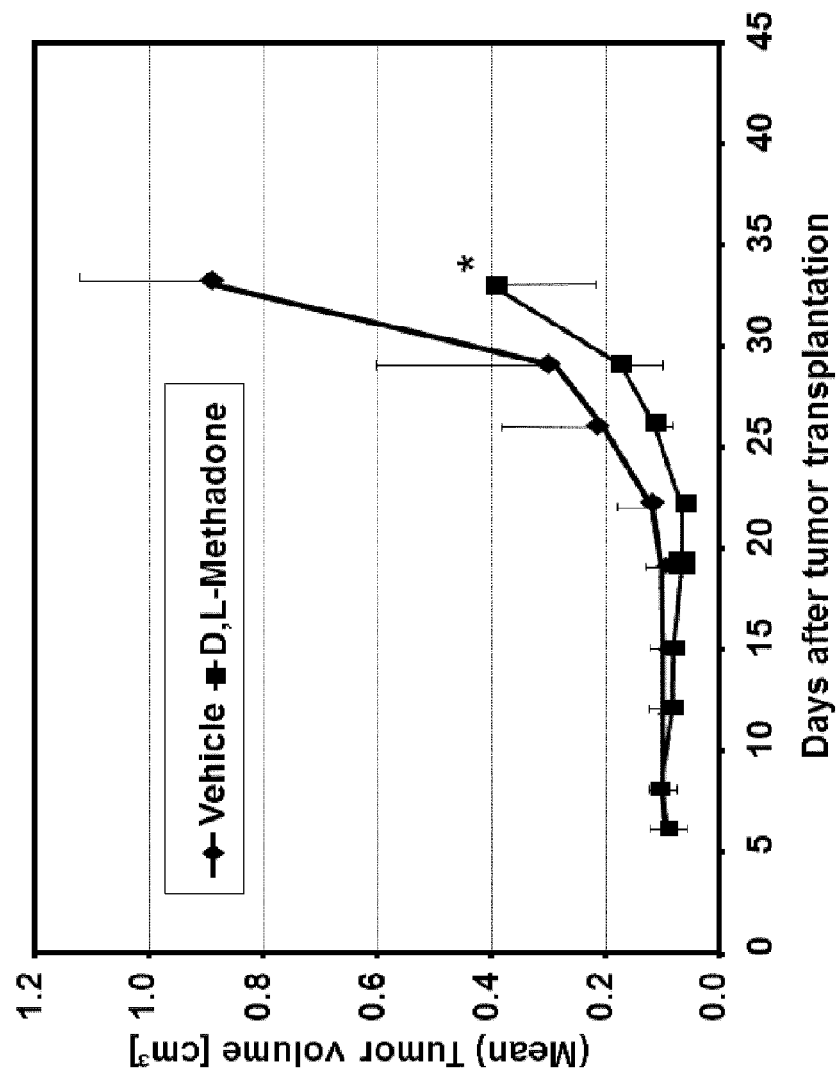

FIG. 37: D,L-Methadone inhibits tumour growth of glioblastoma. The glioblastoma cell line U87MG (U87) was transplanted into nude-mice. Mice were daily treated with D,L-methadone (n=8, black square) or the vehicle 10% Tween 80 in saline (n=8, black diamond). After transplantation mice were observed for 33 days. At distinct points in time (as indicated), tumour growth and tumour volume were measured. *Significant to control (p<0.05, Mann-Whitney U test).

Figure 38:
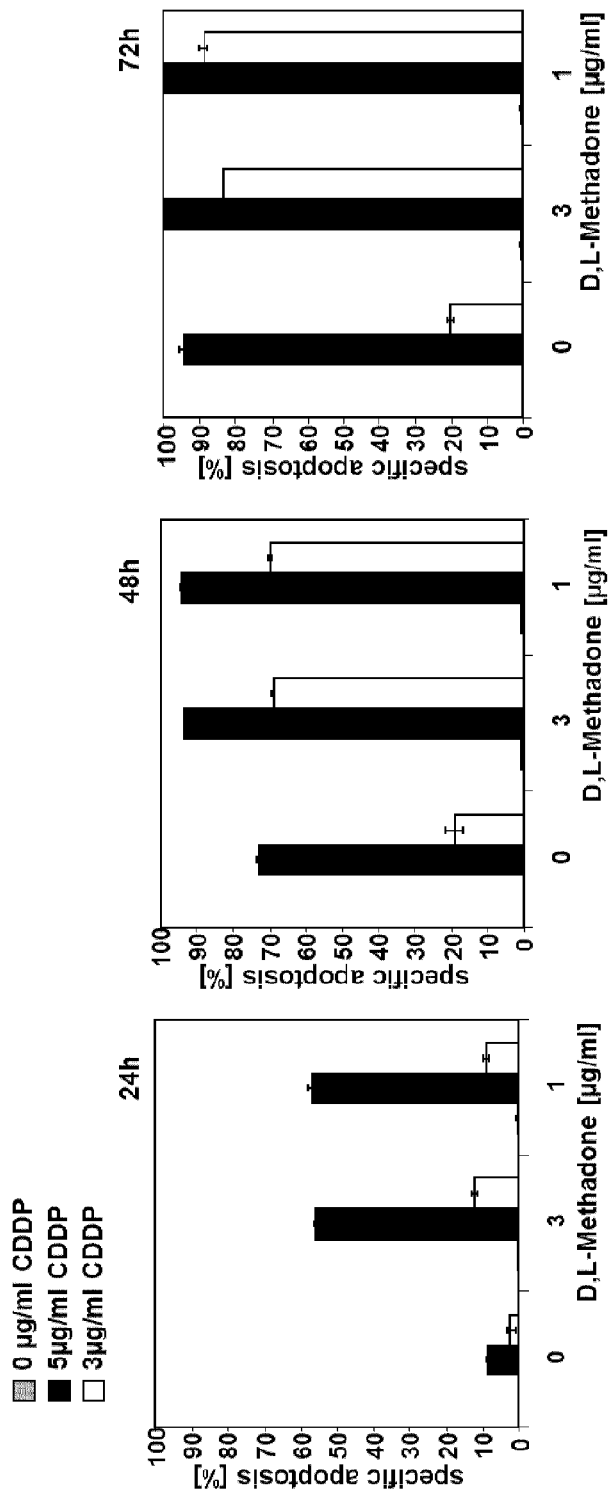

FIG. 38: D,L-methadone sensitizes ovarian cancer cells for short-term cisplatin treatment. A2780 ovarian cancer cells were treated with different concentrations of D,L-methadone (3, 1, 0 µg/mL) alone, with 5 or 3 µg/mL cisplatin alone or in combination with D,L-methadone and 5 µg/mL cisplatin (+5 µg/ml CDDP, black columns) or 3 µg/mL cisplatin (+3 µg/mL, white columns). After 24 h, 48 h and 72 h, the percentages of cell death/apoptotic cells were measured.

Figure 39:
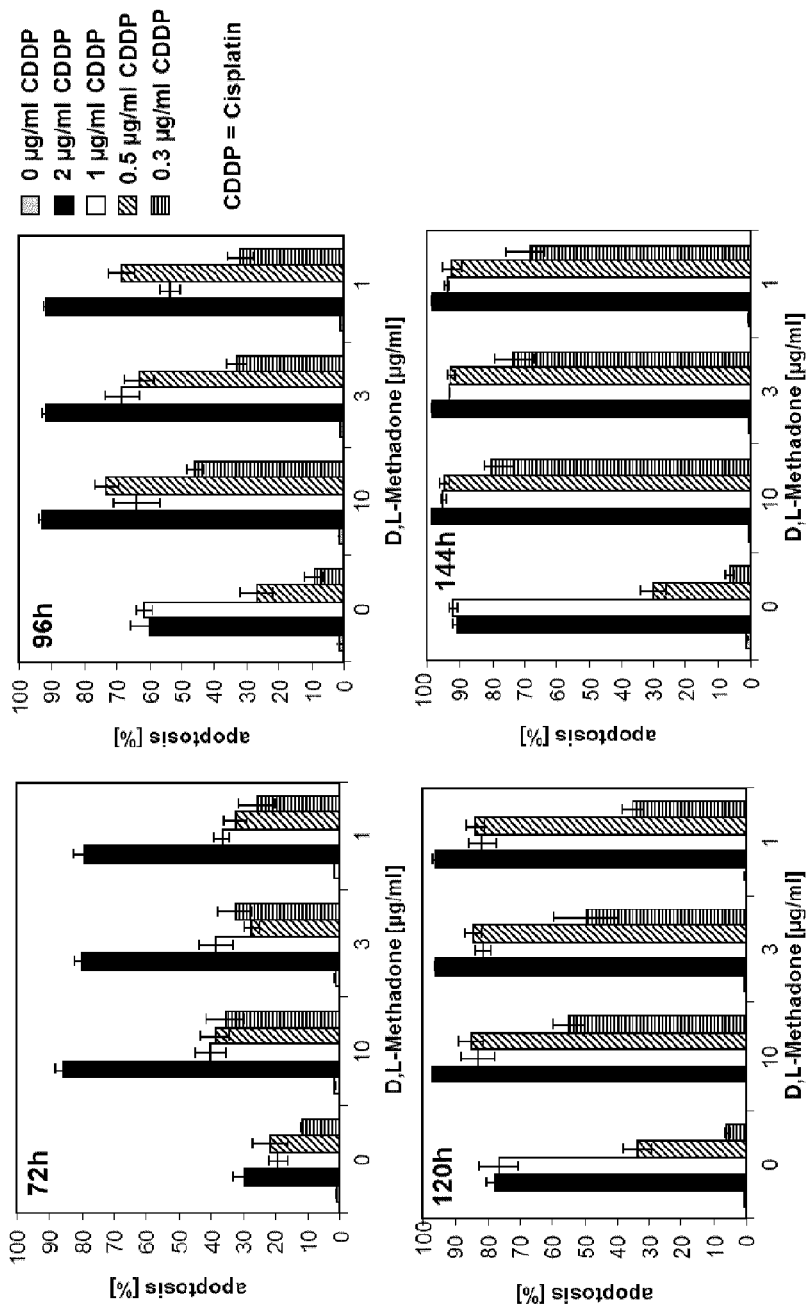

FIG. 39: D,L-methadone sensitizes ovarian cancer cells for long-term cisplatin treatment. A2780 ovarian cancer cells were treated with different concentrations of D,L-methadone (10, 3, 1, 0 µg/mL) alone, with cisplatin (2, 1, 0.5, 0.3 µg/mL) alone or in combination with D,L-methadone and cisplatin. After 72 h, 96 h, 120 h and 144 h, the percentages of cell death/apoptotic cells were measured.

Figure 40:
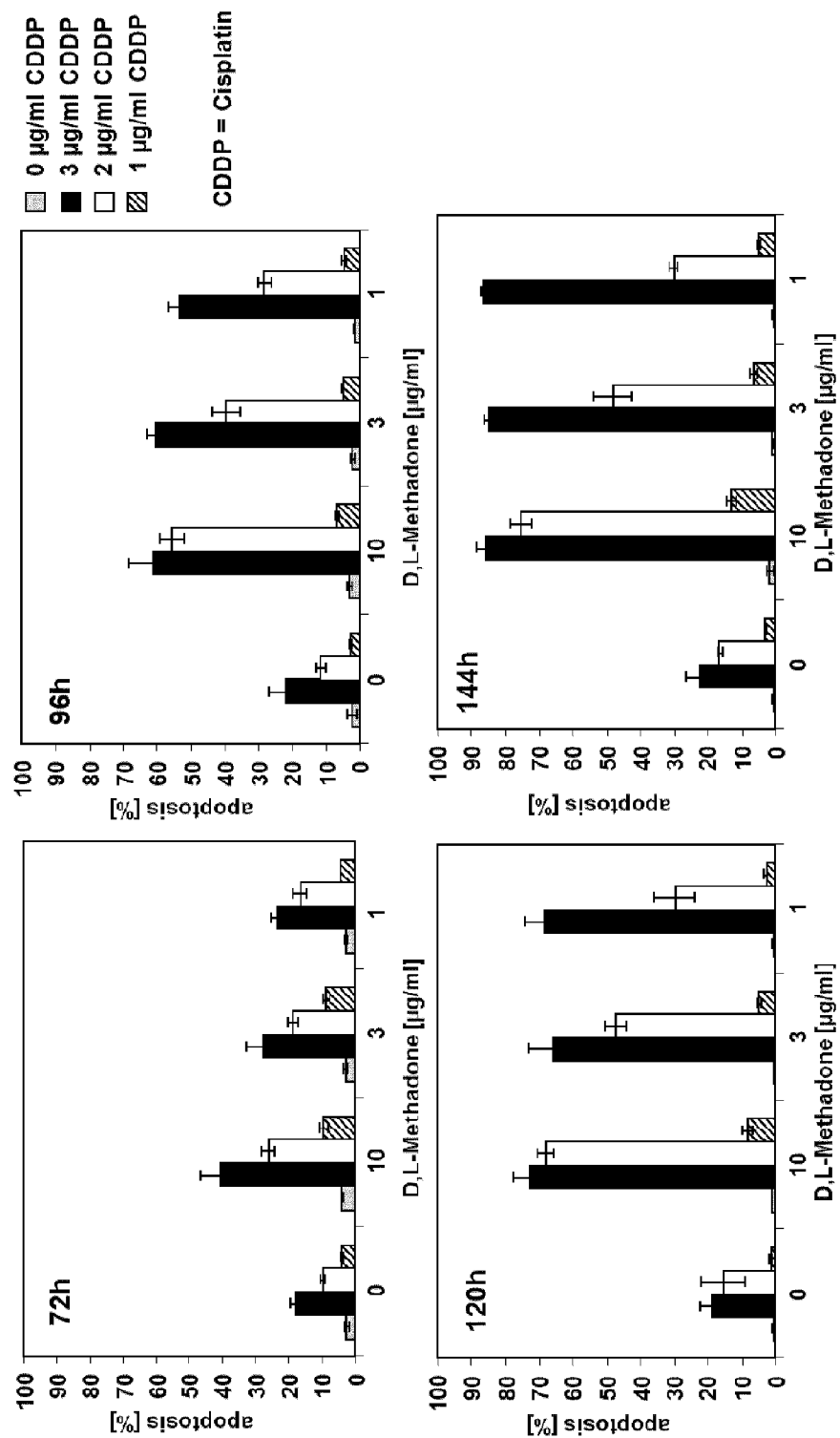

FIG. 40: D,L-methadone sensitizes cisplatin-resistant ovarian cancer cells for cisplatin treatment. A2780cis ovarian cancer cells were treated with different concentrations of D,L-methadone (10, 3, 1, 0 µg/mL) alone, with cisplatin (3, 2, 1 µg/mL) alone or in combination with D,L-methadone and cisplatin. After 72 h 96 h, 120 h and 144 h, the percentages of cell death/apoptotic cells were measured.

Figure 41:
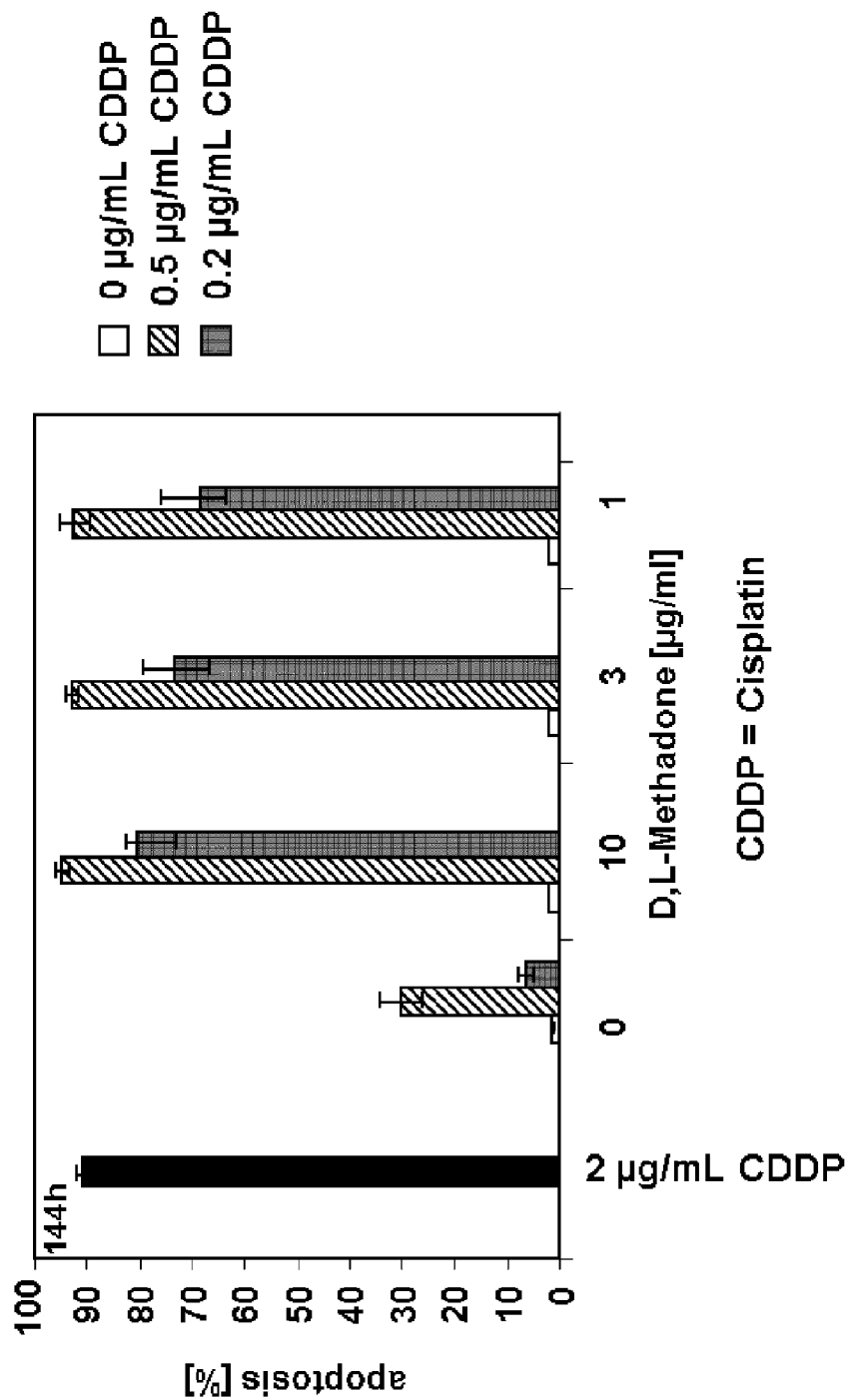

FIG. 41: D,L-methadone strongly sensitizes ovarian cancer cells for cisplatin treatment. A2780 ovarian cancer cells were treated with different concentrations of D,L-methadone (10, 3, 1, 0 µg/mL) alone, with 2 µg/mL cisplatin alone (black column) and with 0.5 or 0.2 µg/mL cisplatin (hatched and grey columns, respectively) in combination with D,L-methadone as indicated. After 144 h, the percentages of cell death/apoptotic cells were measured.

Figure 42:
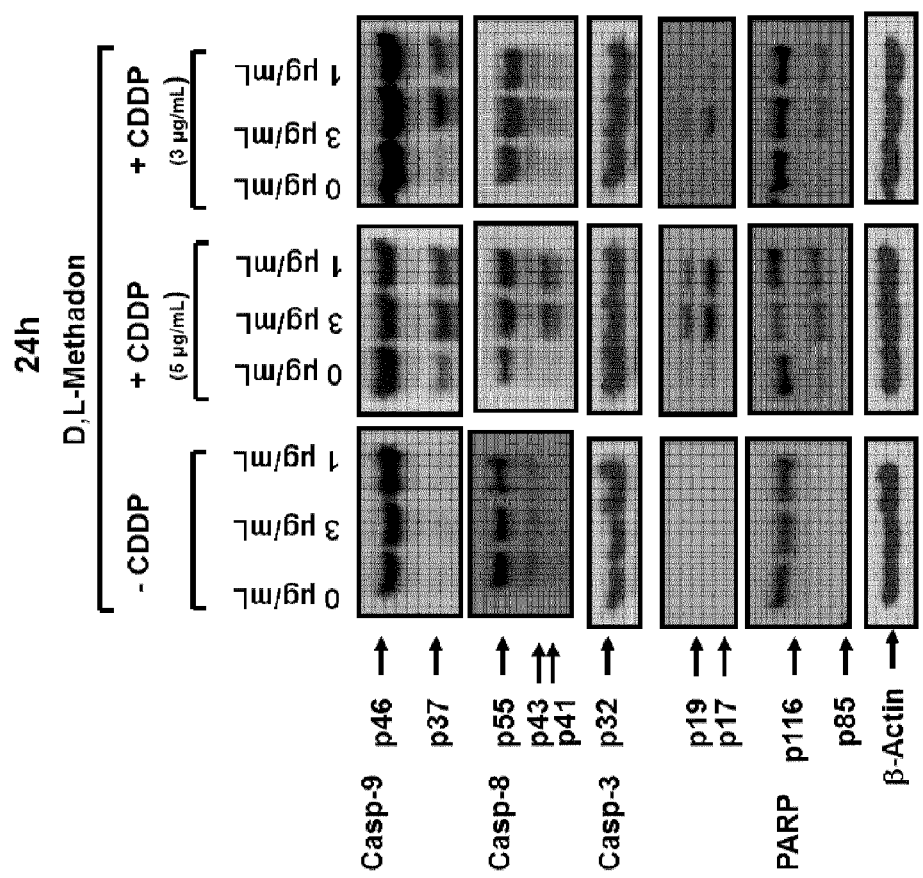

FIG. 42: Opioid receptor activation using D,L-methadone sensitizes ovarian cancer cells for cisplatin-induced activation of caspases. D,L-Methadone restored deficient caspases activation by cisplatin in ovarian cancer cells. A2780 ovarian cancer cells were treated with different concentrations of D,L-methadone (3, 1 µg/mL,−CDDP) alone, with 5 or 3 µg/mL cisplatin alone or with D,L-methadone (3, 1 µg/mL) in addition to 5 or 3 µg/mL cisplatin (+CDDP). After 24 h, Western blot analyses were performed. The active fragment of caspase-9 was detected at ~37 kDa, the active fragment of caspase-3 at ~19 and 17 kDa, active fragment of caspase-8 was detected at ~43 and 41 kDa and PARP cleavage at ~85 kDa. Equal protein loading was controlled by anti-β-actin antibody.

Figure 43:
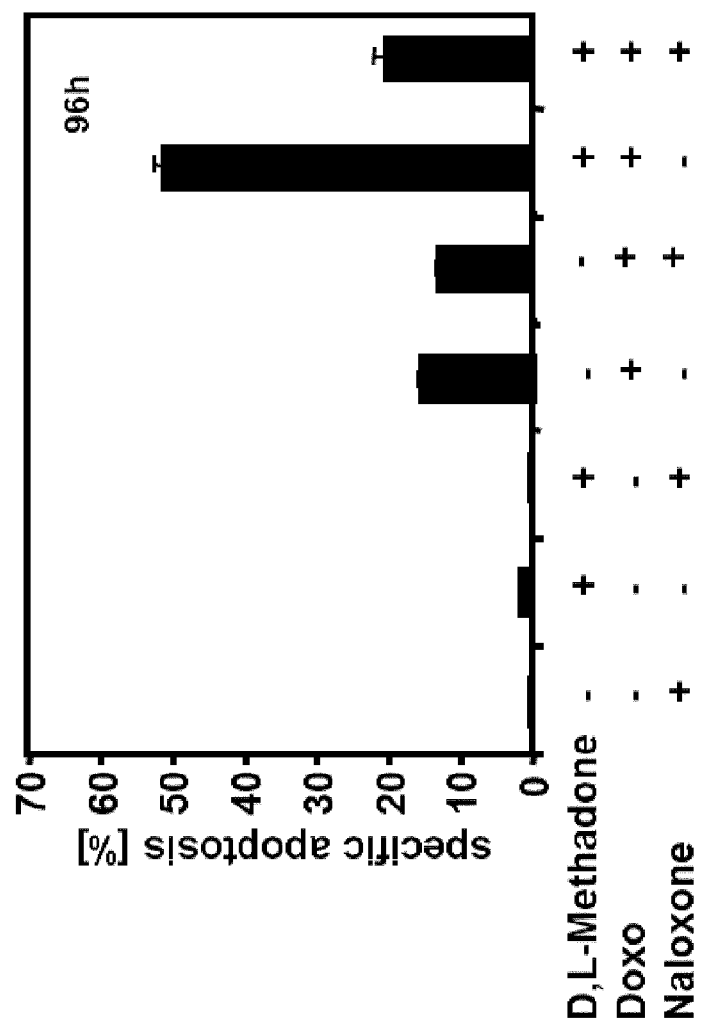

FIG. 43: Opioid receptor activation using D,L-methadone plays a critical role in sensitizing breast cancer cells for doxorubicin treatment. Blocking opioid receptor activation using opioid antagonist naloxone strongly inhibits apoptosis induction induced by combination treatment with D,L-methadone and doxorubicin. Breast cancer cells JIMT-1 incubated with 100 µg/mL naloxone (Naloxone), 10 µg/mL D,L-methadone (D,L-Methadone) and 0.01 µg/mL doxorubicin (Doxo) alone or in different combinations as indicated. After 96 h, the percentages of cell death/apoptotic cells were measured.

Figure 44:
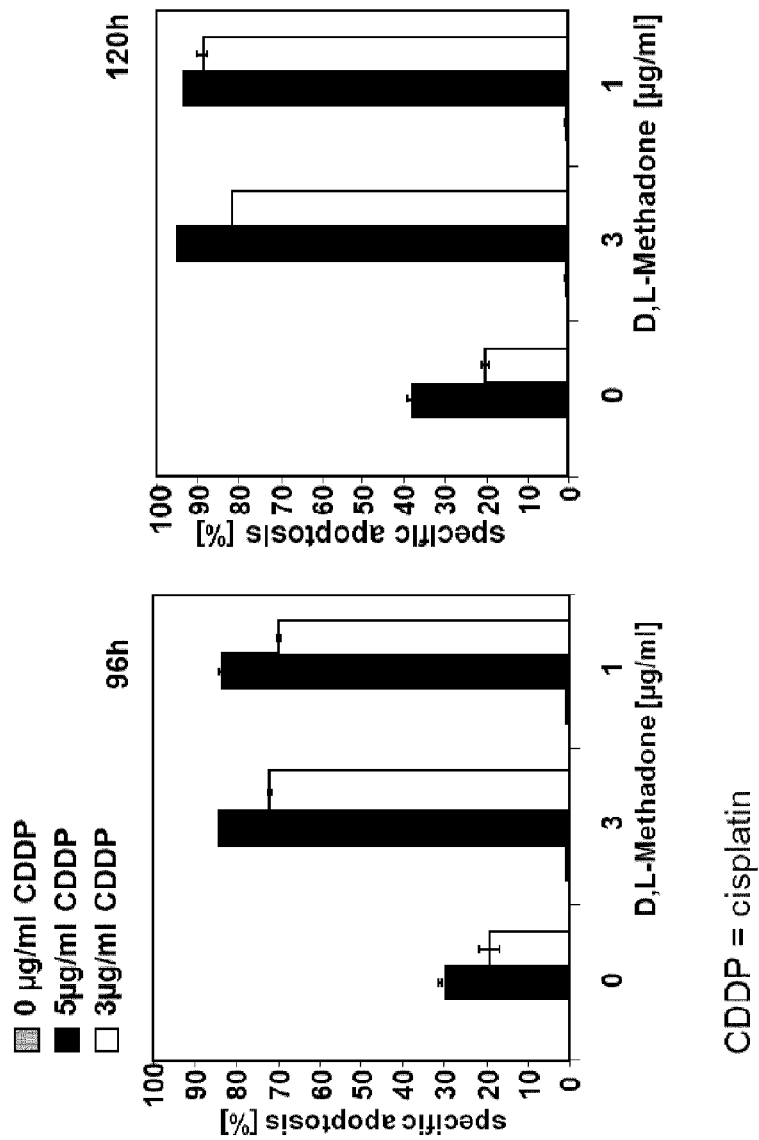

FIG. 44: D,L-methadone sensitizes prostate cancer cells for cisplatin treatment. Prostate cancer cells PC-3 were treated with different concentrations of D,L-methadone (3, 1 µg/mL) alone, with 5 or 3 µg/mL cisplatin alone or in combination with D,L-methadone and 5 µg/mL cisplatin (+5 µg/ml CDDP, black columns) or 3 µg/mL cisplatin (+3 µg/mL, white columns). After 96 h and 120 h, the percentages of apoptotic cells were measured by hypodiploid DNA analysis.

Figure 45:
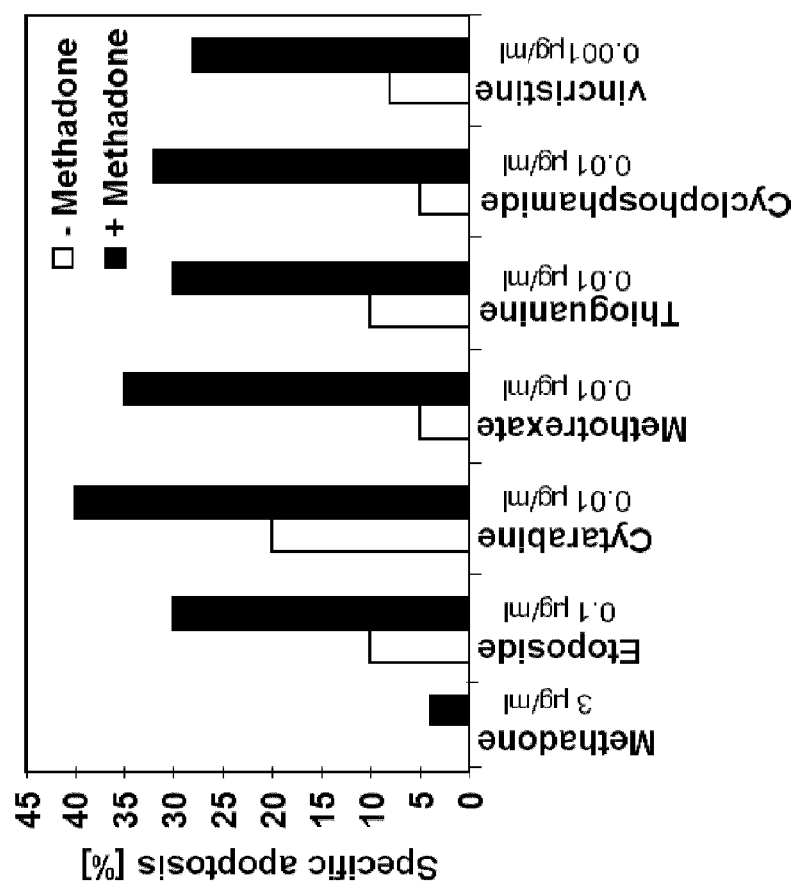

FIG. 45: D,L-methadone sensitizes leukemia cells for treatment with different anticancer drugs. Leukemia cells Nalm6 were treated with D,L-methadone (3 µg/mL) alone, with different anticancer drugs alone as indicated (white columns) or in combination with D,L-methadone and different anticancer drugs (black columns). After 96 h, the percentages of cell death/apoptosis were measured.

Figure 46:
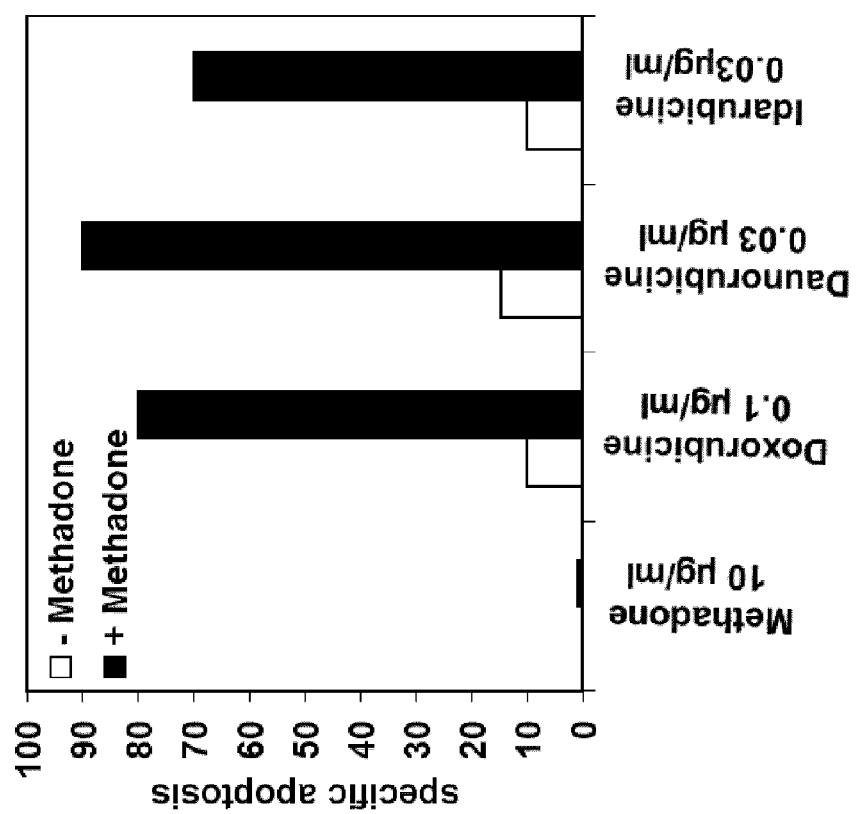

FIG. 46: D,L-methadone sensitizes glioblastoma cells for treatment with different anticancer drugs from the same anti-cancer drug class. Glioblastoma cells A172 were treated with D,L-methadone (3 µg/mL) alone, with different anticancer drugs alone as indicated (white columns) or in combination with D,L-methadone and different anticancer drugs (black columns). After 120 h, the percentages of cell death/apoptosis were measured.

Figure 47:
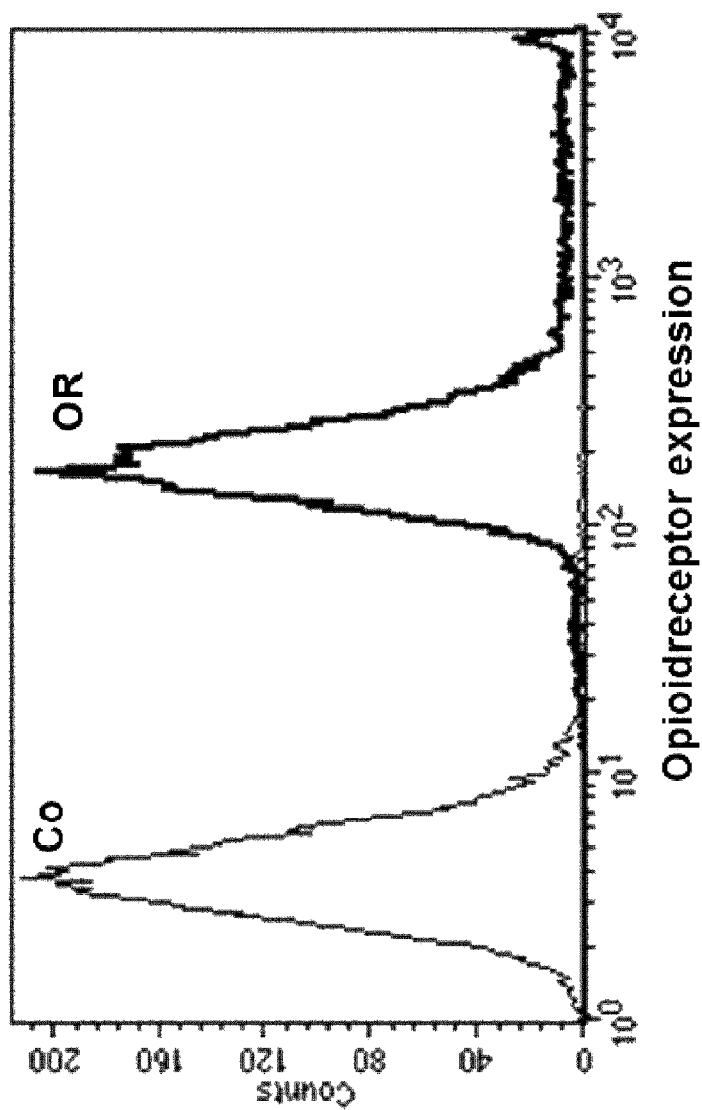

FIG. 47 Opioid receptor expression on pancreatic cancer cells. Pancreatic cancer cells Colo357 were stained with naloxone fluorescein measuring opioid receptor expression (OR, thick black curve) by flow cytometry. Controls (Co) are exhibited as thin black curves. A strong expression of opioid receptors on the surface of pancreatic cancer was found.

Figure 48:
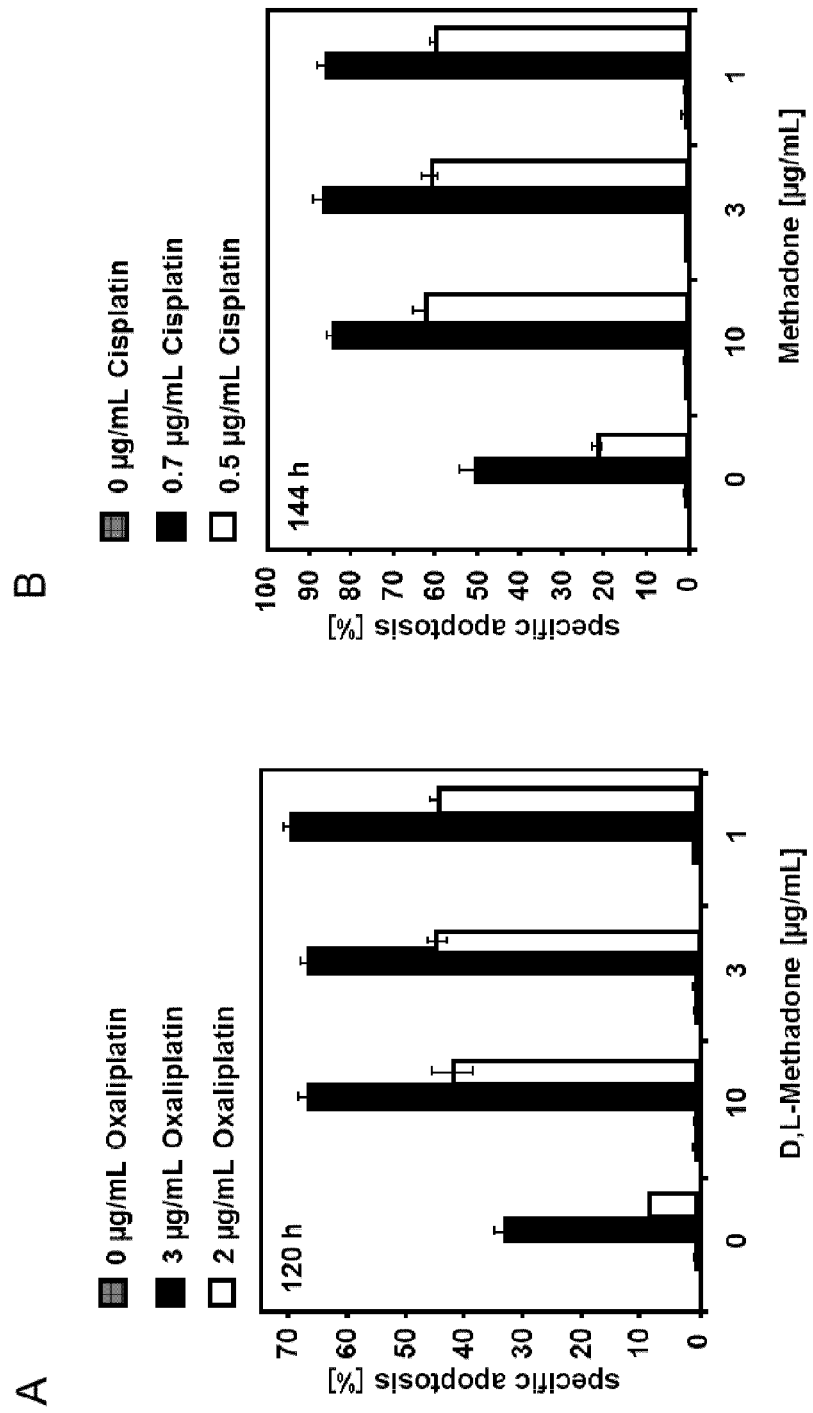

FIG. 48: Opioids such as D,L-methadone increase anticancer drug-induced cell death in pancreatic cancer cells. Pancreatic cancer cells Colo 357 were treated with D,L-methadone (10, 3, 1, 0 µg/mL) alone, with oxaliplatin or cisplatin alone as indicated or with a combination of D,L-methadone and (A) oxaliplatin or (B) cisplatin. After 120 h (A) and 144 (B), the percentages of cell death/apoptosis were measured.

Figure 49:
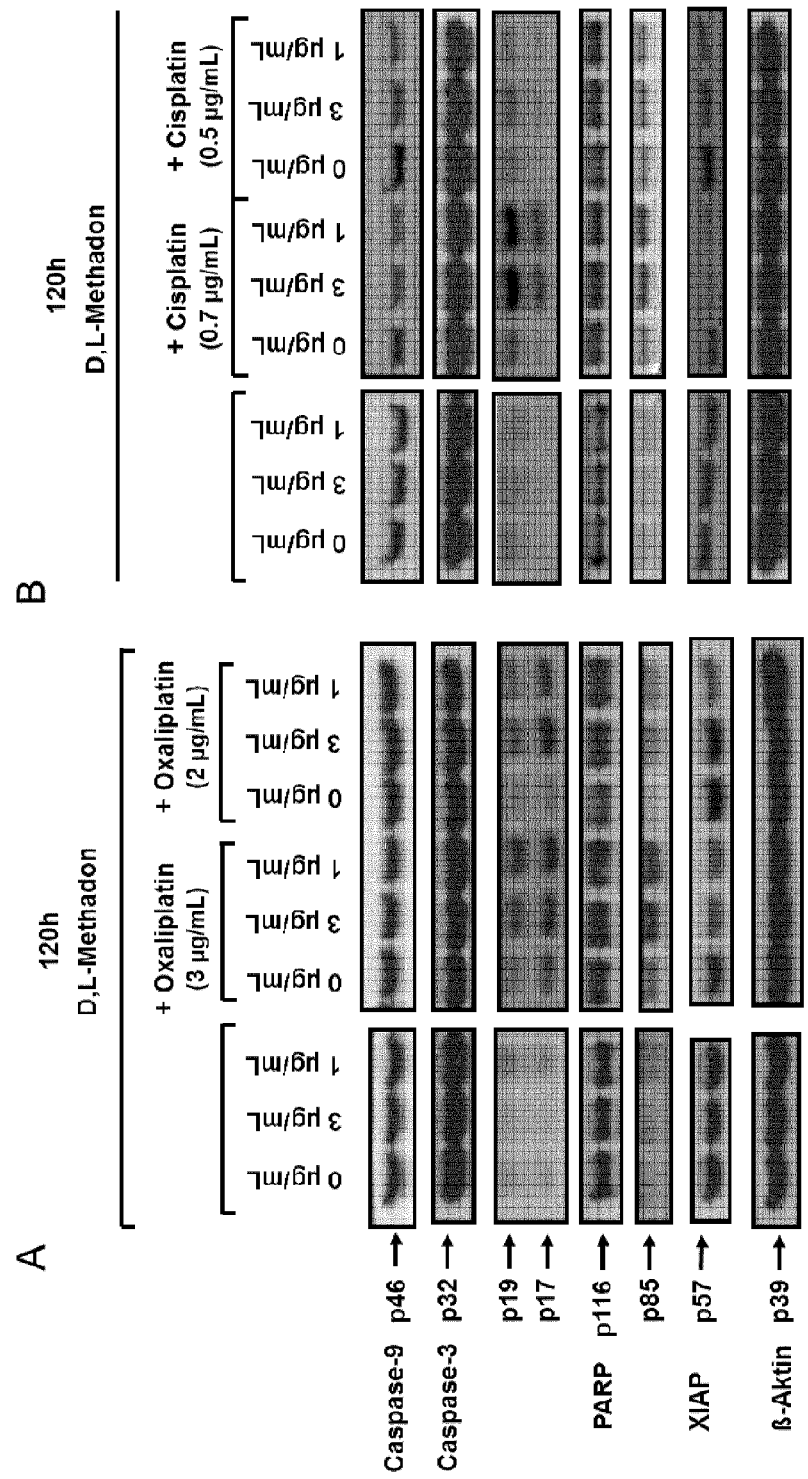

FIG. 49: Opioid receptor activation using D,L-methadone sensitizes pancreatic cancer cells for cisplatin- and oxaliplatin-induced activation of caspases. D,L-Methadone restored deficient caspases activation by (A) oxaliplatin or (B) cisplatin in pancreatic cancer cells. Pancreatic cancer cells Colo 357 were treated with different concentrations of D,L-methadone (3, 1 µg/mL) alone, with (A) oxaliplatin (2, 3 µg/mL) alone, or (B) with cisplatin (0.5 or 0.7 µg/mL) alone or with (A) D,L-methadone (3, 1 µg/mL) in addition to 2 or 3 µg/mL oxaliplatin or with (B) D,L-methadone (3, 1 µg/mL) in addition to 0.5 or 0.7 µg/mL cisplatin. After 120 h, Western blot analyses were performed. The active fragment of caspase-9 was detected at ~46 kDa, the active fragment of caspase-3 at ~19 and 17 kDa, and PARP cleavage at ~85 kDa. The inhibitory protein of caspases XIAP was detected at ~57 kDa Equal protein loading was controlled by anti-β-actin antibody.

Figure 50:
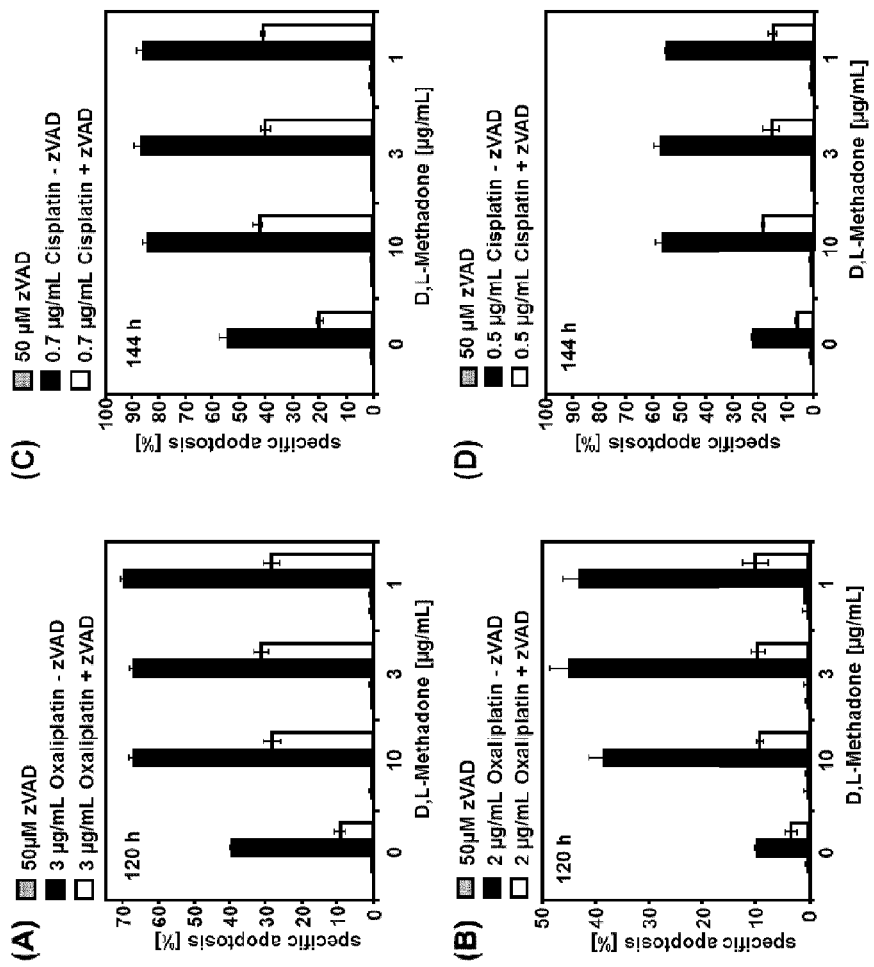

FIG. 50: Inhibition of caspases activation blocks opioid-sensitized pancreatic cancer cells for oxaliplatin- or cisplatin-induced apoptosis. Pancreatic cancer cells Colo 357 were treated with different concentrations of D,L-methadone (10, 3, 1, 0 µg/mL) in combination with (A) 3 µg/mL oxaliplatin, (B) 2 µg/mL oxaliplatin, (C) 0.7 µg/mL cisplatin or (D) 0.5 µg/mL cisplatin without (−zVAD.fmk, black columns) or with addition of 50 µmol/L zVAD.fmk (+zVAD, white columns). After 120 h and 144 h, the percentages of cell death/apoptotic cells were measured.

Figure 51:
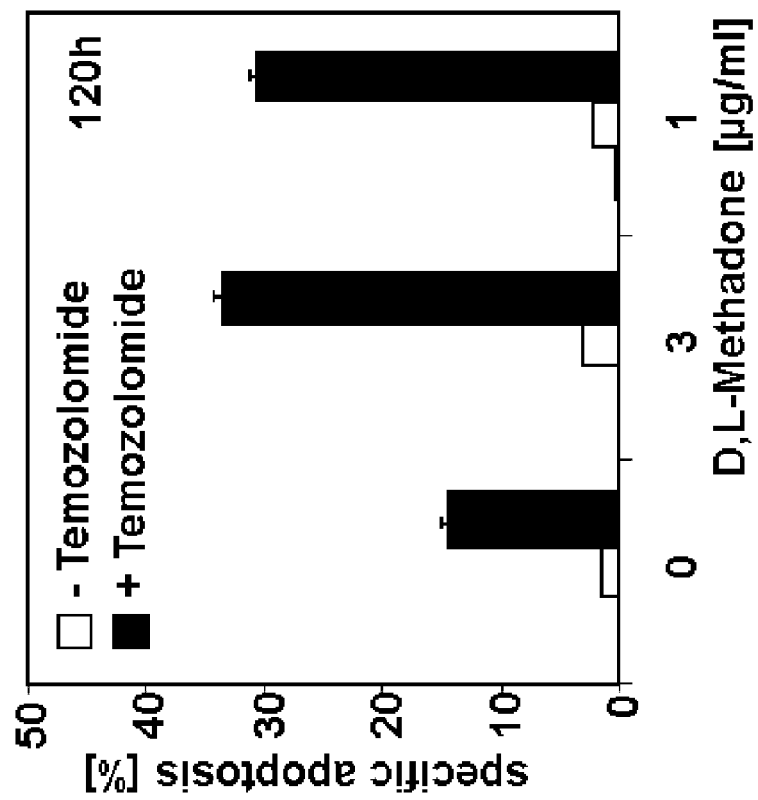

FIG. 51: Opioids using D,L-methadone sensitizes glioblastoma cells for temozolomide treatment. Glioblastoma cells A172 were treated with different concentrations of D,L-methadone 3, 1, 0 µg/mL) alone, with temozolomide alone or in combination with D,L-methadone and temozolomide (black columns). After 120 h, the percentages of apoptotic cells were measured.

Figure 52:
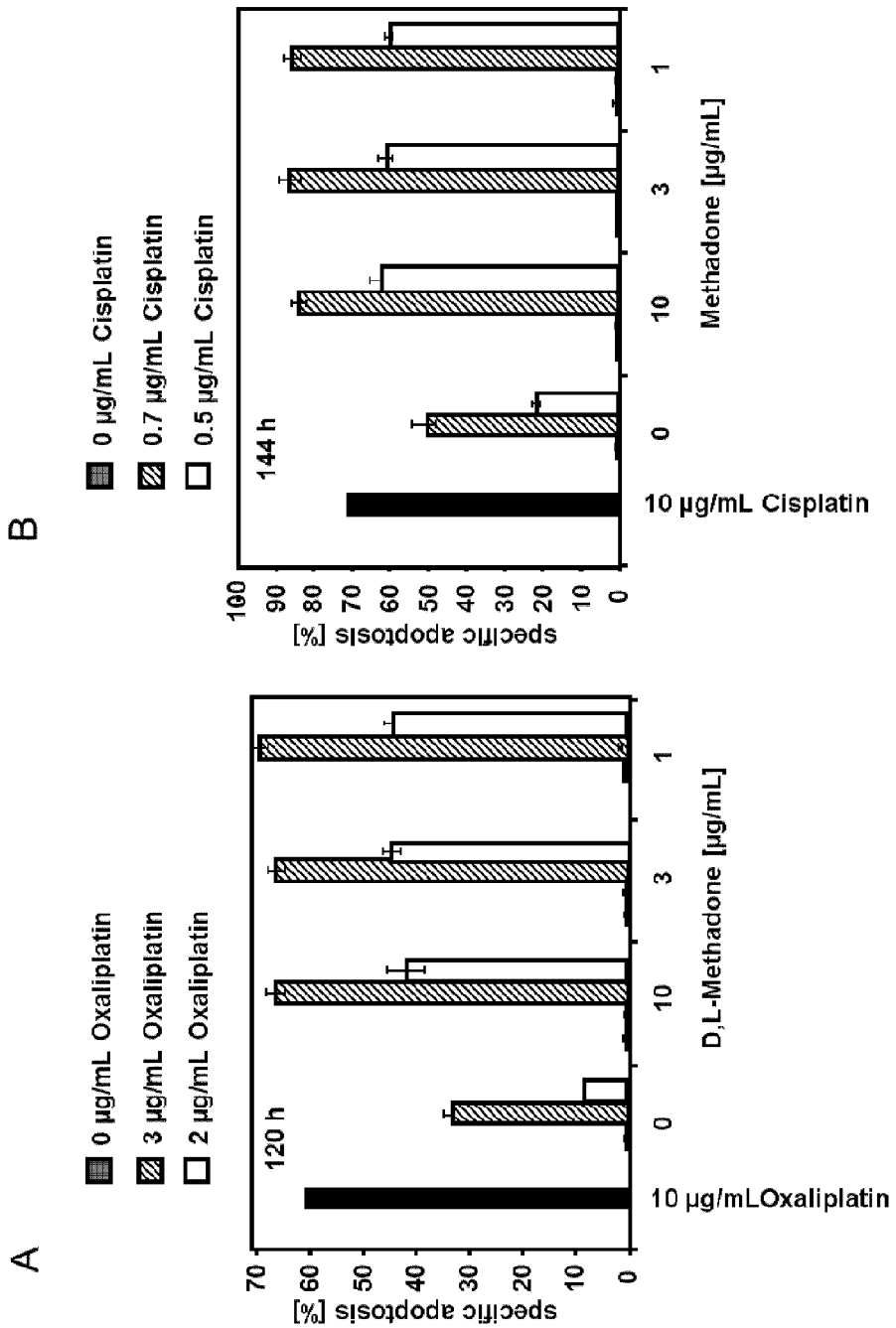

FIG. 52: Opioids using D,L-methadone strongly sensitizes pancreatic cancer cells for oxaliplatin and cisplatin treatment.

(A) Pancreatic cancer cells (Colo 357) were treated with different concentrations of D,L-methadone (10, 3, 1, 0 µg/mL) alone, with 10 µg/mL oxaliplatin (black column), 3, 2 µg/ml oxaliplatin alone and with 3 µg/mL oxaliplatin in combination with D,L-methadone (hatched columns) or 2 µg/mL oxaliplatin in combination with D,L-methadone (white columns) as indicated. After 120 h, the percentages of cell death/apoptotic cells were measured.

(B) Pancreatic cancer cells (Colo 357) were treated with different concentrations of D,L-methadone (10, 3, 1, 0 µg/mL) alone, with 10 µg/mL cisplatin (black column), 0.7 or 0.5 µg/ml cisplatin alone and with 0.7 µg/mL cisplatin in combination with D,L-methadone (hatched columns) or 0.5 µg/mL cisplatin in combination with D,L-methadone (white columns) as indicated. After 144 h, the percentages of cell death/apoptotic cells were measured.

Figure 53:
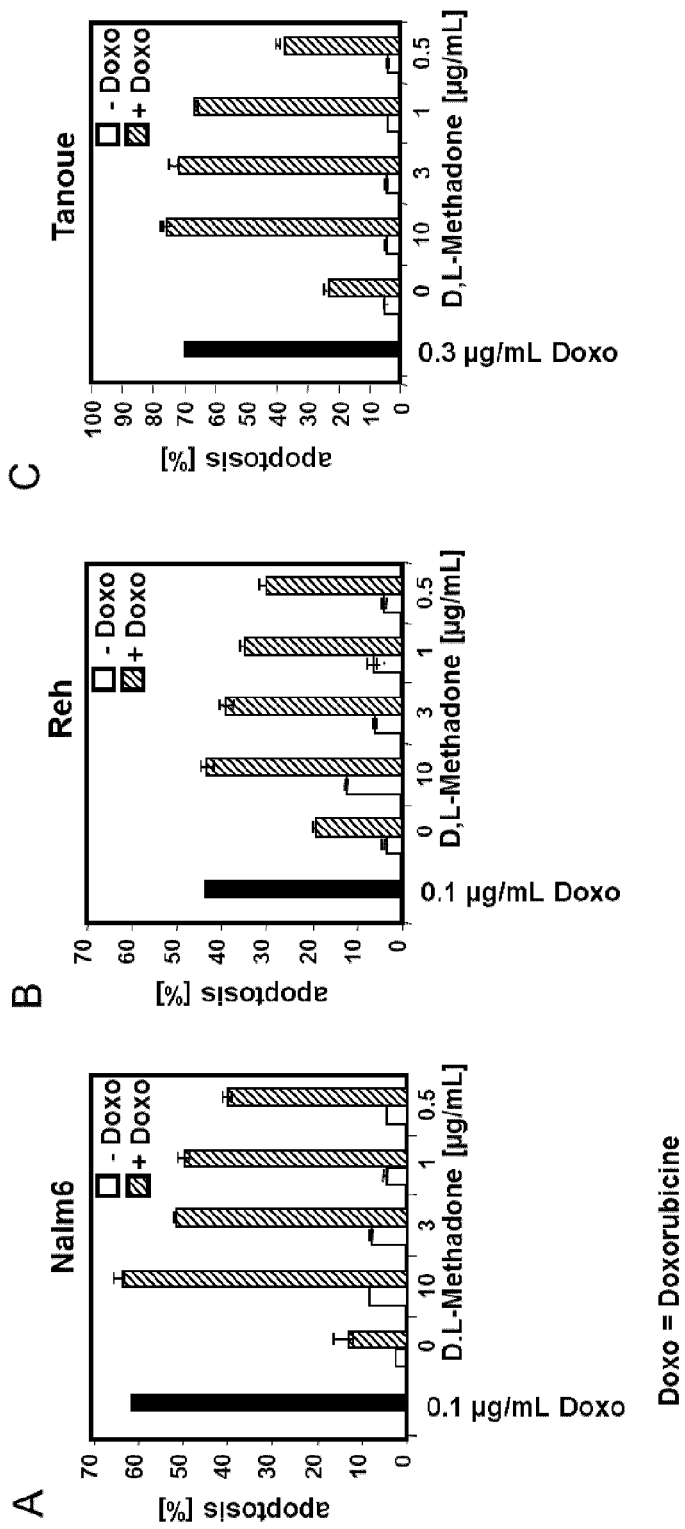

FIG. 53: Opioids using D,L-methadone strongly sensitizes leukemia cells for doxorubicin treatment.

(A) Leukemia cells (Nalm6) were treated with different concentrations of D,L-methadone (10, 3, 1, 0 µg/mL) alone, with 0.1 µg/ml doxorubicin (black column) alone, with 0.01 µg/ml doxorubicin alone or with a combination of 0.01 µg/mL doxorubicin and D,L-methadone (hatched columns) as indicated. After 120 h, the percentages of cell death/apoptotic cells were measured.

(B) Leukemia cells (Reh) were treated with different concentrations of D,L-methadone (10, 3, 1, 0 µg/mL) alone, with 0.1 µg/ml doxorubicin (black column) alone, with 0.01 µg/ml doxorubicin alone, or with a combination of 0.01 µg/mL doxorubicin and D,L-methadone (hatched columns) as indicated. After 120 h, the percentages of cell death/apoptotic cells were measured.

(C) Leukemia cells (Tanoue) were treated with different concentrations of D,L-methadone (10, 3, 1, 0 µg/mL) alone, with 0.1 µg/ml doxorubicin (black column) alone, with 0.01 µg/ml doxorubicin alone, or with a combination of 0.01 µg/mL doxorubicin and D,L-methadone (hatched columns) as indicated. After 120 h, the percentages of cell death/apoptotic cells were measured.

Figure 54:
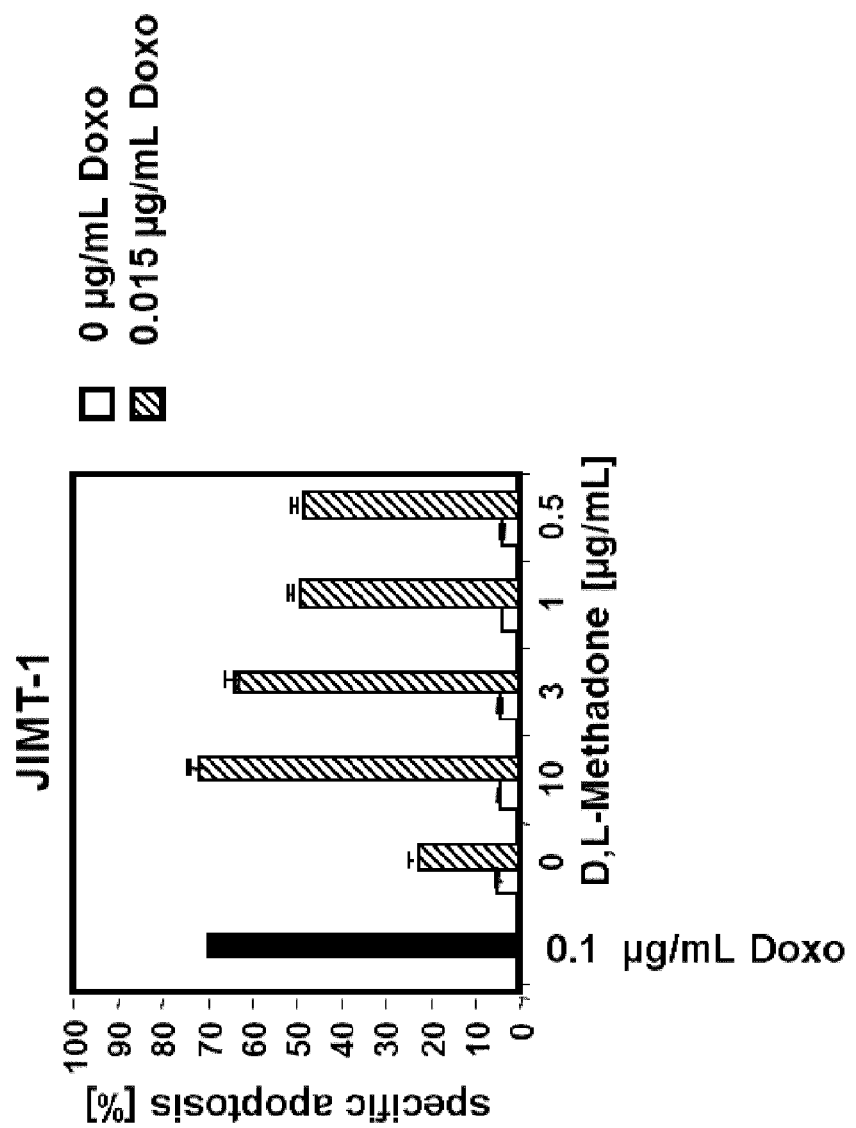

FIG. 54: Opioids using D,L-methadone strongly sensitizes breast cancer cells for doxorubicin treatment.

(A) Breast cancer cells resistant to HER2-targeted therapies (JIMT-1) were treated with different concentrations of D,L-methadone (10, 3, 1, 0 µg/mL) alone, with 0.1 µg/ml doxorubicin (black column) alone or with 0.015 µg/ml doxorubicin alone and with 0.015 µg/mL doxorubicin in combination with D,L-methadone (hatched columns) as indicated. After 120 h, the percentages of cell death/apoptotic cells were measured.

Figure 55:
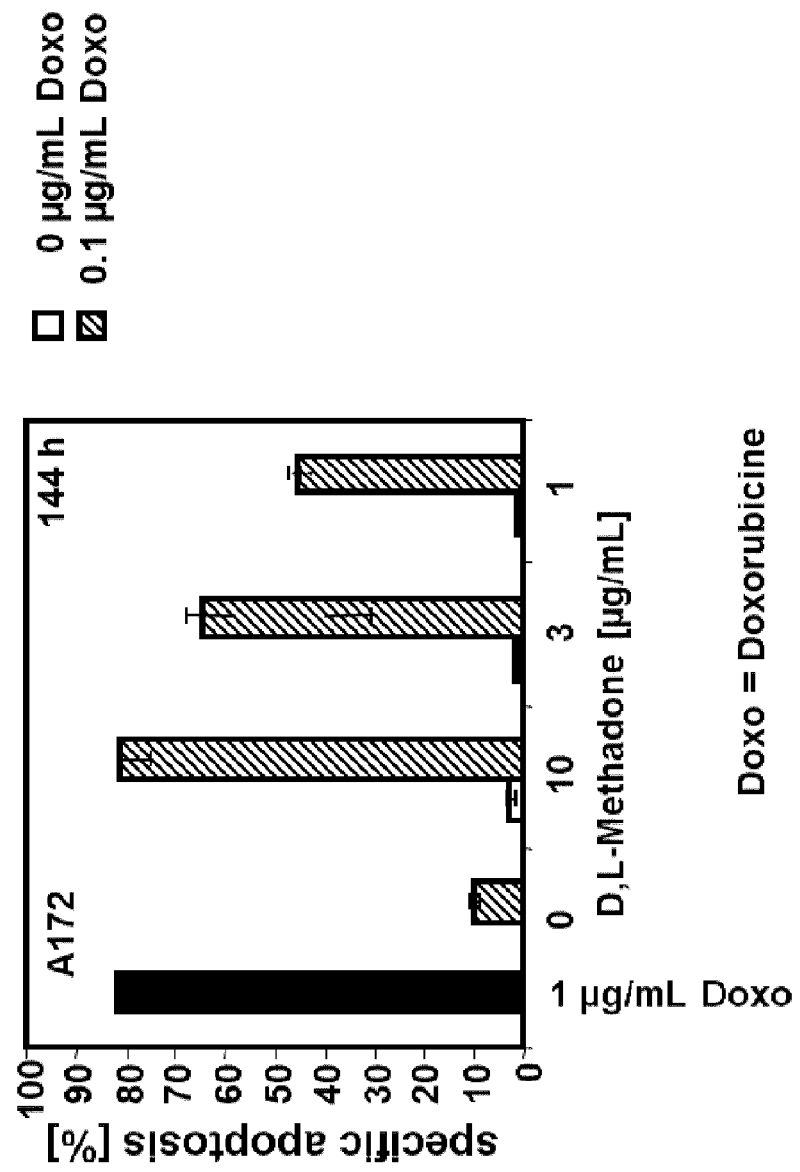

FIG. 55: Opioids using D,L-methadone strongly sensitizes glioblastoma cells for doxorubicin treatment.

Glioblastoma cells (A172) were treated with different concentrations of D,L-methadone (10, 3, 1, 0 µg/mL) alone, with 1 µg/ml doxorubicin (black column) alone, with 0.1 µg/ml doxorubicin alone or with a combination of 0.1 µg/mL doxorubicin and D,L-methadone (hatched columns) as indicated. After 144 h, the percentages of cell death/apoptotic cells were measured.

Figure 56:
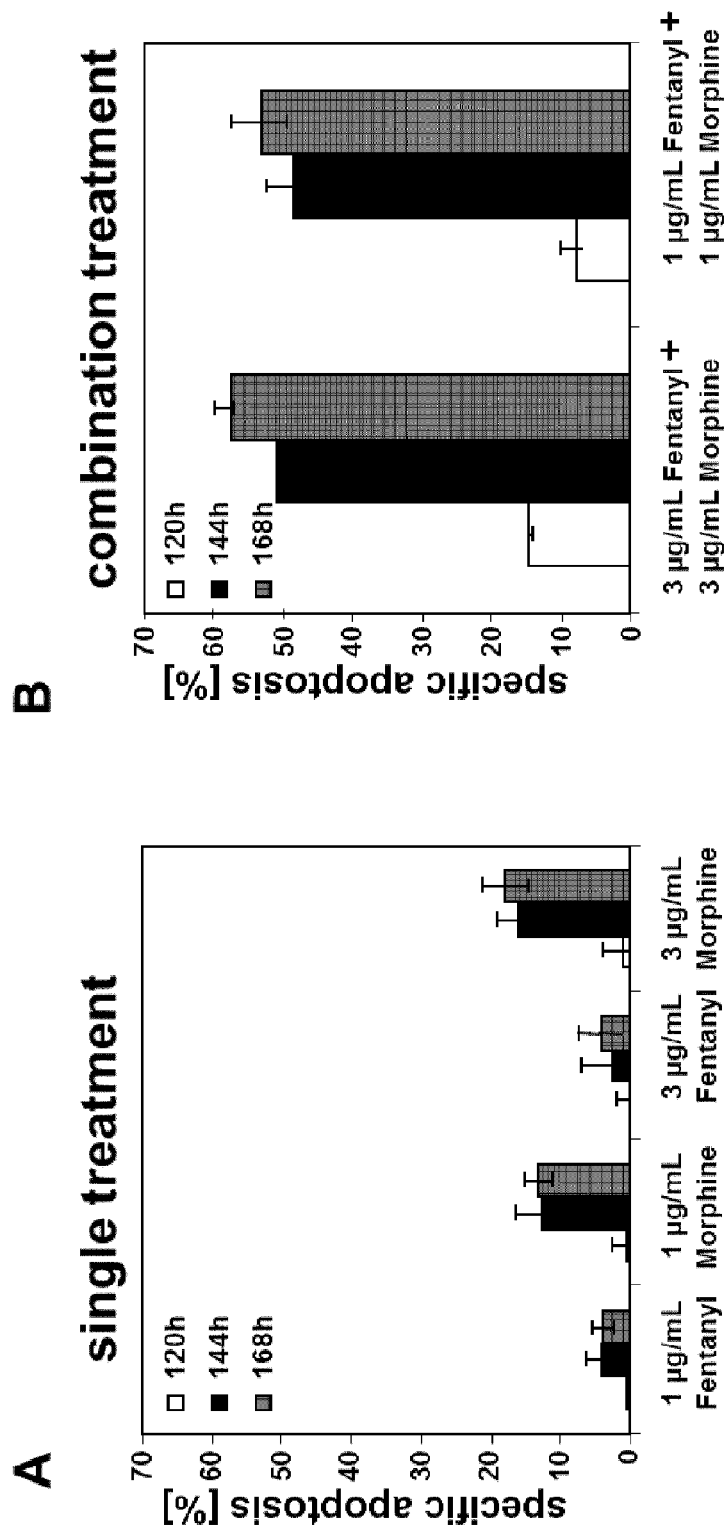

FIG. 56: Combination treatment of morphine and fentanyl shows a strong synergistic effect for inducing cell death in leukemia cells. HL60 leukemia cells were treated with fentanyl (3, 1 µg/mL) alone (A) or morphine (3, 1 µg/mL) alone (A) or with a combination of fentanyl and morphine (B) at concentrations as indicated. After 96 h, 120 h and 144 h, the percentages of specific cell death/apoptotic cells were measured.

LITERATURE

Addeo, R., Caraglia, M., Baldi, A., D'Angelo, V., Casale, F., Crisci, S., Abbruzzese, A., Vincenze, B., Campioni, M., Di Tullio, M. T., and Indolfi, P. (2005). Prognostic role of bcl-xL and p53 in childhood acute lymphoblastic leukemia (ALL). Cancer Biol Ther 4, 32-38.

Bergmann J P, Harris D. Radioresistance, chemoresistance and apoptosis resistance. Radiation Oncology 1997; 27:47-57.

Boecker W et al., eds., chapter 6: "Tumorerkrankungen" in Pathologie, Urban & Fischer, Elsevier, 4th edition, 2008.

Borgmann, A., Baldy, C., von Stackelberg, A., Beyermann, B., Fichtner, I., Nurnberg, P., and Henze, G. (2000). Childhood all blasts retain phenotypic and genotypic characteristics upon long-term serial passage in NOD/SCID mice. Pediatr Hematol Oncol 17, 635-650.

Carbonari M, Cibati M, Cherchi M, et al. Detection and characterization of apoptotic peripheral blood lymphocytes in human immunodeficiency virus-infection and cancer chemotherapy by a novel flow immunocytometric method. Blood 1994; 83:1268-77.

Classen, C. F., Falk, C. S., Friesen, C., Fulda, S., Herr, I., and Debatin, K. M. (2003). Natural killer resistance of a drug-resistant leukemia cell line, mediated by up-regulation of HLA class I expression. Haematologica 88, 509-521.

Crettol, S., Digon, P., Golay, K. P., Brawand, M., and Eap, C. B. (2007). In vitro P-glycoprotein-mediated transport of (R)-, (S)-, (R,S)-methadone, LAAM and their main metabolites. Pharmacology 80, 304-311.

Diestra, J. E., Condom, E., Del Muro, X. G., Scheffer, G. L., Perez, J., Zurita, A. J., Munoz-Segui, J., Vigues, F., Scheper, R. J., Capella, G., et al. (2003). Expression of multidrug resistance proteins P-glycoprotein, multidrug resistance protein 1, breast cancer resistance protein and lung resistance related protein in locally advanced bladder cancer treated with neoadjuvant chemotherapy: biological and clinical implications. J Urol 170, 1383-1387.

Friesen C, Glatting G, Koop B, et al. Breaking chemo- and radioresistance with [$^{213}$Bi]anti-CD45 antibodies in leukemia cells. Cancer Res 2007; 67(5):1950-8.

Friesen C, Kiess Y, Debatin KM. A critical role of glutathione in determining apoptosis sensitivity and resistance in leukemia cells. Cell Death Differ 2004; 11(Suppl 1):S73-85.

Fulda, S. (2009a). Cell death in hematological tumors. Apoptosis 14, 409-423.

Fulda, S. (2009b). Therapeutic opportunities for counteracting apoptosis resistance in childhood leukemia. Br J Haematol 145, 441-454.

Fulda, S. (2009c). Tumor resistance to apoptosis. Int J Cancer 124, 511-515.

Hilger, R. A., Richly, H., Grubert, M., Oberhoff, C., Strumberg, D., Scheulen, M. E., and Seeber, S. (2005). Pharmacokinetics (PK) of a liposomal encapsulated fraction containing doxorubicin and of doxorubicin released from the liposomal capsule after intravenous infusion of Caelyx/Doxil. Int J Clin Pharmacol Ther 43, 588-589.

Law, P. Y., Wong, Y. H., and Loh, H. H. (2000). Molecular mechanisms and regulation of opioid receptor signaling. Annu Rev Pharmacol Toxicol 40, 389-430. Law 2000.

Naderi, E. H., Findley, H. W., Ruud, E., Blomhoff, H. K., and Naderi, S. (2009). Activation of cAMP signaling inhibits DNA damage-induced apoptosis in BCP-ALL cells through abrogation of p53 accumulation. Blood 114, 608-618.

Nicoletti, I., Migliorati, G., Pagliacci, M. C., Grignani, F., and Riccardi, C. (1991). A rapid and simple method for measuring thymocyte apoptosis by propidium iodide staining and flow cytometry. J Immunol Meth 139, 271-279.

Posovszky, C., Friesen, C., Herr, I., and Debatin, K. M. (1999). Chemotherapeutic drugs sensitize pre-B ALL cells for CD95- and cytotoxic T-lymphocyte-mediated apoptosis. Leukemia 13, 400-409.

Richly, H., Henning, B. F., Kupsch, P., Passarge, K., Grubert, M., Hilger, R. A., Christensen, O., Brendel, E., Schwartz, B., Ludwig, M., et al. (2006). Results of a Phase I trial of sorafenib (BAY 43-9006) in combination with doxorubicin in patients with refractory solid tumors. Ann Oncol 17, 866-873.

Safa, M., Kazemi, A., Zand, H., Azarkeivan, A., Zaker, F., and Hayat, P. (2010a). Inhibitory role of cAMP on doxorubicin-induced apoptosis in pre-B ALL cells through dephosphorylation of p53 serine residues. Apoptosis 15, 196-203.

Workman, P., Aboagye, E. O., Balkwill, F., Balmain, A., Bruder, G., Chaplin, D. J., Double, J. A., Everitt, J., Farningham, D. A., Glennie, M. J., et al. (2010), Guidelines for the welfare and use of animals in cancer research. Br J Cancer 102, 1555-1577

The invention claimed is:

1. A method of using a combination of an opioid receptor agonist and at least one conventional anticancer treatment in treating resistant cancers in a patient, wherein the method comprises:
   (a) administering said opioid receptor agonist to the patient with resistant cancer in one or more doses to establish a therapeutically effective plasma level for a period of at least four weeks, and
   (b) administering to the patient with resistant cancer at least one conventional anticancer treatment that is selected from the group consisting of chemotherapeutical agents, cytotoxic agents, cytostatic agents, immunotoxic agents and radiotherapy, to establish a period with a therapeutically effective plasma level, wherein the conventional anticancer treatment selected is well known to have an effect on a type of cancer in the patient, and
   (c) wherein said periods of a) and b) overlap; and whereby said at least one conventional anticancer treatment and said opioid receptor agonist are administered successively with the opioid receptor agonist being administered first.

2. The method according to claim 1, wherein said opioid receptor agonist is capable of inhibiting cell proliferation and/or inducing cell death.

3. The method according to claim 1, wherein the patient has received a pre-treatment comprising conventional anticancer treatment.

4. The method according to claim 1 wherein the opioid receptor agonist is selected from the group consisting of:
  i. compounds of the methadone group selected from the group consisting of D/L-methadone, D-methadone, L-methadone, and normethadone;
  ii. fentanyl derivatives selected from the group consisting of fentanyl, sufentanyl and carfentanyl;
  iii. morphinane compounds selected from the group consisting of morphine, codeine, heroine, dextrallorphane, dextromethorphan, dextrophanol, dimemorfan, levalorphan, levofurethylnormorphanol, levomethorphane, levophenacylmorphane, levorphanol, methorphane, morphanol, oxilorphan, phenomorphan, and xorphanol;
  iv. benzomorphane derivatives selected from the group consisting of 5,9-DEHB, alazocine, anazocine, bremazocine, butinazocine, carbazocine, cogazocine, cyclazocine, dezocine, eptazocine, etazocine, ethylketocyclazocine, fluorophen, gemazocine, ibazocine, ketazocine, metazocine, moxazocine, pentazocine, phenazocine, quadazocine, thiazocine, tonazocine, volazocine and 8-CAC;
  v. 4-phenylpiperidine derivatives selected from the group consisting of pethidine, ketobemidone, anileridine, piminodine, phenoperidine, furethidine, alpha-prodin, trimeperidine, 4-phenylpyrrolidine derivatives, profadol, 4-phenylazepanderivates, and meptazinol;
  vi. cyclohexane derivatives selected from the group consisting of tilidine, U-50488, tramadol and tapentadol; and
  vii. endogenous opioids selected from the group consisting of endorphins, enkephalins, dynorphins, nociceptin, dermorphins, morphiceptin, endomorphines and fragments derived from the protein proopiomelanocortin (POMC).

5. The method according to claim 1 wherein the opioid receptor agonist belongs to a methadone group.

6. The method according to claim 1, wherein the opioid receptor agonist is D/L methadone and a hydrochloride form thereof.

7. The method according to claim 1 wherein the conventional anticancer treatment is a chemotherapeutic, cytotoxic, or cytostatic agent selected from the group consisting of:
  i. intercalating substances selected from the group consisting of doxorubicin, idarubicin, and daunorubicin;
  ii. a topoisomerase inhibitor selected from etoposide;
  iii. a nitrogen mustard selected from cyclophosphamide;
  iv. an alkylating agent selected from temozolomide;
  v. platinum analogues selected from the group consisting of cisplatin and oxaliplatin;
  vi. an antifolate selected from methotrexate;
  vii. a purine analogue selected from thioguanine; and
  viii. a pyrimidine analogue selected from cytarabine.

8. The method according to claim 1 wherein the anticancer agent is methotrexate, cytarabine, cisplatin, temozolomide, etoposide, vincristine, thioguanine, gemcitabine, beta irradiation or gamma irradiation.

9. The method according to claim 1 wherein patients suffer from a neoplasm as classified according the International statistical classification of Diseases and related health problems 10$^{th}$ Revision (ICD-10), and wherein the neoplasm is selected from the group consisting of malignant neoplasms of classes C00 to C97, in situ neoplasms of classes D00 to D09, benign neoplasms of classes D10 to D36, and neoplasms of uncertain or unknown behaviour of classes D37 to D48.

10. The method according to claim 1 wherein the patient suffers from a neoplasm selected from the group consisting of pancreatic carcinoma, mamma carcinoma, ovarian carcinoma, prostate carcinoma, glioblastoma, acute lymphoblastic leukemia, acute myeloid leukemia, chronic myeloid leukemia, chronic lymphocytic leukemia, pro-forms of leukemia, and hairy cell leukemia.

11. The method according to claim 1, wherein the patient exhibits acquired resistance.

12. The method according to claim 11, wherein the patient exhibits acquired resistance to the conventional anticancer treatment.

13. The method according to claim 1, wherein the conventional anticancer treatment is given at a dose lower than a recommended dose for a treatment of the type of cancer in the patient.

14. The method according to claim 13, wherein the dose is 3 times lower than the recommended dose.

15. The method according to claim 1, wherein at least one additional opioid receptor agonist is administered to the patient.

16. The method according claim 4, wherein the opioid morphine is administered with a further opioid fentanyl to the patient.

17. The method according to claim 1, wherein the administration period for the opioid receptor agonist providing a therapeutically relevant dose represents a chronic treatment.

18. The method according to claim 13, wherein the conventional anticancer treatment is given at a dose 30 times lower than the recommended dose.

19. The method according to claim 13, wherein the conventional anticancer treatment is given at a dose 100 times lower than the recommended dose.

20. The method according to claim 1 wherein the conventional anticancer treatment comprises administration of doxorubicin, cisplatin, or oxaliplatin.

21. The method according to claim 1 wherein the opioid receptor agonist is given in a way that the patient develops a habituation against said opioid receptor agonist.

22. The method according to claim 21 wherein step (b) of the method is not started until the habituation period has begun.

23. The method according to claim 21 wherein step (b) of the method is not started until the habituation period reaches a plateau.

24. A method of using a combination of an opioid receptor agonist and at least one anticancer agent in treating resistant cancers in a patient, wherein the method comprises:
  (a) administering said opioid receptor agonist to the patient with resistant cancer in one or more doses to establish a therapeutically effective plasma level for a period of at least four weeks, wherein the opioid receptor agonist belongs to a methadone group; and
  (b) administering to the patient with resistant cancer at least one anticancer agent, the at least one anticancer agent being a DNA intercalating agent selected from doxorubicin, idarubicin and daunorubicin; and
  (c) wherein said periods of a) and b) overlap; and
  whereby the anticancer agent is given at a dose lower than a recommended dose for a treatment of cancer using the anticancer agent only;
  whereby said at least one anticancer agent and said opioid receptor agonist are administered successively with the opioid receptor agonist being administered first;
  wherein the resistant cancer is glioblastoma or leukemia.

25. The method according to claim 24, wherein the patient has acquired resistance to the anticancer agent.

26. The method of claim 24 wherein said anticancer agent is formulated for oral or intravenous administration.

27. A method of increasing cellular uptake and/or inhibiting cellular efflux of an anticancer agent in a patient, wherein the method comprises:
  (a) administering an opioid receptor agonist to the patient in one or more doses to establish an effective plasma level for a period of at least four weeks; and
  (b) administering at least one anticancer agent to the patient that is selected from the group consisting of chemotherapeutical agents, cytotoxic agents, cytostatic agents, immunotoxic agents, to establish a period with a therapeutically effective plasma level;
  (c) wherein said periods of a) and b) overlap; and
  whereby said at least one anticancer agent and said opioid receptor agonist are administered successively with the opioid receptor agonist being administered first.

28. The method of claim 27, wherein the anticancer agent increases surface expression of opioid receptors on cancer cells in the patient.

\* \* \* \* \*